United States Patent
Ardecky et al.

(10) Patent No.: US 7,176,224 B2
(45) Date of Patent: Feb. 13, 2007

(54) OXAZOLYL-ARYLOXYACETIC ACID DERIVATIVES AND THEIR USE AS PPAR AGONISTS

(75) Inventors: Robert J Ardecky, Encinitas, CA (US); Dawn Alisa Brooks, Indianapolis, IN (US); Alexander Glenn Godfrey, Mooresville, IN (US); Sarah Beth Jones, Greenwood, IN (US); Nathan Bryan Mantlo, Brownsburg, IN (US); James Ray McCarthy, Zionsville, IN (US); Pierre Yves Michellys, San Diego, CA (US); Christopher John Rito, Martinsville, IN (US); John S Tyhonas, San Diego, CA (US); Leonard Larry Winneroski, Greenwood, IN (US); Yanping Xu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 589 days.

(21) Appl. No.: 10/343,187

(22) PCT Filed: Aug. 23, 2001

(86) PCT No.: PCT/US01/22617

§ 371 (c)(1),
(2), (4) Date: Jul. 29, 2003

(87) PCT Pub. No.: WO02/16332

PCT Pub. Date: Feb. 28, 2002

(65) Prior Publication Data

US 2004/0138277 A1    Jul. 15, 2004

Related U.S. Application Data

(60) Provisional application No. 60/227,456, filed on Aug. 23, 2000.

(51) Int. Cl.
*C07D 263/32* (2006.01)
*A61K 31/421* (2006.01)

(52) U.S. Cl. ................................. 514/374; 548/236
(58) Field of Classification Search ................. 548/236
See application file for complete search history.

(56) References Cited

U.S. PATENT DOCUMENTS

| | | |
|---|---|---|
| 5,089,514 A | 2/1992 | Hulin |
| 5,232,945 A | 8/1993 | Hulin |
| 5,306,726 A | 4/1994 | Hulin |
| 5,902,726 A | 5/1999 | Kliewer et al. |
| 5,994,554 A | 11/1999 | Kliewer et al. |

FOREIGN PATENT DOCUMENTS

| | | |
|---|---|---|
| EP | 0 930 299 A1 | 7/1999 |
| GB | 2 359 082 A | 8/2001 |
| WO | WO 97 28115 A1 | 8/1997 |
| WO | WO 97 31907 A1 | 9/1997 |
| WO | WO 99 46232 A1 | 9/1999 |
| WO | WO 01 16120 A1 | 3/2001 |
| WO | WO 02 16331 A1 | 2/2002 |
| WO | WO 02 18355 A1 | 3/2002 |

OTHER PUBLICATIONS

Sarges, R., et al. : "Glucose Transport—Enhancing and Hypoglycemic Activity of 2-Methyl-2-Phenoxy-3-Phenylpropanoic Acids"; Journal of Medicinal Chemistry, vol. 39, No. 24, Nov. 22, 1996, pp. 4783-4803.

Cobb, J. E., et al. : "N- (2-Benzoylphenyl) - L-Tyrosine PPARGamma Agonists. 3. Structure-Activity Relationship and Optimization of the N-Aryl Substituent"; Journal of Medicinal Chemistry, vol. 41, No. 25, Dec. 3, 1998, pp. 5055-5069.

Bright, S.W., et al. : "Competitive Particle Concentration Fluorescence Immunoassays for Measuring Anti-Diabetic Drug Levels in Mouse Plasma"; Journal of Immunological Methods, vol. 207, No. 1, Aug. 22, 1997 (Aug. 2, 1997), pp. 23-31.

Brooks, D., et al. : "Design and Synthesis of 2-methyl-2-{4-'2-'5-methyl-2-aryloxazol-4-yl) ethoxylphenoxy}propionic acids: A New Class of Dual PPARAlpha/Gamma Agonists"; Journal of Medicinal Chemistry, vol. 44, No. 13, Jun. 21, 2001, pp. 2061-2064.

Shinkai, H. et al. : "Isoxazolidine-3, 5-dione and Noncyclic 1, 3-dicarbonyl Compounds as Hypoglycemic Agents"; Journal of Medicinal Chemistry, vol. 41, No. 11, May 21, 1998, pp. 1927-1933.

(Continued)

*Primary Examiner*—Kamal A. Saeed
*Assistant Examiner*—Jason M. Nolan
(74) *Attorney, Agent, or Firm*—Macharri Vorndran-Jones; Soonhee Jang

(57) ABSTRACT

Novel compounds that are modulators of PPAR receptors, and pharmaceutically acceptable salts, solvates and hydrates thereof, processes for making the compounds, pharmaceutical compositions containing the compounds, or pharmaceutically acceptable salts, solvates and hydrates thereof

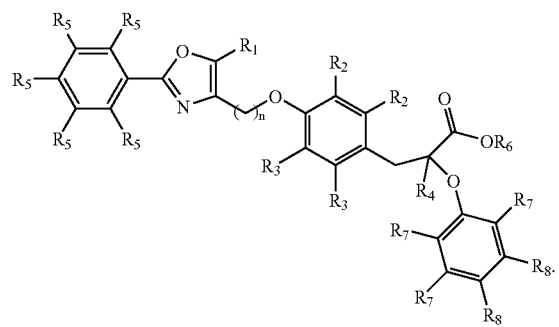

40 Claims, No Drawings

OTHER PUBLICATIONS

Murugesan, N., et al. : "*Biphenylsulfonamide Endothelin Receptor Antogonists 2. Discovery of 4'-oxazoly-lbiphenylsulfonamides as a New Class of Poent, Highly Selective ET(A) Antagonists*"; Journal of Medicinal Chemistry, vol. 43, No. 16, Aug. 10, 2000, pp. 3111-3117.

Malamas, M.S., et al. : "*Azole Phenoxy Hydroxyureas as Selective and Orally Active Inhibitors fo 5-Lipoxygenase*"; Journal of Medicinal Chemistry, vol. 39, No. 1, Jan. 5, 1996, pp. 237-245.

Merguro, K., et al. : "*Studies on Antidiabetic Agents. VII. Synthesis and Hypoglycemic Activity fo 4-Oxazoleacetic Acid Derivatives*"; Chemical & Pharmaceutical Bulletin, vol. 34, No. 7, 1986, pp. 2840-2851.

OXAZOLYL-ARYLOXYACETIC ACID DERIVATIVES AND THEIR USE AS PPAR AGONISTS

This is the national phase application, under 35 USC 371, for PCT/US01/22617, filed 23 Aug. 2001, which claims the priority of U.S. provisional application No. 60/227,456, filed 23 Aug. 2000.

BACKGROUND OF THE INVENTION

Peroxisome Proliferator Activated Receptors (PPARs) are members of the nuclear hormone receptor super family, which are ligand-activated transcription factors regulating gene expression. Various subtypes of PPARs have been discovered. These include PPARα, PPARγ and PPARδ.

The PPARα receptor subtypes are rep to be activated by medium and long-chain fatty acids. They are involved in stimulating beta-oxidation of fatty acids and with the activity of fibrates which reportedly produce a substantial reduction in plasma triglycerides and moderate reduction in low density lipoprotein (LDL) cholesterol. The PPARγ receptor subtypes are reportedly involved in activating the program of adipocyte differentiation and are not involved in stimulating peroxisome proliferation in the liver.

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. "Type II Diabetes" or "non-insulin dependent diabetes mellitus" (NIDDM) is the form of diabetes which is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. When these cells become desensitized to insulin, the body tries to compensate by producing abnormally high levels of insulin and hyperinsulemia results. Hyperinsulemia is associated with hypertension and elevated body weight. Since insulin is involved in promoting the cellular uptake of glucose, amino acids and triglycerides from the blood by insulin sensitive cells, insulin insensitivity can result in elevated levels of triglycerides and LDL which are risk factors in cardiovascular diseases. The constellation of symptoms which includes hyperinsulemia combined with hypertension, elevated body weight, elevated triglycerides and elevated LDL is known as Syndrome X.

Current treatment for diabetes mellitus generally first involves treatment with diet and exercise. However, compliance can be poor and as the disease progresses treatment with hypoglycemics, typically sulfonylureas, is often necessary. Sulfonylureas stimulate the β cells of the liver to secrete more insulin. However, the response of the β cells eventually fails and treatment with insulin injection is necessary. In addition, both sulfonylurea treatment and insulin injection have the life threatening side effect of hypoglycemic coma. Therefore, patients using these treatments must carefully control dosage.

Thiazolidinediones are a class of compounds which have been shown to increase the sensitivity of insulin sensitive cells. Increasing insulin sensitivity rather than the amount of insulin in the blood reduces the likelihood of hypoglycemic coma. Thiazolidinediones have been shown to increase insulin sensitivity by binding to PPARγ receptors. However, side effects associated with treatment with thiazolidinediones include weight gain, and, for troglitazone, liver toxicity.

PPARα and PPARγ receptors have been implicated in diabetes mellitus, cardiovascular disease, obesity, and gastrointestinal disease, such as, inflammatory bowel disease. There exists a need for new pharmaceutical agents which modulate these receptors to prevent, treat and/or alleviate these diseases or conditions while ameliorating side effects of current treatments.

SUMMARY OF THE INVENTION

The present invention is directed to compounds represented by Structural Formula I and pharmaceutically acceptable salts, solvates and hydrates thereof, and methods of making, methods of using, and pharmaceutical compositions having compounds represented by Structural Formula I and pharmaceutically acceptable salts thereof:

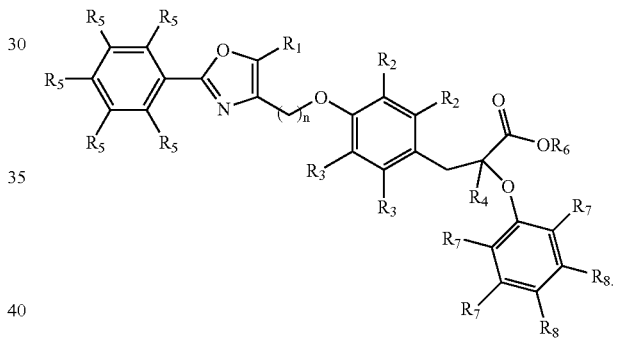

I

In Structural Formula I, n is 2, 3, or 4. $R_1$ is H, a C1–C4 alkyl, phenyl or C1–C4 haloalkyl. $R_2$ are each, independently, H, a C1–C6 alkyl, a C1–C4 alkoxy, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl. $R_3$ are each, independently, H, a C1–C6 alkyl, a C1–C4 alkoxy, an aryl-C1–C6 alkyl, a cycloalkyl-C1–C4 alkyl, an aryl, or a cycloalkyl. $R_4$ is a C1–C4 alkyl. $R_5$ are each, independently, H, a substituted or unsubstituted aryl or a substituted or unsubstituted heteroaryl, provided that at least one $R_5$ is a substituted or unsubstituted aryl or a substituted or unsubstituted heteroaryl. $R_6$ is H, a C1–C4 alkyl, or an aminoalkyl. $R_7$ are each, independently, H, a C1–C4 alkyl, a C1–C4 alkoxy, a halo, C1–C4 haloalkyl, C1–C4 haloalkoxy, or a cycloalkyl. $R_8$ are each, independently, H, a C1–C4 alkyl, a C1–C4 alkoxy, a halo, C1–C4 haloalkyl, C1–C4 haloalkoxy, a cycloalkyl, or each $R_8$ taken together with the phenyl to which they are attached are benzodioxolyl.

The present invention is additionally directed to compounds represented by Structural Formula Ia and pharmaceutically acceptable salts, solvates and hydrates thereof, and methods of making, methods of using, and pharmaceutical compositions having compounds represented by Structural Formula Ia and pharmaceutically acceptable salts thereof:

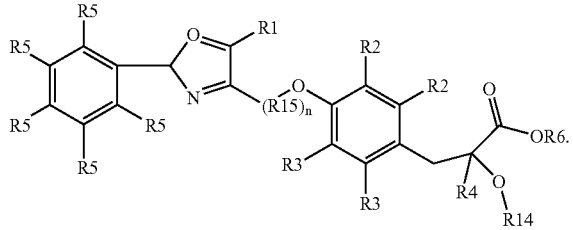

In Structural Formula Ia, n is 1, 2, 3, or 4. $R_1$ is H, a C1–C4 alkyl, phenyl or C1–C4 haloalkyl. $R_2$ are each, independently, H, a C1–C6 alkyl, a C1–C4 alkoxy, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl. $R_3$ are each, independently, H, a C1–C6 alkyl, a C1–C4 alkoxy, an aryl-C1–C6 alkyl, a cycloalkyl-C1–C4 alkyl, an aryl, or a cycloalkyl. $R_4$ is a C1–C4 alkyl. $R_5$ are each, independently, H, a substituted or unsubstituted aryl or a substituted or unsubstituted heteroaryl, provided that at least one $R_5$ is a substituted or unsubstituted aryl or a substituted or unsubstituted heteroaryl. $R_6$ is H, a C1–C4 alkyl, or an aminoalkyl. $R_7$ are each, independently, H, a C1–C4 alkyl, a C1–C4 alkoxy, a halo, C1–C4 haloalkyl, C1–C4 haloalkoxyl, heterocycle, or a cycloalkyl. $R_8$ are each, independently, H, a C1–C4 alkyl, a C1–C4 alkoxy, a halo, C1–C4 haloalkyl, C1–C4 haloalkoxy, a cycloalkyl, or each $R_8$ taken together with the phenyl to which they are attached are benzodioxolyl. R14 is substituted or unsubstituted aryl, substituted or unsubstituted heteroaryl. R15 is substituted or unsubstituted (CH$_2$). An especially preferred R14 group as shown by structure Ia, is of the formula:

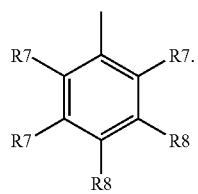

Another R14 group that may be preferred is of the structure:

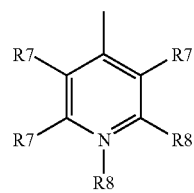

An especially preferred embodiment of this invention is a compound of the structure Ib

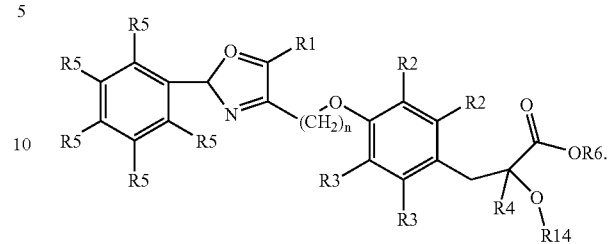

Provided by another embodiment of the present invention, are compounds represented by Structural Formula Ic and pharmaceutically acceptable salts, solvates and hydrates thereof, and methods of making, methods of using, and pharmaceutical compositions having compounds represented by Structural Formula Ic and pharmaceutically acceptable salts thereof:

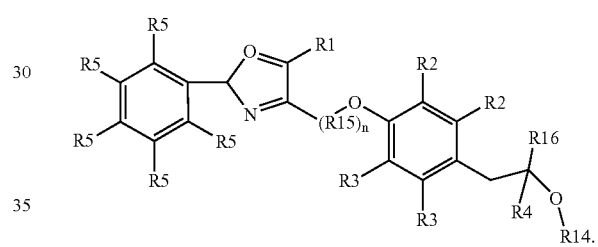

In Structural Formula Ic, n, $R_1$, $R_2$, $R_3$, $R_4$, $R_5$, $R_7$, $R_8$, R14 and R15 are as described herein above by Structure Ia. R16 is acid bioisosteres.

In one embodiment, the present invention relates to a method of modulating a peroxisome proliferator activated receptor by contacting the receptor with at least one compound represented by Structural Formula I, and pharmaceutically acceptable salts, solvates and hydrates thereof In another embodiment, the present invention also relates to pharmaceutical compositions which include a pharmaceutically acceptable carrier and at least one compound represented by Structural Formula I, and pharmaceutically acceptable salts, solvates and hydrates thereof.

In yet another embodiment, the present invention relates to a method of making a compound represented by Structural Formula I.

The compounds of the present invention and pharmaceutically acceptable salts, solvates and hydrates thereof are believed to be effective in treating Syndrome X, Type II diabetes, hyperglycemia, hyperlipidemia, obesity, coagaulopathy, hypertension, atherosclerosis, and other disorders related to Syndrome X and cardiovascular diseases because they lower one or more of the following in mammals: glucose, insulin, triglycerides, fatty acids and/or cholesterol. In addition, the compounds exhibit fewer side effects than compounds currently used to treat these conditions.

DETAILED DESCRIPTION OF THE INVENTION

As used herein, alkyl groups include straight chained or branched $C_1$–$C_6$ hydrocarbons, which are completely saturated.

As used herein the term "acid bioisosteres" has the meaning known to the artisan and means one substituent which is a bioisostere and includes, for example tetrazole, 3-hydroxyisoxazole, 3-hydroxyisothazole, hydroxyihiadiazole, 3-hydroxy-γ-pyrones, and acylsulphonamide.

Substituted $(CH_2)_a$ means that from one to four available hydrogens of the $CH_2$ are independently replaced with a substituent selected from the group consisting of $C_1$–$C_4$ alkyl, benzyl, and $C_1$–$C_4$ haloalkyl.

Cycloalkyl groups, as used herein, include $C_3$–$C_8$ hydrocarbons, which are completely saturated.

As used herein, aryl groups include carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl).

Heteroaryl groups, as used herein, is an aromatic ring system having at least one heteroatom such as nitrogen, sulfur or oxygen. Heteroaryl groups include thienyl (also referred to herein as "thiophenyl"), pyridyl, pyrrolyl, benzofuranyl isoxazolyl, and pyrimidinyl.

An aryl-C1–C6-alkyl group, as used herein, is an aryl substituent that is linked to a compound by an alkyl group having from one to six carbon atoms.

A heteroaryl-C1–C6-alkyl group, as used herein, is a heteroaryl substituent that is linked to a compound by an alkyl group having from one to six carbon atoms.

A cycloalkyl-C1–C4-alkyl group, as used herein, is a cycloalkyl substituent that is linked to a compound by an alkyl group having from one to four carbon atoms.

An aminoalkyl group is an alkyl group having from one to six carbon atoms which is substituted with at least one amine represented by —$NR_{15}R_{16}$, in which $R_{15}$ and $R_{16}$ are each, independently, a C1–C6 alkyl or $R_{15}$ and $R_{16}$ taken together with the nitrogen to which they are attached form a five or six membered heterocycloalkyl.

Substituents for an aryl or a heteroaryl group include halo; a carboxylic acid group; C1–C6 alkoxy; nitro; cyano; CHO; hydroxyl; a C1–C6 alkyl; a C1–C6 alkyl substituted with a carboxylic acid group; —$C(O)NR_{10}R_{11}$, in which $R_{10}$ and $R_{11}$ are each, independently, H or a C1–C4 alkyl; and a C1–C6 alkyl substituted with one or more halo.

As described herein R14, aryl, heteroaryl substituents are independently selected from the group consisting, H, a C1–C4 alkyl, a C1–C4 alkoxy, a halo, C1–C4 haloalkyl, C1–C4 haloalkoxy, or a cycloalkyl, and up to two selected from the group consisting of H, a C1–C4 alkyl, a C1–C4 alkoxy, a halo, C1–C4 haloalkyl, C1–C4 haloalkoxy, a cycloalkyl, Heterocyclic or each $R_8$ taken together with the phenyl to which they are attached are benzodioxolyl.

Heterocyclic represents an unsubstituted or substituted 5–6 membered monocyclic, or 8–10 membered bicyclic heterocyclic ring and that consists of carbon atoms and from 1 to 3 heteroatoms selected from the group consisting of N, O, or S. It also includes a bicyclic group in which any of the above-defined heterocyclic rings is fused to a benzene ring. The heterocyclic ring may be attached at any heteroatom or carbon atom that affords a stable structure. Such Heterocyclic can be optionally substituted with 1 to 5 substituents selected from the group consisting of hydrogen, halo, nitro, cyano, C1–C6 alkyl, C1–C6 alkoxy, C3–C10 cycloalkyl, trifluoromethyl, substituted phenyl, phenoxy.

Some preferred Heterocyclic are, for example, oxazolyl, isoxazolyl, thiazolyl, imidazolyl, furanyl, thiophenyl, pyridyl, pyrimidinyl, pyridazinyl, triazinyl, indolyl, benzofuranyl, benzothiophenyl, quinolinyl, isoquinolinyl, benzimidazolyl, benzothiazolyl, benzooxazolyl, tetrahydrofuryl, tetrahydropyranyl, tetrahydroquinolyl, tetrahydroisoquinolyl.

In a preferred embodiment, the compounds of the present invention, separately or with their respective pharmaceutical compositions, have n is 2 as represented by Structural Formula II:

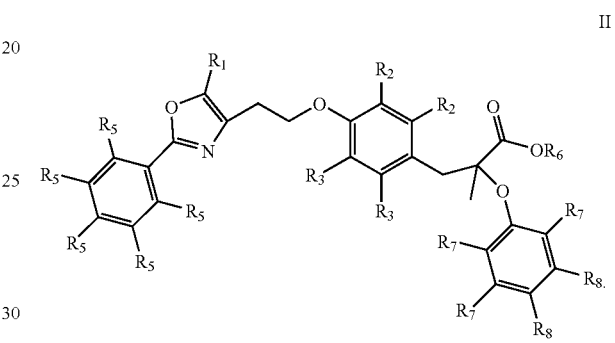

II

In Structural Formula II, $R_1$, $R_2$, $R_3$, $R_5$, $R_6$, $R_7$ and $R_8$ are as defined for Structural Formula I.

In a more preferred embodiment, the compounds of the present invention, and their respective pharmaceutical compositions, have n equal to 2 and an oxazole ring which is substituted with a biphenyl group as represented by Structural Formula III.

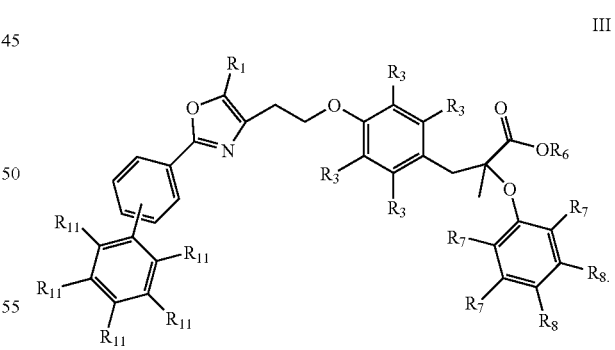

III

In Structural Formula III, $R_1$, $R_3$, $R_6$, $R_7$ and $R_8$ are as defined for Structural Formula I, and each $R_{11}$ is, independently, H, a halo, a C1–C4 alkyl, or a C1–C4 alkoxy.

In another preferred embodiment, the compounds of the present invention, and their respective pharmaceutical compositions, have n equal to 2 and an oxazole ring which is substituted with a thienylphenyl as represented by Structural Formula IV.

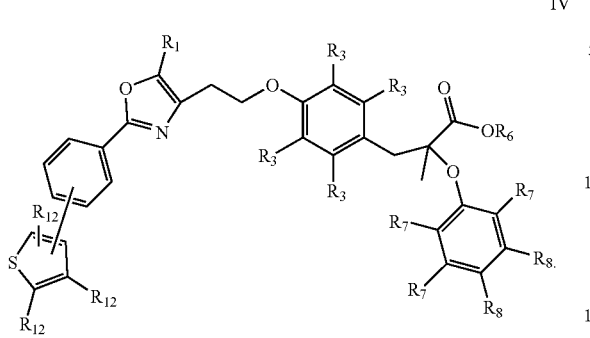

IV

In Structural Formula IV, $R_1$, $R_3$, $R_6$, $R_7$ and $R_8$ are as defined for Structural Formula I, and each $R_{12}$ is, independenty H, a halo, a C1–C4 alkyl or a C1–C4 alkoxy.

In another preferred embodiment, the compounds of the present invention, and their respective pharmaceutical compositions, have n equal to 2 and each $R_2$ taken together with the phenyl ring to which they are attached is a naphthyl. This embodiment can be represented by Structural Formula V.

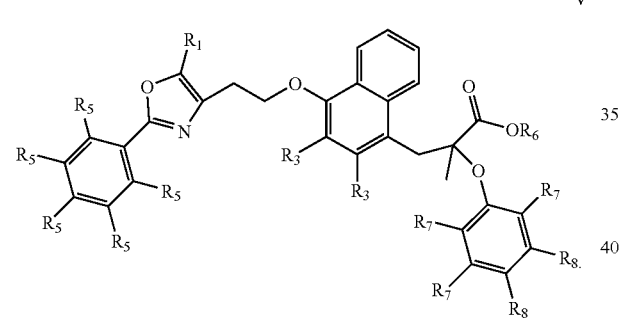

V

In Structural Formula V, $R_1$, $R_3$, $R_5$, $R_6$, $R_7$ and $R_8$ are as defined for Structural Formula I.

$R_1$ is preferably methyl or trifluoromethyl in the compounds represented by Structural Formulas I, II, III, IV, V, VI, VII, VIII, IX, and X.

$R_2$ and $R_3$ in Structural Formulas I, II, III, IV, VII, IX and X are preferably, independently, selected from the following group: H, C1–C6 alkyl, and C1–C4 alkoxy. More preferably $R_2$ and $R_3$ in Structural Formulas I, I, II, IV, VIII, IX and X are, independently, selected from H, propyl and methoxy.

Preferably, $R_4$ is selected from the following group: methyl, ethyl, and butyl in compounds represented by Structural Formulas I, II, III, IV, V, VI, VII, VIII, IX, and X. More preferably, $R_4$ is methyl in compounds represented by Structural Formulas I, II, III, IV, V, VI, VII, VIII, IX, and X.

In one embodiment, the phenyl substituent of the oxazole ring of Structural Formulas I, II, V and VIII together with its $R_5$ substituents or the biphenyl group of Structural Formulas III, VI, and IX together with its $R_{11}$ substituents can be selected from the following group:

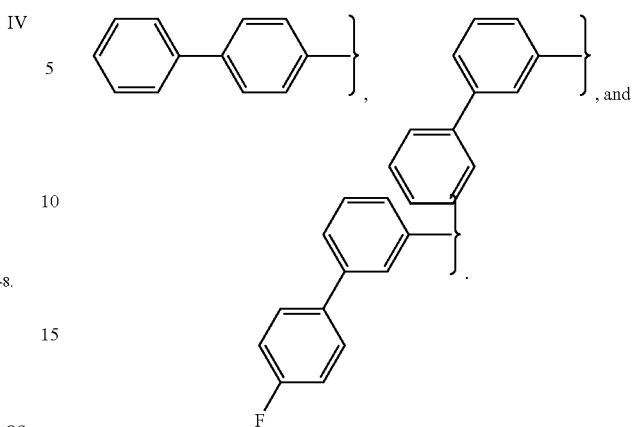

In another embodiment, the phenyl substituent of the oxazole ring of Structural Formulas I, II, V and VIII together with its $R_5$ substituents or the thiophenylphenyl group of Structural Formulas IV, VI, and X together with its $R_{12}$ substitutents can be selected from the following group:

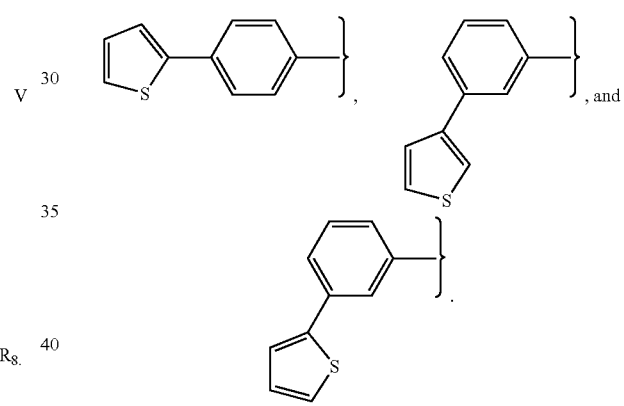

The phenoxy substituent together with its $R_7$ and $R_8$ substitutents is preferably selected from the following group:

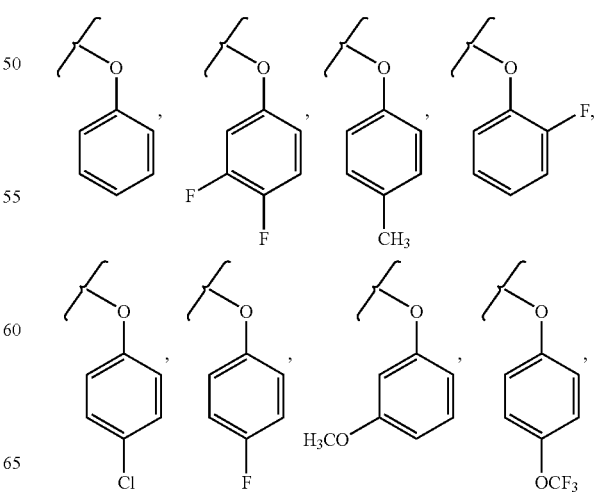

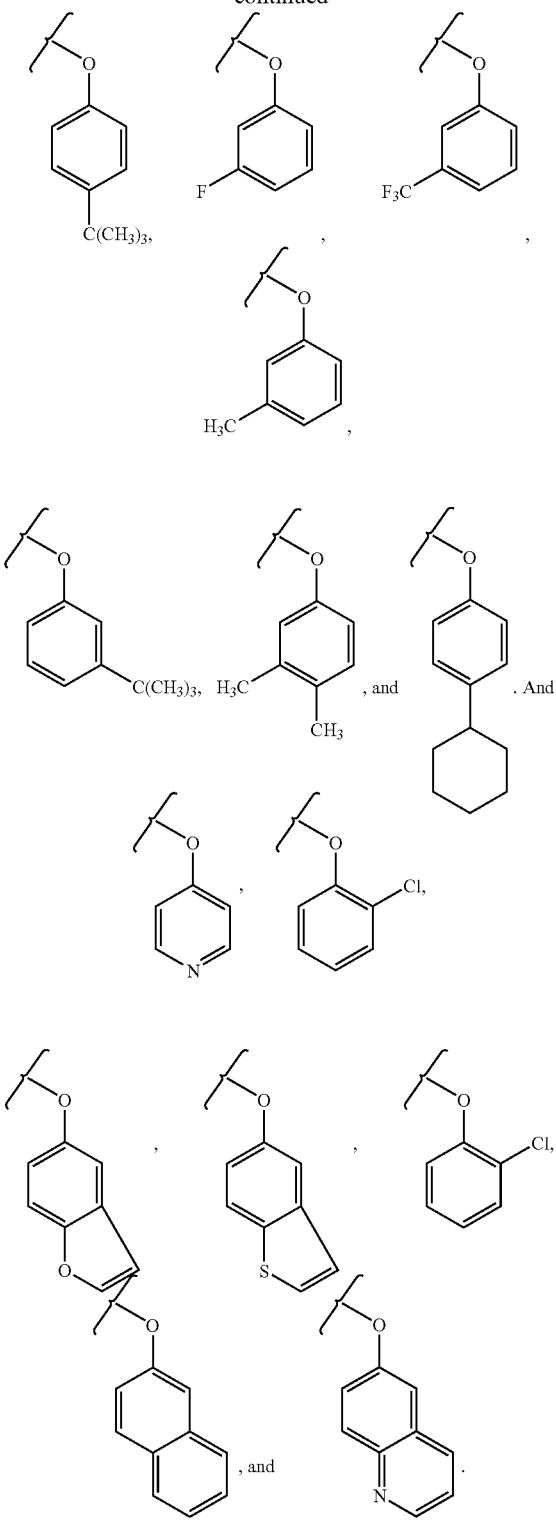

Preferably, $R_7$ and $R_8$ are H.

In a particularly preferred embodiment, the compound is selected from the following group:

3-{4-[2-(2-Biphenyl-4-yl-5-methyloxazol-4-yl)ethoxy]-phenyl}-2-methyl-2-phenoxypropionic acid;

3-{4-[2-(2-Biphenyl-3-yl-5-methyl-oxazol-4-yl)ethoxy]-phenyl}-2-methyl-2-phenoxypropionic acid;

2-Methyl-3-(4-{2-[5-methyl-2-(4-thiophen-2-yl-phenyl)-oxazol-4-yl]-ethoxy}-phenyl)-2-phenoxypropionic acid;

3-(4-{2-[2-(4'-Fluorobiphenyl-3-yl)-5-methyloxazol-4-yl]ethoxy}phenyl)-2-methyl-2-phenoxypropionic acid;

2-Methyl-3-(4-{2-[5-methyl-2-(3-thiophen-2-ylphenyl)oxazol-4-yl]ethoxy}phenyl)-2-phenoxypropionic acid;

2-Methyl-3-(4-{2-[5-methyl-2-(3-thiophen-3-ylphenyl)oxazol-4-yl]ethoxy}phenyl)-2-phenoxypropionic acid;

3-{4-[2-(2-Biphenyl-4-yl-5-methyloxazol-4-yl)ethoxy]-3-methoxyphenyl}-2-methyl-2-phenoxypropionic acid;

3-{4-[2-(2-Biphenyl-3-yl-5-methyloxazol-4-yl)ethoxy]-3-methoxyphenyl}-2-methyl-2-phenoxypropionic acid;

3-(3-Methoxy-4-{2-[5-methyl-2-(4-thiophen-2-ylphenyl)oxazol-4-yl]ethoxy}phenyl)-2-methyl-2-phenoxypropionic acid;

3-{4-[2-(2-Biphenyl-3-yl-5-methyl-oxazol-4-yl)-ethoxy]-3-propyl-phenyl}-2-methyl-2-phenoxy-propionic acid;

2-Methyl-3-(4-{2-[5-methyl-2-(4-thiophen-2-yl-phenyl)-oxazol-4-yl]-ethoxy}-3-propyl-phenyl)-2-phenoxy-propionic acid;

3-{4-[2-(2-Biphenyl-4-yl-5-methyl-oxazol-4-yl)-ethoxy]-naphthalen-1-yl}-2-methyl-2-phenoxypropionic acid;

3-{4-[2-(2-Biphenyl-3-yl-5-methyl-oxazol-4-yl)-ethoxy]-naphthalen-1-yl}-2-methyl-2-phenoxypropionic acid;

2-Methyl-3-(4-{2-[5-methyl-2-(4-thiophen-2-yl-phenyl)-oxazol-4-yl]-ethoxy}-naphthalen-1-yl)-2-phenoxypropionic acid;

3-{4-[2-(2-Biphenyl-4-yl-5-methyl-oxazol-4-yl)-ethoxy]-phenyl}-2-methyl-2-(4-tert-butylphenoxy)-propionic acid;

3-{4-[2-(2-Biphenyl-3-yl-5-methyl-oxazol-4-yl)-ethoxy]-phenyl}-2-methyl-2-(4-tert-butylphenoxy)-propionic acid;

2-Methyl-3-(4-{2-[5-methyl-2-(4-thiophen-2-yl-phenyl)-oxazol-4-yl]-ethoxy}-phenyl)-2-(4-tert-butylphenoxy)-propionic acid;

2-Methyl-3-(4-{2-[5-methyl-2-(3-thiophen-2-yl-phenyl)-oxazol-4-yl]-ethoxy}-phenyl)-2-(4-tert-butylphenoxy)-propionic acid;

2-Methyl-3-(4-{2-[5-methyl-2-(3-thiophen-3-yl-phenyl)-oxazol-4-yl]-ethoxy}-phenyl)-2-(4-tert-butylphenoxy)-propionic acid;

3-{4-[2-(2-Biphenyl-3-yl-5-methyl-oxazol-4-yl)-ethoxy]-phenyl}-2-(3-fluoro-phenoxy)-2-methyl-propionic acid;

3-{4-[2-(2-Biphenyl-4-yl-5-methyl-oxazol-4-yl)-ethoxy]-phenyl}-2-(3-fluoro-phenoxy)-2-methyl-propionic acid;

2-(3-Fluoro-phenoxy)-2-methyl-3-(4-{2-[5-methyl-2-(4-thiophen-2-yl-phenyl)-oxazol-4-y]-ethoxy}-phenyl)-propionic acid;

3-{4-[2-(2-Biphenyl-4-yl-5-methyl-oxazol-4-yl)-ethoxy]-phenyl}-2-(3-tert-butyl-phenoxy)-2-methyl-propionic acid;

2-(3-tert-Butyl-phenoxy)-2-methyl-3-(4-{2-[5-methyl-2-(4-thiophen-2-yl-phenyl)-oxazol-4-yl]-ethoxy}-phenyl)-propionic acid;

2-(2-Fluoro-phenoxy)-2-methyl-3-(4-{2-[5-methyl-2-(4-thiophen-2-yl-phenyl)-oxazol-4-yl]-ethoxy}-phenyl)-propionic acid;

2-(4-Chlorophenoxy)-2-methyl-3-(4-{2-[5-methyl-2-(3-thiophen-2-yl-phenyl)-oxazol-4-yl]-ethoxy}-phenyl)-propionic acid;

3-{4-[2-(2-Biphenyl-4-yl-5-methyl-oxazol-4-yl)-ethoxy]-phenyl}-2-(4-chloro-phenoxy)-2-methyl-propionic acid;

3-{4-[2-(2-Biphenyl-3-yl-5-methyl-oxazol-4-yl)-ethoxy]-phenyl}-2-(4-chloro-phenoxy)-2-methyl-propionic acid;

2-(4-Cyclohexyl-phenoxy)-2-methyl-3-(4-{2-[5-methyl-2-(3-thiophen-2-yl-phenyl)-oxazol-4-yl]-ethoxy}-phenyl)-propionic acid;

3-{4-[2-(2-Biphenyl-4-yl-5-methyl-oxazol-4-yl)-ethoxy]-phenyl}-2-(4-cyclohexyl-phenoxy)-2-methyl-propionic acid;

3-{4-[2-(2-Biphenyl-3-yl-5-methyl-oxazol-4-yl)-ethoxy]-phenyl}-2-(4-cyclohexyl-phenoxy)-2-methyl-propionic acid;

2-(3,4-Dimethyl-phenoxy)-2-methyl-3-(4-{2-[5-methyl-2-(4-thiophen-2-yl-phenyl)-oxazol-4-yl]-ethoxy}-phenyl)-propionic acid;

3-{4-[2-(2-Biphenyl-4-yl-5-methyl-oxazol-4-yl)-ethoxy]-phenyl}-2-(3,4-dimethyl-phenoxy)-2-methyl-propionic acid;

3-{4-[2-(2-Biphenyl-4-yl-5-methyl-oxazol-4-yl)-ethoxy]-phenyl}-2-(3,4-dimethyl-phenoxy)-2-methyl-propionic acid;

(R)-2-Methyl-3-(4-{2-[5-methyl-2-(4-thiophen-2-yl-phenyl)-oxazol-4-yl]-ethoxy}-phenyl)-2-p-tolyloxy-propionic acid;

(R)-3-{4-[2-(2-Biphenyl-4-yl-5-methyl-oxazol-4-yl)-ethoxy]-phenyl}-2-methyl-2-p-tolyloxy-propionic acid;

3-{4-[2-(2-Biphenyl-4-yl-5-methyl-oxazol-4-yl)-ethoxy]-phenyl}-2-methyl-2-(4-trifluoromethoxy-phenoxy)-propionic acid;

3-{4-[2-(2-Biphenyl-3-yl-5-methyl-oxazol-4-yl)-ethoxy]-phenyl}-2-methyl-2-(4-trifluoromethoxy-phenoxy)-propionic acid;

2-Methyl-3-(4-{2-[5-methyl-2-(4-thiophon-2-yl-phenyl)-oxazol-4-yl]-ethoxy}-phenyl)-2-(4-trifluoromethoxy-phenoxy)-propionic acid;

2-{4-[2-(2-Biphenyl-4-yl-5-methyl-oxazol-4-yl)-ethoxy]-benzyl}-2-phenoxy-butyric acid;

2-{4-[2-(2-Biphenyl-3-yl-5-methyl-oxazol-4-yl)-ethoxy]-benzyl}-2-phenoxy-butyric acid;

2-(4-{2-[5-Methyl-2-(3-thiophen-2-yl-phenyl)-oxazol-4-yl]-ethoxy}-benzyl)-2-phenoxy-butyric acid;

3-{4-[2-(2-Biphenyl-4-yl-5-methyl-oxazol-4-yl)-ethoxy]-phenyl}-2-methyl-2-(4-trifluoromethyl-phenoxy)-propionic acid;

2-Methyl-3-(4-{2-[5-methyl-2-(4-thiophen-2-yl-phenyl)-oxazol-4-yl]-ethoxy}-phenyl)-2-(4-trifluoromethyl-phenoxy)-propionic acid;

3-{4-[2-(2-Biphenyl-4-yl-5-methyl-oxazol-4-yl)ethoxy]-phenyl}-2-(3,4-difluoro-phenoxy)-2-methyl-propionic acid;

3-{4-[2-(2-Biphenyl-3-yl-5-methyl-oxazol-4-yl)ethoxy]-phenyl}-2-(3,4-difluoro-phenoxy)-2-methyl-propionic acid;

2-(3,4-Difluoro-phenoxy)-2-methyl-3-(4-{2-[5-methyl-2-(4-thiophen-2-yl-phenyl)-oxazol-4-yl]-ethoxy}-phenyl)-propionic acid;

3-{4-[2-(2-Biphenyl-3-yl-5-methyl-oxazol-4-yl)-ethoxy]-phenyl}-2-methyl-2-m-tolyloxy-propionic acid;

3-{4-[2-(2-Biphenyl-4-yl-5-methyl-oxazol-4-yl)-ethoxy]-phenyl}-2-methyl-2-m-tolyloxy-propionic acid;

2-Methyl-3-(4-{2-[5-methyl-2-(4-thiophen-2-yl-phenyl)-oxazol-4-yl]-ethoxy}-phenyl)-2-m-tolyloxy-propionic acid;

3-{4-[2-(2-Biphenyl-3-yl-5-methyl-oxazol-4-yl)-ethoxy]-phenyl}-2-(4-fluoro-phenoxy)-2-methyl-propionic acid;

3-{4-[2-(2-Biphenyl-4-yl-5-methyl-oxazol-4-yl)-ethoxy]-phenyl}-2-(4-fluoro-phenoxy)-2-methyl-propionic acid;

2-(4-Fluoro-phenoxy)-2-methyl-3-(4-{2-[5-methyl-2-(4-thiophen-2-yl-phenyl)-oxazol-4-yl]-ethoxy}-phenyl)-propionic acid;

2-Methyl-3-(4-{2-[5-methyl-2-(4-thiophen-2-yl-phenyl)-oxazol-4-yl]-ethoxy}-phenyl)-2-(3-trifluoromethyl-phenoxy)-propionic acid;

3-{4-[2-(2-Biphenyl-3-yl-5-methyl-oxazol-4-yl)-ethoxy]-phenyl}-2-(3-methoxy-phenoxy)-2-methyl-propionic acid;

3-{4-[2-(2-Biphenyl-4-yl-5-methyl-oxazol-4-yl)-ethoxy]-phenyl}-2-(3-methoxy-phenoxy)-2-methyl-propionic acid;

2-(3-Methoxy-phenoxy)-2-methyl-3-(4-{2-[5-methyl-2-(4-thiophen-2-yl-phenyl)-oxazol-4-yl]-ethoxy}-phenyl)-propionic acid;

2-(Benzo[1,3]dioxol-5-yloxy)-3-{4-[2-(2-biphenyl-3-yl-5-methyl-oxazol-4-yl)-ethoxy]-phenyl}-2-methyl-propionic acid;

2-(Benzo[1,3]dioxol-5-yloxy)-3-{4-[2-(2-biphenyl-4-yl-5-methyl-oxazol-4-yl)-ethoxy]-phenyl}-2-methyl-propionic acid;

2-(Benzo[1,3]dioxol-5-yloxy)-2-methyl-3-(4-{2-[5-methyl-2-(3-thiophen-2-yl-phenyl)-oxazol-4-yl]-ethoxy}-phenyl)-propionic acid;

2-{4-[2-(2-Biphenyl-4-yl-5-methyl-oxazol-4-yl)-ethoxy]-benzyl}-2-phenoxy-hexanoic acid;

2-{4-[2-(2-Biphenyl-3-yl-5-methyl-oxazol-4-yl)-ethoxy]-benzyl}-2-phenoxy-hexanoic acid;

2-(4-{2-[5-Methyl-2-(3-thiophen-2-yl-phenyl)-oxazol-4-yl]-ethoxy}-benzyl)-2-phenoxy-hexanoic acid; and (R)-3-{4-[2-(2-Biphenyl-3-yl-5-methyl-oxazol-4-yl)-ethoxy]-phenyl}-2-methyl-2-p-tolyloxy-propionic acid.

Prodrugs are compounds of the present invention, which have chemically or metabolically cleavable groups and become by solvolysis or under physiological conditions the compounds of the invention which are pharmaceutically active in vivo. Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as is (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

Methyl ester prodrugs may be prepared by reaction of the acid form of a compound of formula I in a medium such as methanol with an acid or base esterification catalyst (e.g., NaOH, H₂SO₄). Ethyl ester prodrugs are prepared in similar fashion using ethanol in place of methanol.

Morpholinylethyl ester prodrugs may be prepared by reaction of the sodium salt of a compound of Structural Formula I (in a medium such as dimethylformamide) with 4-(2-chloroethyl)morphine hydrochloride (available from Aldrich Chemical Co., Milwaukee, Wis. USA, Item No. C4,220-3).

The term "pharmaceutically acceptable" means that the carrier, diluent, excipients and salt must be compatible with the other ingredients of the formulation, and not deleterious to the recipient thereof. Pharmaceutical formulations of the present invention are prepared by procedures known in the art using well known and readily available ingredients.

"Effective amount" means an amount of compound according to Structural Formula I, in any polymorphic form, or a salt thereof that is capable of producing its intended effect.

"Preventing" refers to reducing the likelihood that the recipient will incur or develop any of the pathological conditions described herein.

By virtue of its acidic moiety, a compound of Structural Formula I forms salts with pharmaceutically acceptable bases. Such a pharmaceutically acceptable salt may be made with a base which affords a pharmaceutically acceptable cation, which includes alkali metal salts (especially sodium and potassium), alkali earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bisdehydroabietylamine, glucamine, N-methylglucamine, collidine, quinine, quinoline, and basic amino acid such as lysine and arginine. These salts may be prepared by methods known to those skilled in the art.

Compounds of Structural Formula I, which are substituted with a basic group, may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [e.g. (+)-tarates, (−)-tartrates or mixtures thereof including racemic mixtures], succinates, benzoates and salts with amino acids such as glutamic acid.

Certain compounds of Structural Formula I and their salts may also exist in the form of solvates, for example hydrates, and the present invention includes each solvate and mixtures thereof.

The compounds of Structural Formula I contain one or more chiral centers, and exist in different optically active forms. When compounds of Structural Formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound represented by Structural Formula I has one or more chiral substituent it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

Certain compounds of Structural Formula I and their salts may exist in more than one crystal form. Polymorphs of compounds represented by Structural Formula I form part of this invention and may be prepared by crystallization of a compound of Structural Formula I under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of Structural Formula I followed by gradual or fast cooling. The presence of polymorphs may be determined by solid probe nmr spectroscopy, ir spectroscopy, differential scanning calorimetry, powder X-ray diffraction or such other techniques.

The language a "therapeutically effective amount" or "pharmaceutically effective amount" is intended to include an amount which is sufficient to mediate a disease or condition and prevent its further progression or ameliorate the symptoms associated with the disease or condition. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a PPAR receptor, such as a PPARγ or PPARα receptor, which mediate a disease or condition. Conditions mediated by PPARα or PPARγ receptors include diabetes mehitus, cardiovascular disease, Syndrome X, obesity and gastrointestinal disease.

The compounds of Structural Formula I, and the pharmaceutically acceptable salts, solvates and hydrates thereof, have valuable pharmacological properties and can be used in pharmaceutical preparations containing the compound or pharmaceutically acceptable salts, esters or prodrugs thereof, in combination with a pharmaceutically acceptable carrier or diluent. They are useful as therapeutic substances in preventing or treating Syndrome X, diabetes mellitus and related endocrine and cardiovascular disorders and diseases in human or non-human animals. Suitable pharmaceutically acceptable carriers include inert solid fillers or diluents and sterile aqueous or organic solutions. The active compound will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19th edition, Mack Publishing Co., Easton, Pa. (1995).

For oral administration, the compound or salts thereof can be combined with a suitable solid or liquid carrier or diluent to form capsules, tablets, pills, powders, syrups, solutions, suspensions and the like.

The tablets, pills, capsules, and the like may also contain a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained.

The active compounds can also be administered intranasally as, for example, liquid drops or spray. For oral or nasal inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

For parental administration the compounds of the present invention, or salts thereof can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, ethanol, polyol (e.g. glycerol, propylene glycol and liquid polyethylene glycol), propylene glycol and liquid polyethylene glycol), suitable mixtures thereof, and vegetable oils. The injectable solutions prepared in this manner can then be administered intravenously, intraperitoneally, subcutaneously, or intramuscularly, with intramuscular administration being preferred in humans.

The compounds may also be formulated in rectal compositions such as suppositories or retention enemas, e.g., containing conventional suppository bases such as cocoa butter or other glycerides.

In addition, to the formulations described previously, the compounds may also be formulated as a depot preparation. Such long acting formulations may be administered by implantation, for example, subcutaneously or intramuscularly or by intramuscular injection. Thus, for example, as an emulsion in an acceptable oil, or ion exchange resins, or as sparingly soluble derivatives, for example, as sparingly soluble salts.

The effective dosage of active ingredient employed may vary depending on the particular compound employed, the mode of administration, the condition being treated and the severity of the condition being treated.

When used herein Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage formulation which contains a compound of Structural Formula I and one or more additional active agents, as well as administration of a compound of Structural Formula I and each active agent in its own separate pharmaceutical dosage formulation. For example, a compound of Structural Formula I or thereof and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, a compound of Structural Formula I and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein a compound of Structural Formula I or salts thereof is administered in combination with one or more of the following active agents: antihyperlipidemic agents; plasma HDL-raising agents; antihypercholesterolemic agents, fibrates, vitamins, aspirin, and the like. As noted above, the compounds of Structural Formula I can be administered in combination with more than one additional active agent.

Another example of combination therapy can be seen in treating diabetes and related disorders wherein the compounds of Structural Formula I, salts thereof can be effectively used in combination with, for example, sulfonylureas, biguanides, thiazolidinediones, α-glucosidase inhibitors, other insulin secretogogues, insulin as well as the active agents discussed above for treating atherosclerosis.

A therapeutically effective amount of a compound of Structural Formula I can be used for the preparation of a medicament useful for treating Syndrome X, diabetes, treating obesity, lowering tryglyceride levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of Structural Formula I (1) reduces serum glucose levels of a patient, or more specifically HbA1c, typically by about 0.7%;

(2) reduces the serum triglyceride levels of a patient, typically by about 20%; and/or (3) increases the serum HDL levels in a patient, preferably by about 30%.

Additionally, an effective amount of a compound of Structural Formula I and a therapeutically effective amount of one or more active agents selected from a group consisting of: antihyperlipidemic agent, plasma HDL-raising agents, antihypercholesterolemic agents, fibrates, vitamins, aspirin, insulin secretogogues, insulin and the like can be used together for the preparation of a medicament useful for the above-described treatments.

Preferably compounds of the invention or pharmaceutical formulations containing these compounds are in unit dosage form for administration to a mammal. The unit dosage form can be any unit dosage form known in the art including, for example, a capsule, an IV bag, a tablet, or a vial. The quantity of active ingredient (viz., a compound of Structural Formula I or salts thereof) in a unit dose of composition is a therapeutically effective amount and may be varied according to the particular treatment involved. It may be appreciated that it may be necessary to make routine variations to the dosage depending on the age and condition of the patient. The dosage will also depend on the route of administration which may be by a variety of routes including oral, aerosol, rectal, transdermal, subcutaneous, intravenous, intramuscular, intraperitoneal and intranasal.

Pharmaceutical formulations of the invention are prepared by combining (e.g., mixing) a therapeutically effective amount of a compound of the invention together with a pharmaceutically acceptable carrier or diluent. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of about 0.05 to about 5.0 mg/ml in a 4% dextrose/0.5% Na citrate aqueous solution.

Solid form formulations include powders, tablets and capsules. A solid carrier can be one or more substance which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

Powders and tablets preferably contain from about 1 to about 99 weight percent of the active ingredient which is the novel compound of this invention. Suitable solid carriers are magnesium carbonate, magnesium stearate, talc, sugar, lactose, pectin, dextrin, starch, gelatin, tragacanth, methyl cellulose, sodium carboxymethyl cellulose, low melting waxes, and cocoa butter.

The following pharmaceutical formulations 1 through 8 are illustrative only and are not intended to limit the scope of the invention in any way. "Active Ingredient", refers to a compound according to Structural Formula I or salts thereof.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
|---|---|
| Active Ingredient | 0.25 |
| Ethanol | 25.75 |
| Propellant 22 (Chlorodifluoromethane) | 74.00 |
| Total | 100.00 |

The Active Ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| Active Ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active Ingredient, are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active Ingredient, are made as follows:

| Active Ingredient | 225 mg |
|---|---|
| Saturated fatty acid glycerides | 2,000 mg |
| Total | 2,225 mg |

The Active Ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active Ingredient per 5 ml dose, are made as follows:

| Active Ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active Ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active Ingredient | 100 mg |
|---|---|
| Isotonic saline | 1,000 ml |

The solution of the above materials generally is administered intravenously to a subject at a rate of 1 ml per minute.

Synthesis

Compounds in which the five membered ring is an oxazole have been synthesized by three routes. Two of the synthetic routes rely on 2-(bromophenyl)-4-(2-hydroxyethyl-5-substituted-oxazole intermediate (Structural Formula XVII), the synthesis of which is depicted in Scheme I.

The first step of the synthesis of the 2-(bromophenyl)-4-(2-hydroxyethyl)-5-substituted-oxazole intermediate is a condensation of a dionemonooxime represented by Structural Formula XI with a bromobenzaldehyde represented by Structural Formula XII in the presence of an acid such as aqueous concentrated hydrochloric acid or, preferably, acetic acid which is saturated with hydrogen chloride gas. Typically, hydrogen chloride is bubbled through a solution of the dionemonooxime and the bromobenzaldehyde in acetic acid, which is held at a constant temperature of about −20° C. to about 20° C. for about 15 minutes to about 1 hour. The product of the condensation is an oxazole N-oxide represented by Structural Formula XIII.

The oxazole N-oxide is then treated with phosphorous oxychloride in an inert solvent such as dichloromethane or chloroform to form a 2-(bromophenyl)-4-chloromethyl-5-substituted-oxazole represented by Structural Formula XIV. The reaction typically is carried out at the reflux temperature of the solvent used and is complete in about 15 minutes to about 1 hour.

The 2-(bromophenyl)-4-chloromethyl-5-substituted-oxazole is then treated with a cyanide and an iodide salt to form a 2-(bromophenyl)-4-cyanomethyl-5-substituted-oxazole represented by Structural Formula XV. The reaction is typically carried out in a polar, aprotic solvent such as dimethylformamide at a temperature of about 30° C. to about 120° C. for about 1 hour to about 6 hours. Preferably, the cyanide and iodide salts are potassium cyanide and potassium iodide.

The cyano group of the a 2-(bromophenyl)-4-cyanomethyl-5-substituted-oxazole is converted to a carboxylic acid group by treatment with a alkali metal hydroxide to form a 2-(bromophenyl)-4-carboxymethyl-5-substituted-oxazole represented by Structural Formula XVI. The reaction is generally carried out in an aqueous solution at about 80° C. to about 100° C. The concentration of the alkali metal hydroxide in the aqueous solution is typically about 25% to about 85% (weight/volume). Preferably, the alkali metal hydroxide is potassium hydroxide.

The 2-(bromophenyl)-4-carboxymethyl-5-substituted-oxazole is then treated with a carboxylic acid reducing agent, such as borane or lithium aluminum hydride, to form the 2-(bromophenyl)-4-(2-hydroxyethyl)-5-substituted-oxazole intermediate represented by Structural Formula XVII. The reaction is typically carried out under anhydrous conditions in an ether solvent such as tetrahydrofuran (THF), dioxane, or ethyl ether. When borane is the reducing agent used, it typically forms a complex with the ether solvent such as a $BH_3$-THF complex. A solution having a concentration of about 0.5 M to about 1.5 M borane complex in the ether solvent is added dropwise to absolution of 0.1 M to 1.3 M of the 2-(bromophenyl)-4-carboxymethyl-5-substituted-oxazole in the ether solvent. The reaction temperature is about 20° C. to about 40° C. Typically, the reaction is complete in about 1 hour to about 5 hours.

Scheme I: General synthesis of 2-(bromophenyl)-4-(2-hydroxyethyl)-5-substituted oxazoles represented by Strutural Formula XVII.

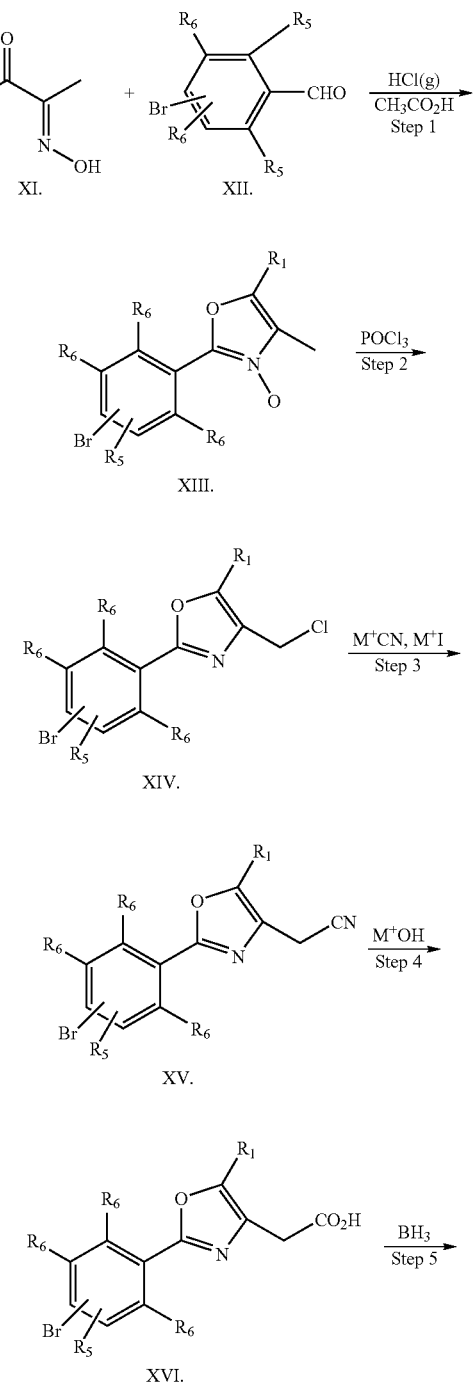

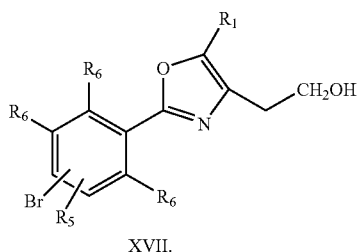

XVII.

In a first synthetic route to prepare compounds represented by Structural Formula I in which the five membered ring is an oxazole ring (see Scheme II), the intermediate represented by Structural Formula XVII can be converted into a 2-(bromophenyl-5-substituted-oxazol-4-yl)ethyl sulfonyl ester represented by Structural Formula XVIII by treatment with a sulfonyl anhydride or a sulfonyl halide such as tosyl anhydride, mesyl anhydride, tosyl chloride or mesyl chloride in the presence of a base (Scheme II, step 1). The reaction is typically carried out in an aprotic solvent such as methylene chloride in the presence of an aprotic base, such as pyridine, and in the presence of a nucleophilic catalyst, such as N,N-dimethylaminopyridine DMAP). The reaction is complete in about 0.5 hours to about 5 hours.

The 2-(bromophenyl-5-substituted-oxazol-4-yl)ethyl sulfonyl ester is then reacted with a phenol represented by Structural Formula XIX in the presence of alkali metal carbonate to form a 3-(4-{2-[2-bromophenyl)-5-substituted-oxazol-4-yl]ethoxy}-phenyl)-2-methyl-2-phenoxy-propanoic acid ester represented by Structural Formula XX (Scheme II, step 2). In Structural Formula XI, $R_2$, $R_3$ and $R_4$ are as previously defined for Structural Formula I, and $R_{10}$ is a C1–C4 alkyl. The reaction is typically carried out in a polar solvent such as an alcohol at about 40° C. to about 70° C. and is allowed to proceed for about 16 hours to about 30 hours. The reactants (i.e., the compounds represented by Structural Formulas XVIII and XIX) are present in about equal molar amounts. The alkali metal carbonate is present in about 20 molar equivalents.

Alternatively, the 2-(bromophenyl-5-substituted-oxazolylethyl sulfonyl ester is then reacted with a phenol represented by Structural Formula XIX in the presence of a hindered base to form a 3-(4-{2-[2-(bromophenyl)-5-substituted-oxazol-4-yl]ethoxy}-phenyl)-2-methyl-2-phenoxy-propanoic acid ester represented by Structural Formula XX (Scheme II, step 2). The reaction is typically carried out in a polar solvent such as an alcohol at about 40° C. to about 70° C. and is allowed to proceed for about 24 hours to about 48 hours. The reactants (i.e., the compounds represented by Structural Formulas XVIII and XIX) are present in about equal molar amounts. The alkali metal carbonate is present in about 20 molar equivalents and is preferably bound to an inert solid support such as polystyrene.

The 3-(4-{2-[2-(bromophenyl)-5-substituted-oxazol-4-yl]ethoxy}-phenyl)-2-methyl-2-phenoxy-propanoic acid ester is then treated with an aryl boronic acid in the presence of triphenylphosphine, palladium acetate and sodium carbonate to form a 3-(4-{2-[2-(arylphenyl)-5-substituted-oxazol-4-yl]ethoxy}-phenyl)-2-methyl-2-phenoxy-propanoic acid ester represented by Structural Formula XXI (Scheme II, step 3). Ar in Structural Formula XXI is a substituted or unsubstituted aryl or a substituted or unsubstituted heteroaryl. Typically, the 3-(4-{2-[2-(bromophenyl)-5-substituted-oxazol-4-yl]ethoxy}-phenyl)-2-methyl-2-phenoxy-propanoic acid ester (compound XX) and the arylboronic acid are present in equal molar amounts, or preferable about 0.1 to 0.5 molar excess of the arylboronic acid. The triphenylphosphine is present in about 1.5 to about 2 equivalents, the palladium acetate is present in about 0.1 to about 0.01 equivalents and the sodium carbonate is present in about 1 equivalent to about 1.5 equivalents with respect to compound XX. The reaction is generally carried out in an alcoholic solvent at about 50° C. to about 100° C. and is allowed to proceed for about 1 hour to about 5 hours. Alternatively, the 3-(4-{2-[2-(bromophenyl)-5-substituted-oxazol-4-yl]ethoxy}-phenyl)-2-methyl-2-phenoxy-propanoic acid ester can be treated with an aryl tributyl tin in the presence of $Pd(PPh_3)_4$ ("Ph" is phenyl) to form 3-(4-{2-[2-(arylphenyl)-5-substituted-oxazol-4-yl]ethoxy}-phenyl)-2-methyl-2-phenoxy-propanoic acid ester ester.

Scheme II:Method 1 for synthesizing compounds represented by Structural Formula XXI.

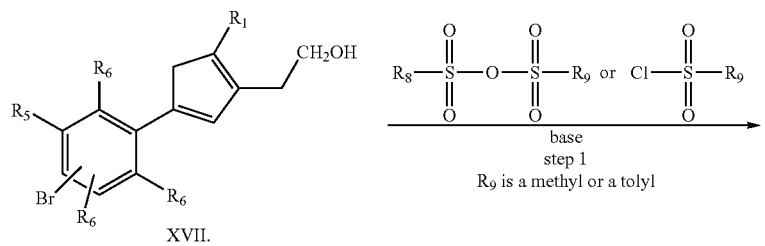

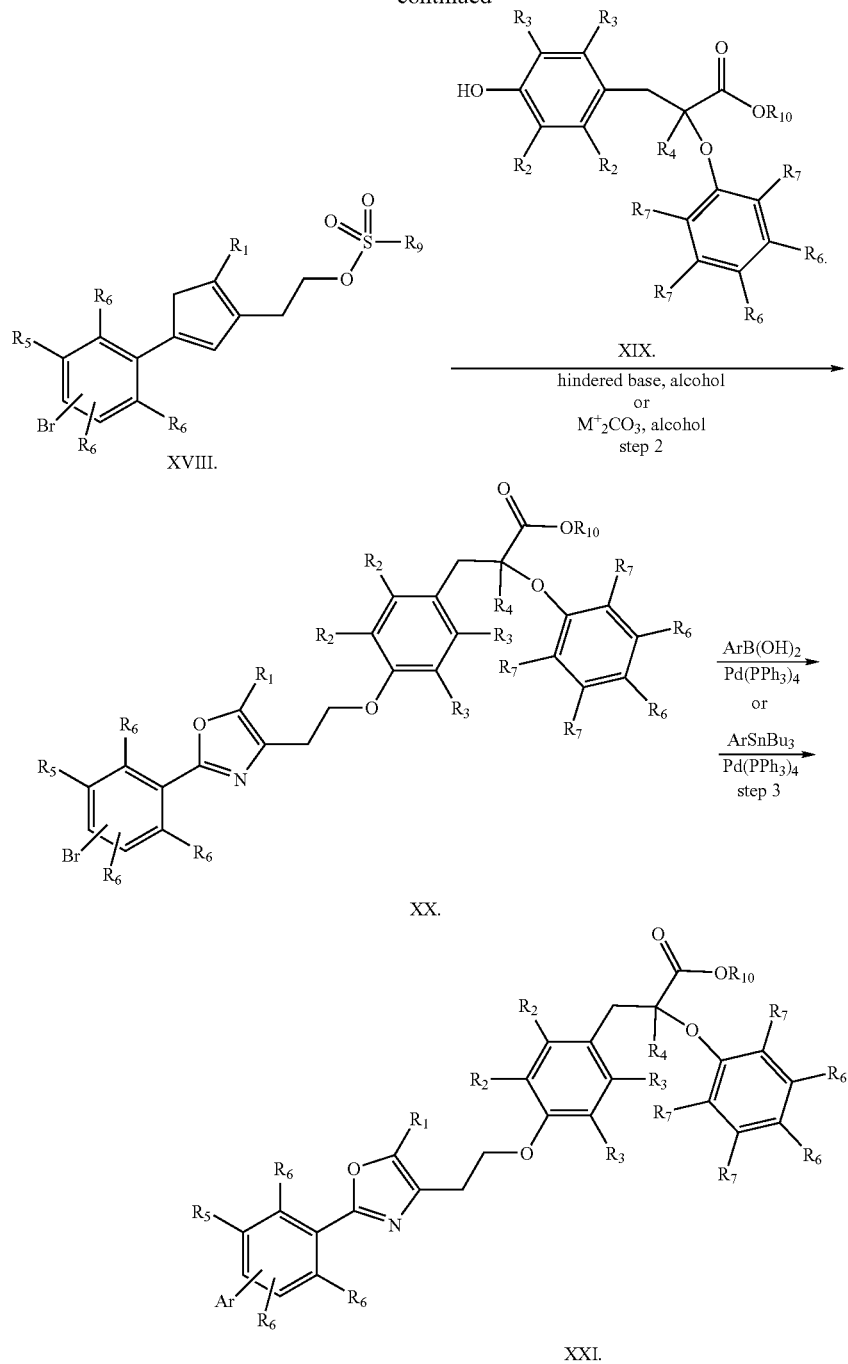

A second method of preparing the compounds represented by Structural Formula I which have an oxazole five membered ring is depicted in Scheme III. The 2-(bromophenyl)-4-(2-hydroxyethyl)-5-substituted oxazole represented by Structural Formula XVII is treated an arylboronic acid in the presence of triphenylphosphine, palladium acetate (or tetrakis(triphenyl(phosphine)palladium(0)) and sodium carbonate to form a 2-(arylphenyl)-4-(2-hydroxyethyl)-5-substituted oxazole represented by Structural Formula XXII. The reaction conditions are the same as those described for step 3 in Scheme II.

The 2-(arylphenyl)-4-(2-hydroxyethyl)-5-substituted oxazole is then treated with a sulfonyl anhydride or a sulfonyl chloride in the presence of a base under conditions as described for step 1 of Scheme II to form a 2-(arylphenyl-5-substituted-oxazol-4-yl)ethyl sulfonyl ester represented by Structural Formula XXIII.

The 2-(arylphenyl-5-substituted-oxazol-4-yl)ethyl sulfonyl ester is then reacted with a phenol represented by Structural Formula XIX in the presence of an alkali metal carbonate or a hindered base under conditions as described for step 2 of Scheme II to form a 3-(4-{2-[2-(arylphenyl)-

5-substituted-oxazol-4-yl]ethoxy)-phenyl)-2-methyl-2-phenoxy-propanoic acid ester represented by Structural Formula XXI.

XXIV is reacted with a phenol represented by compound XXV to form an α-aryloxy ester represented by compound XXVI. This reaction is typically carried out in an anhydrous

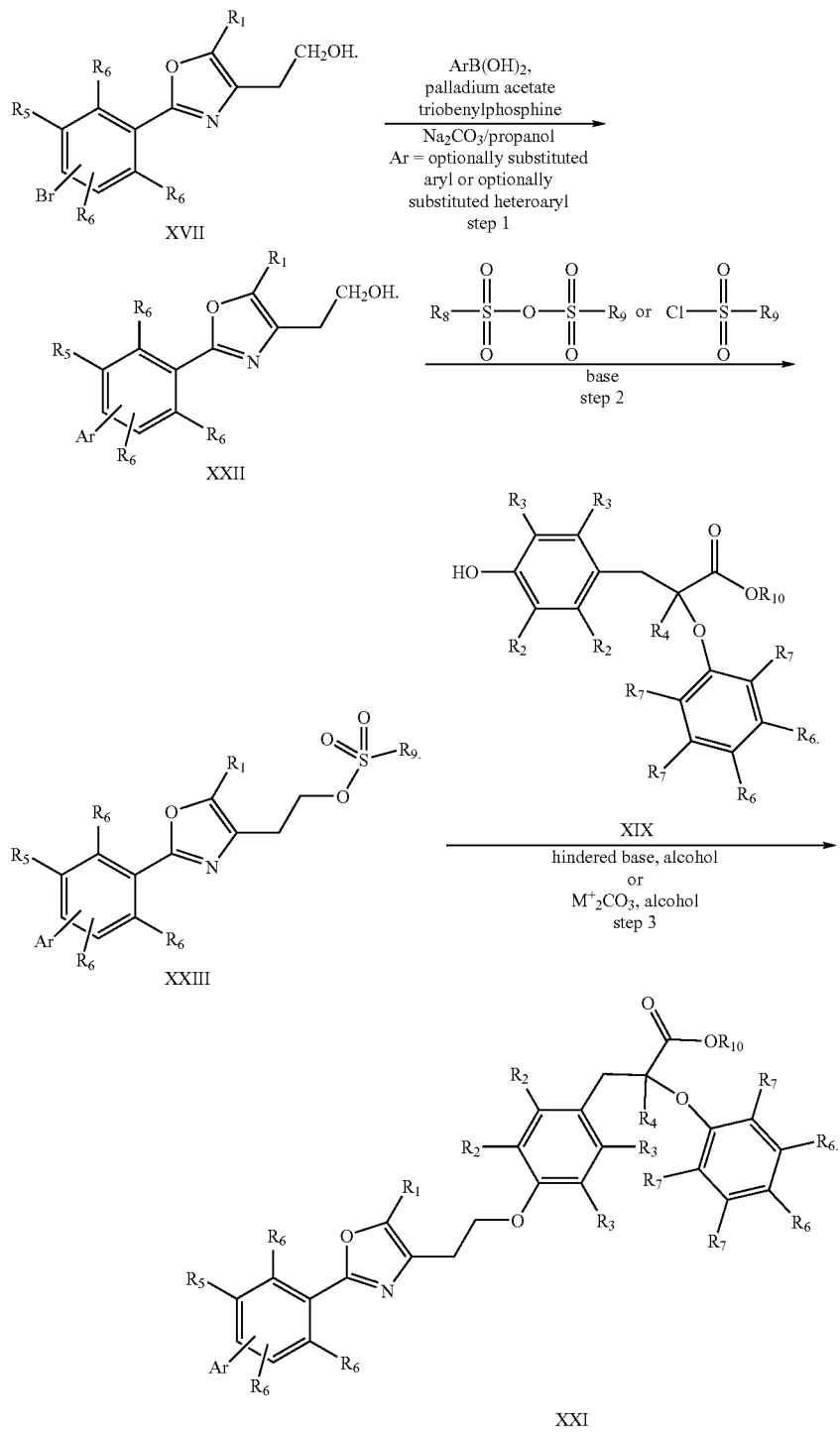

The compound represented by Structural Formula XIX can be prepared by the method depicted in Scheme IV. In this method, an abromoester represented by compound polar solvent such as DMF at a temperature of about 60° C. to about 110° C. The reaction time is about 10 h to about 20 h.

The α-aryloxy ester is then contacted with an alkyl lithium compound to form the enolate. This reaction is is typically performed in an anhydrous, polar, aprotic solvent at a temperature of about −20° C. to about −110° C. After about 5 min to about 20 min. a 4-benzyloxybenzaldehyde represented by compound XXVII is added and the reaction is stirred for about 5 min. to about 30 min., then quenched with an aqueous solution of ammonium chloride or acetic acid in THF to form a 3-(4-benzyloxyphenyl)-3-hydroxy-2-substituted-2-aryloxy-propanoic ester represented by Structure XXVIII.

A solution of 3-(4-benzyloxyphenyl)-3-hydroxy-2-substituted-2-aryloxy-propanoic ester in an anhydrous aprotic solvent at a temperature of about −10° C. to about 10° C. was treated with an ether complex of boron trifluoride and triethylsilane. The reaction is gradually allowed to warm to room temperature then stirred for about 1 h to about 2.5 h. The mixture is quenched by adding an aqueous base to give 3-(4-benzyloxyphenyl)-2-substituted-2-aryloxy-propanoic ester represented by Structural Formula XXIX.

The 3-(4-benzyloxyphenyl)-2-substituted-2-aryloxy-propanoic ester is treated to remove the benzyl protecting group to yield a 3-phenyl-2-substituted-2-aryloxy-propanoic ester represented by Structural Formula XIX. Method for removing benzyl protecting groups from a phenol are known to those skilled in the art and can be found in Green, et al., *Protective Groups in Organic Synthesis*, 2$^{nd}$ Edition, John Wiley & Sons, Inc., p. 156–158.

Scheme IV:
Method of synthesizing compounds represented by Structural Formula XIX.

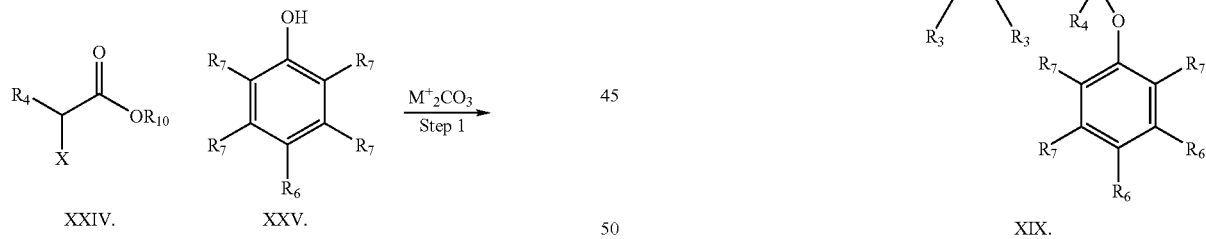

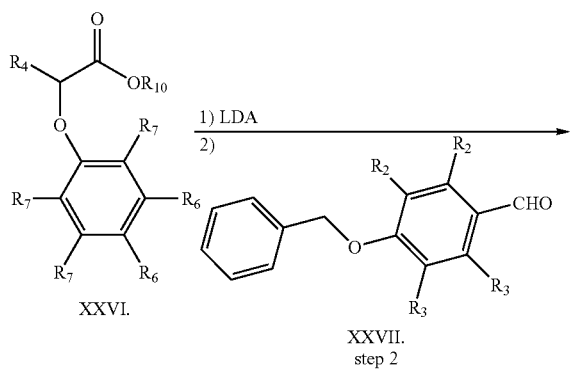

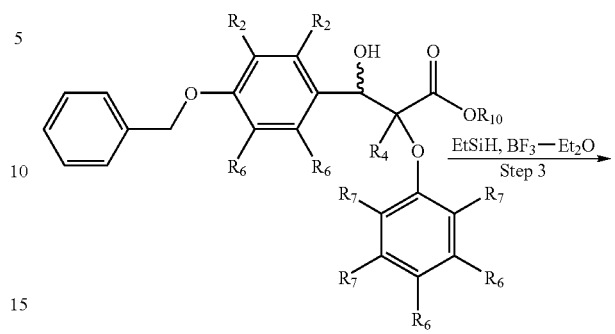

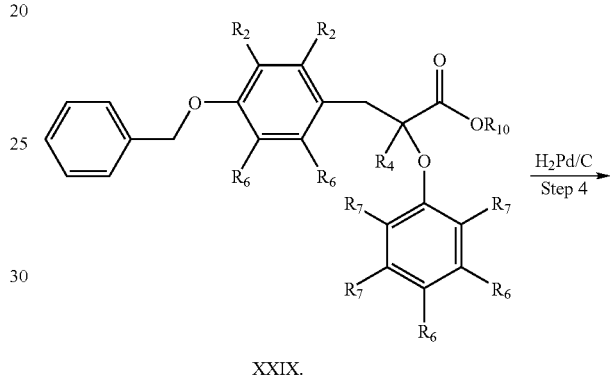

When aryloxy group contains electron donating group, such as alkyl, alkoxy groups, 3-(4-hydroxyphenoxy)-2-substituted-2-aryloxypropanoic ester can be prepared by following method.

A solution of 3-(4-benzyloxyphenyl)-3-hydroxy-2-substituted-2-aryloxy propanoic ester (XXVIII) in CH2Cl2 at 0° C. was added trifluoroacetic anhydride and pyridine. The mixture was allowed to warm up to r.t. for 2 h. The mixture was quenched by 1N HCl to give 3-(4-benzyloxyphenyl)-3-trifluoroacetate-2-substituted-2-aryloxy propanoic ester (?). It can then be converted to 3-(4-hydroxyophenyl)-2-substituted-2-aryloxypropanoic ester (XIX) by treatment with 10% Pd/C under 1 atm H2 in EtOAc for 48 h.

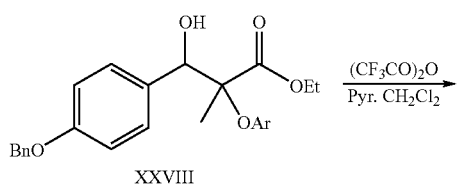

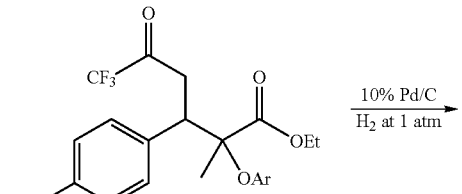

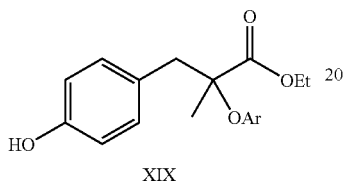

When aryloxy group contains basic functional groups, such as amine, aniline, 3-(4-hydroxyphenoxy)-2-substituted-2-aryloxypropanoic ester can be prepared by following method.

A solution of 3-(4-benzyloxyphenyl)-3-hydroxy-2-substituted-2-aryloxy propanoic ester (XXVIII) in dichloroethane was added trifluoroacetic acid and triethylsilane. The mixture was heated to reflux for 48 h. The reaction can be quenched with saturated aqueous NaHCO$_3$ to give 3-(4-benzyloxy-phenoxy)-2-substituted-2-aryloxypropanoic ester (XXIX). 3-(4-hydroxyphenyl)-2-substituted-2-aryloxypropanoic ester (XIX) can be obtained by removal of benzyl group using method described in previous context.

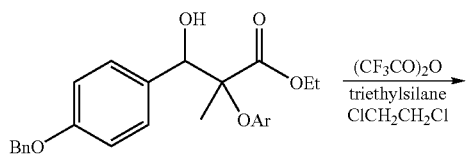

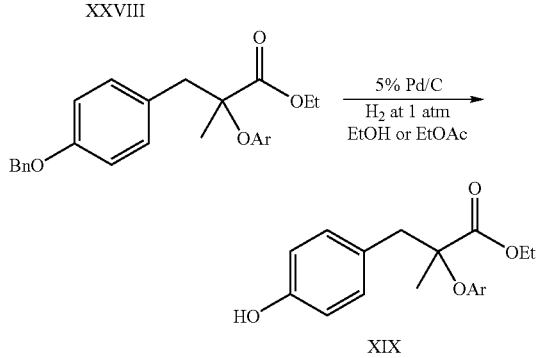

EXAMPLES

General: Infrared spectra were recorded on a Perkin Elmer 781 spectrometer. $^1$H NMR spectra were recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR were recorded on a Varian 400 MHz spectrometer at ambient temperature. Chemical shifts are reported in ppm on the δ scale, with the solvent resonance employed as the internal standard (CDCl$_3$ at 7.26 ppm and DMSO-d$_6$ at 2.52 ppm). Combustion analyses were performed by Eli Lilly & Company Microanalytical Laboratory. High resolution mass spectra were obtained on VG ZAB 3F or VG 70 SE spectrometers. Analytical thin layer chromatography was performed on EM Reagent 0.25 mm silica gel 60-F plates. Visualization was accomplished with UV light.

Example 1

3-{4-[2-(2-Biphenyl-4-yl-5-methyl-oxazol-4-yl)-ethoxy]-phenyl)-2-methyl-2-phenoxypropionic acid

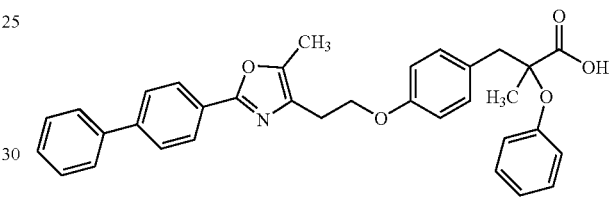

A. 2-Phenoxypropionic Acid Ethyl Ester

Phenol (28.5 g, 0.30 mol), Cs$_2$CO$_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over Na$_2$SO$_4$ and concentrated in vacuo to produce a golden oil (48.5 g, 83%) $^1$H NMR (250 MHz, CDCl$_3$): δ 7.31 (d, 2H, J=7.8), 7.02 (t, 1H, J=7.9), 6.93 (d, 2H, J=7.8), 4.79 (q, 1H, J=6.1), 4.26 (q, 2H, J=7.2), 1.66 (d, 3H, J=6.1), 1.24 (t, 3H, J=7.2). MS [EI+] 195 (M+H)$^+$ B. 2-Phenoxy-3-(4-Benzyloxyphenyl)-2-Methyl-propionic Acid Ethyl Ester A solution of LDA (16.5 mL, 24.7 mmol, 1.5M in cyclohexane) was cooled to −78 ° C. in a dry ice/acetone bath and then added to a solution of 3-(4-hydroxyphenyl)-2-methyl-2-phenoxypropionic acid ethyl ester (4.79 g, 24.7 mmol) in anhydrous THF (30 mL) also cooled to −78° C. under an atmosphere of nitrogen. After 5 min, 4-benzyloxy-benzaldehyde (4.76 g, 22.4 mmol) was added in one portion. After stirring for 10 min, the reaction mixture 20 was quenched with saturated solution of aqueous NH$_4$Cl (10 mL) and the mixture allowed to warm to ambient temperature. The biphasic mixture was diluted with ether (100 mL) and partitioned, and the organic layer was washed with brine, dried over MgSO$_4$ and concentrated in vacuo. The residue was purified by flash column chromatography (600 g silica, 25×200 mL fractions, gradient elution 0–20% ethyl acetate in hexanes) to provide a colorless oil (3.84 g, 42%) as a mixture of inseparable diastereomers of 3-(4-benzyloxy-phenyl)-2-phenoxy-3-hydroxy-2-methylpropionic acid ethyl ester which was used without further characterization or purification. $R_f$=0.32 in 4:1 hexanes:ethyl acetate.

3-(4-Benzyloxyphenyl)-3-hydroxy-2-phenoxy-2-methyl-propionic acid ethyl ester (3.84 g, 9.5 mmol) in anhydrous $CH_2Cl_2$ (30 mL) was cooled to 0° C. and treated with $BF_3$-$Et_2O$ (1.16 mL, 9.5 mmol) and triethylsilane (1.51 mL, 9.5 mmol). The mixture was stirred for 2 h and gradually warmed to ambient temperature. Saturated aqueous $Na_2CO_3$ (15 mL) was added and the mixture was stirred vigorously. The solution was partitioned and the organic layer was washed twice with water and brine, dried over $Na_2SO_4$, and concentrated in vacuo to produce 3-(4-benzyloxyphenyl)-2-phenoxy-2-methylpropionic acid ethyl ester as a colorless oil (1.34 g, 36%). $R_f$=0.90 (9:1 hexanes:ethyl acetate). $^1$H NMR (300 MHz, CDCl$_3$): δ 7.36–7.42 (m, 3H), 7.34 (t, 1H), 7.17–7.24 (m, 5H), 6.98 (t, 1H), 6.91 (d, 2H), 6.83 (d, 2H), 5.05 (s, 2H), 4.22 (q, 1H, J=7.1), 3.26 (d, 1H, J=13.7), 3.13 (d, 1H, J=13.7), 1.40 (s, 3H), 1.22 (t, 3H, J=7.1). MS [EI+] 408 (M+NH$_4$)$^+$ C. 3-(4-Hydroxyphenyl)-2-Methyl-2-Phenoxypropionic Acid Ethyl Ester 2-Phenoxy-3-(4-benzyloxyphenyl)-2-methyl-propionic acid ethyl ester (830 mg, 2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to a colorless oil (563 mg, 89%) $^1$H NMR (300 MHz, CDCl$_3$): δ 7.23 (t, 2H), 7.13 (d, 2H), 6.96 (t, 1H), 6.83 (d, 2H), 6.76 (d, 2H), 4.19 (q, 1H, J=7.1), 3.23 (d, 1H, J=12.4), 3.08 (d, 1H, J=12.4), 1.39 (s, 3H), 1.22 (t, J=7.1). MS [EI+] 318 (M+H)$^+$, [EI–] 359 (M+OAc$^-$).

3-(4-Hydroxyphenyl)-2-methyl-2-phenoxypropionic acid ethyl ester(approx 48 g) prepared in the same manner was purified by chiral chromatography to provided the individual enantiomers (Chiralcel OD, 8×27 cm, 7% IPA/heptane, 248 nm; (S)-isomer: 97.2% ee; (R)-isomer. >99% ee).

D. 4,5-Dimethyl-2-(4-bromophenyl)-oxazole oxide

A solution of 2,3-butanedione monooxime (50 g, 0.49 mol) and 4-bromo-benzaldehyde (101 g, 0.54 mol) in acetic acid (500 mL) was cooled to 0° C. and then gaseous HCl was bubbled through the solution for 35 min while the reaction was stirred in an ice bath. Diethyl ether (500 mL) was then added to the reaction to precipitate the product and the resultant slurry stirred 45 min at 0° C. before being filtered. The solids were rinsed with Et$_2$O (50 mL), taken up in water (1 L) and conc. NH$_4$OH (60 mL) added to the slurry. This mixture was extracted with CHCl$_3$, the organic layer was dried (MgSO$_4$), and the solvent removed in vacuo to give 97.4 g (74%) of 4,5-dimethyl-2-(4-bromophenyl)-oxazole oxide as a white solid. The compound should be used directly within 24–48 h: $^1$H NMR (500 MHz, CDCl$_3$) 8.34 (d, J=9.0 Hz, 2H), 7.61 (d, J=9.0 Hz, 2H), 2.35 (s, 3H), 2.20 (s, 3H); $^{13}$C (125 MHz, CDCl$_3$) 142.1, 131.9, 129.5, 126.3, 124.1, 122.2, 11.1, 6.2; IR (KBr) 1685, 1529, 1418, 1377, 1233, 1165 cm$^{-1}$; UV (EtOH)$_{max}$ 307 nm (24371); HRMS (TOF) m/z calculated for $C_{11}H_{11}^{79}BrNO_2$: 267.997, found 267.9951.

E. 2-(4-Bromophenyl-4-(chloromethyl)-5-methyloxazole

A solution of 4,5-dimethyl-2-(4-bromophenyl)-oxazole oxide (96.6 g, 0.36 mol) in CHCl$_3$ (0.90 L) was treated dropwise with phosphorous oxychloride (61.1 g, 0.40 mol) allowing the reaction to exotherm and then was stirred at reflux for 30 min. The reaction was then cooled to room temperature and washed with water (2×1 L). The combined aqueous washes were back extracted with CH$_2$Cl$_2$ (2×400 mL). The organic layers were dried (MgSO$_4$), and the solvent removed in vacuo to give crude product that was recrystallized from hot hexanes (300 mL), decanting the hot supernate away from a dark oily material. The remaining dark oil was agitated in additional hot hexanes (200 mL) and the combined supernates were cooled to 0° C. to crystallize the product which was isolated by filtration to give 74.2 g (72%) of 2-(4-bromophenyl-4-(chloromethyl)-5-methyloxazole as a lime-green powder: Rf=0.39 in 20% ethyl acetate/hexanes; $^1$H NMR (500 MHz, CDCl$_3$) 7.88–7.86 (m, 2H), 7.59–7.56 (m, 2H), 4.54 (s, 2H), 2.42 (s, 3H); $^{13}$C (125 MHz, CDCl$_3$) 159.2, 146.9, 133.2, 132.0, 127.6, 126.1, 124.7, 37.1, 11.5; IR (KBr) 2970, 1633, 1599, 1481, 1401, 1258, 1117, 1008 cm$^{-1}$; UV (EtOH)$_{max}$ 281 nm (21349); HRMS (FAB) m/z calculated for $C_{11}H_{10}^{79}BrClNO$: 285.9634, found 285.9641; Anal. Calculated for $C_{11}H_9ClBrNO$: C, 46.11; H, 3.17; N, 4.89; Cl, 12.37; Br, 27.88. Found C, 46.28; H 3.07; N, 4.81; Cl, 12.36; Br, 27.88.

F. 2-(4-Bromophenyl)-5-methyl-4-oxazoleacetic acid

To a solution of 2-(4-bromophenyl-4-(chloromethyl)-5-methyloxazole (64.8 g, 0.23 mol) in DMF (400 mL) was added powdered potassium cyanide (22.1 g, 0.34 mol) and potassium iodide (28.6 g, 0.17 mol) and the resultant mixture was heated to 85° C. for 3.5 h. The reaction mixture was then cooled to room temperature. Potassium carbonate (5 g) was dissolved in water (800 mL) and added dropwise to the reaction to precipitate 2-(4-bromophenyl)-4-(cyanomethyl)-5-methyloxazole (stir vigorously 15 min following addition) which was isolated by filtration and washed with water (2×400 mL). The crude 2-(4-bromophenyl)-4-(cyanomethyl)-5-methyloxazole was carried on as is in the next step without purification. $^1$H NMR (300 MHz, CDCl$_3$) 7.85 (m, 2H), 7.58 (m, 2H), 3.64 (s, 3H), 2.43 (s, 3H).

The crude 2-(4-bromophenyl)-4-(cyanomethyl)-5-methyloxazole (assume 0.22 mol) was combined with 2-methoxyethanol (630 mL) and 85% solid KOH (74.6 g, 1.33 mol) in water (360 mL) was added to the reaction. The mixture was heated to reflux for 3 h, cooled, quenched with 2 M HCl (500 mL), and extracted with CH$_2$Cl$_2$. The organic layer was dried (MgSO$_4$), and the solvent removed in vacuo, using toluene to azeotropically remove residual 2-methoxyethanol. The crude product (57.3 g) was recrystallized from toluene (450 mL) to give 39.8 g (60%) of 2-(4-bromophenyl)-5-methyl-4-oxazoleacetic acid as an off-white powder: Rf=0.23 in 10% MeOH/CH$_2$Cl$_2$; $^1$H NMR (500 MH, CDCl$_3$) 9.00 (br s, 1H), 7.85–7.83 (m, 2H), 7.58–7.56 (m, 2H), 3.62 (s, 3H), 2.36 (s, 3H); $^{13}$C (125 MHz, CDCl$_3$) 173.8, 159.0, 146.2, 132.0, 129.1, 127.6, 125.9, 124.7, 31.5, 10.2; IR (CHCl$_3$) 2923, 1699, 1641, 1481, 1428, 1306, 1234, 1010, 829, 727 cm$^{-1}$; UV (EtOH)$_{max}$ 288 nm (19626).

G. 2-(4-Bromophenyl)-5-methyl-4-oxazoleethanol

A solution of 2-(4-bromophenyl)-5-methyl-4-oxazoleacetic acid (39.1 g, 0.13 mol) in dry THF (175 mL) was treated dropwise with borane-THF complex (227 mL of a 1.0 M solution in THF, 1.3 mol) over 2 h (reaction temperature to 35° C.). After stirring 2 h at room temperature under N$_2$, the reaction was quenched with slow addition of methanol (60 mL) and stirred overnight at room temperature. The reaction was diluted with 1 N NaOH (50 mL) and extracted with CH$_2$Cl$_2$ (2×200 mL). The organic layer was washed with H$_2$O (3×100 mL), dried (MgSO$_4$), and the solvent removed in vacuo to give 38.7 g of crude product that was recrystallized from toluene (200 mL, wash solid with cold hexanes) to give 26.9 g (72%) of 2-(4-bromophenyl)-5-methyl-4-oxazoleethanolas a white powder: Rf=0.37 in 10% MeOH/CH$_2$Cl$_2$; $^1$H NMR (500 MHz, CDCl$_3$) 7.84–7.82 (m, 2H), 7.57–7.55 (m, 2H), 3.91 (q, J=5.5 Hz, 2H), 3.14 (t, J=6 Hz, OH), 2.72 (t, J=5.5 Hz, 2H), 2.33 (s, 3H); $^{13}$C (125 MHz, CDCl$_3$) 158.7, 144.5, 134.2, 131.9, 127.4, 126.4, 124.3, 61.8, 28.1, 10.1; IR (KBr) 3293, 2948, 1642, 15985, 1480, 1472, 1401, 1053, 1003, 836, 734 cm$^{-1}$; UV (EtOH)$_{max}$ 290 nm (20860); Anal. Calculated for C$_{12}$H$_{12}$BrNO$_2$: C, 51.09; H, 4.29; N, 4.96; Br, 28.32. Found C, 51.31; H 4.06; N, 4.90; Br, 28.19.

H. 2-(4-Biphenyl)-5-methyloxazoleethanol 2-(4-Bromophenyl)-5-methyl-4-oxazoleethanol (10.0 g, 35.0 mmol) and phenylboronic acid (4.5 g, 38.0 mmol) were dissolved in n-propanol (120 mL) before adding triphenylphosphine (165.2 mg, 0.63 mmol), palladium acetate (46 mg, 2.1 mmol), and Na$_2$CO$_3$ (4.5 g, 42 mmol dissolved in 30 mL distilled H$_2$O). The solution was heated to reflux and stirred for 1.5 h. After cooling to ambient temperature, the mixture was concentrated under reduced pressure and then partitioned between CH$_2$Cl$_2$ (100 mL) and 1N NaOH (100 mL). The aqueous phase was extracted with CH$_2$Cl$_2$ (2×50 mL) and the combined organic phases were dried (MgSO$_4$) and concentrated under reduced pressure to provide 2-(4-biphenyl)-5-methyl-4-oxazoleethanol (9.5 g, 97% yield) as a white solid which was used directly without further purification. $^1$H NMR (500 MHz, CDCl$_3$) 8.01 (d, 2H), 7.77–7.50 (m, 4H), 7.46 (m, 2H), 7.38 (m, 1H), 3.91 (q, J=5.5 Hz, 2H), 3.18 (t, J=6 Hz, OH), 2.72 (t, J=5.5 Hz, 2H), 2.33 (s, 3H).

I. Toluene-4-sulfonic acid 2-(5-methyl-2-biphenyl-4-yl-oxazol-4-yl)ethyl ester

To a solution of 2-(4-biphenyl)-5-methyl-4-oxazoleethanol (15.8 g, 56.6 mmol) in CH$_2$Cl$_2$ (250 mL) at room temperate under N$_2$ was added pyridine (14.7 g, 185 mmol, 15.0 mL) and DMAP (2.03 g, 16.6 mmol) followed by portionwise addition of tosyl anhydride (24.57 g, 75.2 mmol). The reaction exothermed to 32° C. and was stirred 30 min before additional 2.3 of tosyl anhydride was added. The mixture was diluted with 100 mL of CH$_2$Cl$_2$ and stirred vigorously with 1N HCl (150 mL) for 15 min, and then the organic phase was dried (MgSO$_4$) and filtered through a pad of silica gel (100 mL, packed with CH$_2$Cl$_2$). After rinsing the silica gel with ethyl acetate (100 mL) the solution was concentrated to give toluene-4-sulfonic acid 2-methyl 2-(5-methyl-2-biphenyl-4-yl-oxazol-4-yl)ethyl ester as a white solid (23.3 g, 95%) which was used without further purification: Rf=0.51 in 60% ethyl acetate/hexanes; $^1$H NMR (400 MHz, CDCl$_3$) 7.97 (d, 2H), 7.70 (d, 2H), 7.66 (t, 2H), 7.65 (d, 2H), 7.51 (t, 1H), 7.42 (d, 2H), 7.24 (d, 2H), 4.37 (t, 2H), 2.88 (t, 2H), 2.37 (s, 3H), 2.26 (s, 3H).

J. 3-{4-[2-(2-Biphenyl-4-yl-5-methyl-oxazol-4-yl)-ethoxy]-phenyl}-2-methyl-2-phenoxypropionic acid ethyl ester 3-(4-Hydroxyphenyl)-2-methyl-2-phenoxypropionic acid ethyl ester (495 mg, 1.7 mmol), and toluene-4-sulfonic acid 2-(2-biphenyl-4-yl-5-methyl-oxazol-4-yl)-ethyl ester (2.2 mmol) and Cs$_2$CO$_3$ (700 mg, 2.2 mmol) are combined in anhydrous DMF (25 mL) and stirred for 16 h at 55° C. under an atmosphere of nitrogen. The mixture was then cooled and diluted with ethyl acetate (100 mL), and washed with water then brine. The organic layer was dried with Na$_2$SO$_4$ and concentrated in vacuo to a viscous yellow oil. The residue was purified by flash column chromatography (100 g silica, 60×15 mL fractions, gradient elution 0–20% ethyl acetate in hexanes) to provide the title compound as a colorless oil.

K. 3-{4-[2-(2-Biphenyl-4-yl-5-methyl-oxazol-4-yl)ethoxy]-phenyl}-2-methyl-2-phenoxypropionic acid:

3-{4-[2-(2-Biphenyl-4-yl-5-methyl-oxazol-4-yl)-ethoxy]-phenyl}-2-methyl-2-phenoxypropionic acid ethyl ester (3.6 mmol) in MeOH (7 mL) was treated with 2N NaOH (7 mL) and warmed to 55° C. After 18 h, the mixture was concentrated under reduced pressure and then acidified with 5N HCl to pH=1. The solution was extracted with EtOAc and then the organic phases dried (Na$_2$SO$_4$), filtered and concentrated to a white solid (7%). MS [EI+] 534 (M+H)$^+$, 566 (M+Na)$^+$, [EI–] 532 (M–H)$^+$; HPLC: T=3.29 min, purity 99%.

Example 2

3-{4-[2-(2-Biphenyl-3-yl-5-methyl-oxazol-4-yl)-ethoxy]-phenyl}-2-methyl-2-phenoxypropionic acid

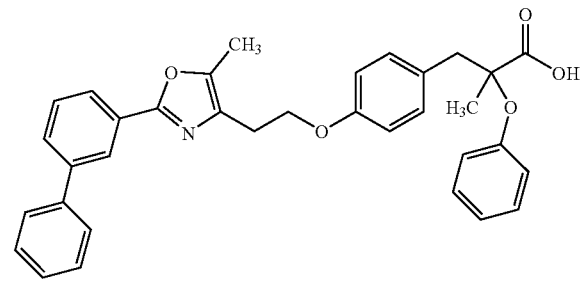

A. 2-(3-Bromophenyl)-4,5-dimethyloxazole-3-oxide

A solution of 2,3-butanedione monooxime (50 g, 0.49 mol) and 3-bromobenzaldehyde (101 g, 0.54 mol) in acetic acid (500 mL) was cooled to 0° C. and then gaseous HCl was bubbled through the solution for 35 min while the reaction was stirred in an ice bath. Diethyl ether (500 mL) was then added to the reaction to precipitate the product and the resultant slurry stirred 45 min at 0° C. before being filtered. The solids were rinsed with Et$_2$O (50 mL), taken up in water (1 L) and concentrated NH$_4$OH (60 mL) added to the slurry. This mixture was extracted with CHCl$_3$, the organic layer was dried (MgSO$_4$), and the solvent removed in vacuo to give 97.4 g (74%) of 2-(3-bromophenyl)-4,5-dimethyloxazole-3-oxide as a white solid. The compound should be used directly with 24–48 h.

B. 2-(3-Bromophenyl)-4-(chloromethyl)-5-methyloxazole

A solution of 2-(3-bromophenyl)-4,5-dimethyloxazole-3-oxide (96.6 g, 0.36 mol) in CHCl$_3$ (0.90 L) was treated dropwise with phosphorous oxychloride (61.1 g, 0.40 mol) allowing the reaction to exotherm and then stirred at reflux for 30 min. The reaction was then cooled to room temperature and washed with water (2×1 L). The combined aqueous washes were back extracted with CH$_2$Cl$_2$ (2×400 mL). The organic layers were dried (MgSO$_4$), and the solvent removed in vacuo to give crude product that was recrystallized from hot hexanes (300 mL), decanting the hot supernate away from a dark oily material. The remaining dark oil was agitated in additional hot hexanes (200 mL) and the combined supernates were cooled to 0° C. to crystallize the product which was isolated by filtration to give 74.2 g (72%) of 2-(3-bromophenyl)-4-(chloromethyl)-5-methyloxazole as a lime-green powder.

C. 2-(3-Bromophenyl)-5-methyl-4-oxazoleacetic acid

To a solution of 2-(3-bromophenyl)-4-(chloromethyl)-5-methyloxazole (64.8 g, 0.23 mol) in DMF (400 mL) was added powdered potassium cyanide (22.1 g, 0.34 mol) and potassium iodide (28.6 g, 0.17 mol) and the resultant mixture heated to 85° C. for 3.5 h. The reaction mixture was then cooled to room temperature. Potassium carbonate (5 g) was dissolved in water (800 mL) and added dropwise to the reaction to precipitate the product (stir vigorously 15 min following addition) which was isolated by filtration and washed with water (2×400 mL). The crude [2-(3-bromophenyl)-5-methyloxazole-4-yl]-acetonitrile was carried on as is in the next step without purification The crude [2-(3-bromophenyl)-5-methyloxazole-4-yl]-acetonitrile (assume 0.22 mol) was combined with 2-methoxyethanol (630 mL) and 85% solid KOH (74.6 g, 1.33 mol) in water (360 mL) was added to the reaction. The mixture was heated to reflux for 3 h, cooled, quenched with 2 M HCl (500 mL), and extracted with $CH_2Cl_2$. The organic layer was dried ($MgSO_4$), and the solvent removed in vacuo, using toluene to azeotropically remove residual 2-methoxyethanol. The crude product (57.3 g) was recrystallized from toluene (450 mL) to give 39.8 g (60%) of 2-(3-bromophenyl)-5-methyl-4-oxazoleacetic acid as an off-white powder.

D. 2-[2-(3-Bromo-phenyl)-5-methyloxazol-4-yl]ethanol

A solution of 2-(3-bromophenyl)-5-methyl-4-oxazoleacetic acid (39.1 g, 0.13 mol) in dry THF (175 mL) was treated dropwise with borane-THF complex (227 mL of a 1.0 M solution in THF, 1.3 mol) over 2 h (reaction temperature to 35° C.). After stirring 2 h at room temperature under $N_2$, the reaction was quenched with slow addition of methanol (60 mL) and stirred overnight at room temperature. The reaction was diluted with 1 N NaOH (50 mL) and extracted with $CH_2Cl_2$ (2×200 mL). The organic layer was washed with $H_2O$ (3×100 mL), dried ($MgSO_4$), and the solvent removed in vacuo to give 38.7 g of crude product that was recrystallized from toluene (200 mL, wash solid with cold hexanes) to give 26.9 g (72%) of 2-(3-bromophenyl)-5-methyl-4-oxazoleethanol as a white powder.

E. 2-(3-Biphenyl)-5-methyl-4-oxazoleethanol 2-(3-Bromophenyl)-5-methyl-4-oxazoleethanol (35.0 mmol) and phenylboronic acid (4.5 g, 38.0 mmol) were dissolved in n-propanol (120 mL) before adding triphenylphosphine (165.2 mg, 0.63 mmol), palladium acetate (46 mg, 2.1 mmol), and $Na_2CO_3$ (4.5 g, 42 mmol dissolved in 30 mL distilled $H_2O$). The solution was heated to reflux and stirred for 1.5 h. After cooling to ambient temperature, the mixture was concentrated under reduced pressure and then partitioned between $CH_2Cl_2$ (100 mL) and 1N NaOH (100 mL). The aqueous phase was extracted with $CH_2Cl_2$ (2×50 mL) and the combined organic phases were dried ($MgSO_4$) and concentrated under reduced pressure to provide the desired product which was used directly without further purification. $^1$H NMR (CDCl$_3$) δ 6.42 (d, J=8.6 Hz, 2H), 6.38 (d, J=8.6 Hz, 2H), 4.20 (q, J=7.2 Hz, 2H), 2.61 (t, J=6.0 Hz, 2H), 2.55 (t, J=6.0 Hz, 2H), 1.6 (m, 4H), 1.49 (s, 6H), 1.23 (t, J=7.2 Hz, 3H); MS (ES+) m/e (% relative intensity) 301.1 (28), 279.2 (M$^+$+1, 49), 233.1 (100), 205.1 (470), 165.1 (88).

F. Toluene-4-sulfonic acid 2-(2-biphenyl-3-yl-5-methyloxazol-4-yl)ethyl ester

To a solution of 2-(3-biphenyl)-5-methyl-4-oxazoleethanol (31.5 mmol) in $CH_2Cl_2$ (150 mL) at room temperature under $N_2$ was added pyridine (8.74 g, 110 mmol, 8.9 mL) and DMAP (0.97 g, 7.88 mmol) followed by portionwise addition of tosyl anhydride (12.7 g, 37.8 mmol). The reaction exothermed to 32° C. and was stirred 1 h before 1N HCl (200 mL) was added. The mixture was stirred vigorously 15 min, and then the organic phase was dried ($MgSO_4$) and filtered through a pad of silica gel (200 mL, packed with $CH_2Cl_2$). After rinsing the silica gel with ethyl acetate (100 mL) the solution was concentrated to toluene-4-sulfonic acid 2-(2-biphenyl-3-yl-5-methyloxazol-4-yl)ethyl ester which was used without further purification. $^1$H NMR (400 MHz, CDCl$_3$) δ 8.06 (s, 1H), 7.80 (d, J=8.0 Hz, 1H), 7.6 (m, 5H), 7.4 (m, 4H), 7.12 (d, J=8.4 Hz, 2H), 4.28 (t, J=6.0 Hz, 2H), 2.79 (t, J=6.0 Hz, 2H), 2.28 (s, 3H), 2.12 (s, 3H); MS (ES+) m/e (% relative intensity) 436.1 (44), 435.1 (70), 434.1 (M$^+$+1, 100).

G. 3-{4-[2-(2-Biphenyl-3-yl-5-methyl-oxazol-4-yl)ethoxy]-phenyl}-2-methyl-2-phenoxypropionic acid Toluene-4-sulfonic acid 2-(2-biphenyl-3-yl-5-methyl-oxazol-4-yl)-ethyl ester (0.132 mmol) was added to a one dram, screw-cap vial and diluted with ethanol (0.5 mL). To this solution are added 3-(4-hydroxyphenyl)-2-methyl-2-phenoxypropionic acid ethyl ester (see Ex. 1, Part C) (0.5 mL of a 0.264 M solution in ethanol, 0.132 mmol) and polystyrene bound 1,5,7-triazabicyclo[4.4.0]dec-5-ene (100–125 mg, 2.6 mmol/g) and the vial was tightly closed The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100 μl) and the vial resealed tightly. The solution was heated in a block heater at 55° C. for 3–16 h, or until MS analysis indicates the completion of the hydrolysis. The solvents are removed with a stream of nitrogen or under reduced pressure and the residue redissolved in 1 mL water. The solution was acidified with aqueous HCl (5N solution, 150 μl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by massirected HPLC to produce the product as a white solid (25%). MS [EI+] 534 (M+H)$^+$, 566 (M+Na)$^+$, [EI−] 532 (M−H)$^+$; HPLC: T=3.26 min, purity 97%.

Example 3

2-Methyl-3-(4-{2-[5-methyl-2-(4-thiophen-2-yl-phenyl)-oxazol-4-yl]-ethoxy}-phenyl)-2-phenoxypropionic acid

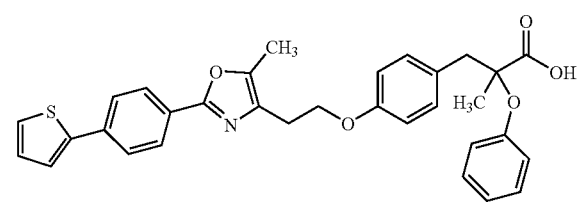

A. 2-(4-Thiophen-2-yl-phenyl)-5-methyl-4-oxazoleethanol 2-(4-Bromophenyl)-5-methyl-4-oxazoleethanol (10.0 g, 35.0 mmol) (see Ex. 1, Part G) and 2-thiophenyl boronic acid (38.0 mmol) were dissolved in n-propanol (120 ml) before adding triphenylphosphine (165.2 mg, 0.63 mmol), palladium acetate (46 mg, 2.1 mmol), and $Na_2CO_3$ (4.5 g, 42 mmol dissolved in 30 mL distilled $H_2O$). The solution was heated to reflux and stirred for 1.5 h. After cooling to ambient temperature, the mixture was concentrated under reduced pressure and then partitioned between $CH_2Cl_2$ (100 mL) and 1N NaOH (100 mL). The aqueous phase was extracted with $CH_2Cl_2$ (2×50 mL) and the combined organic phases were dried ($MgSO_4$) and concentrated under reduced pressure to provide 2-(4-thiophen-2-yl-phenyl)-5-methyl-4-oxazoleethanol.

B. Toluene-4-sulfonic acid 2-(5-methyl-2-(4-thiophen-2-yl-phenyl)-oxazol-4-yl)ethyl ester To a solution of 2-(4-thiophen-2-yl-phenyl)-5-methyl-4-oxazoleethanol (56.6 mmol) in $CH_2Cl_2$ (250 mL) at room temperature under $N_2$ was added pyridine (14.7 g, 185 mmol, 15.0 mL) and DMAP (2.03 g, 16.6 mmol) followed by portionwise addition of tosyl anhydride (24.57 g, 75.2 mmol). The reaction exothermed to 32° C. and was stirred 30 min before additional 2.3 of tosyl anhydride was added. The mixture was diluted with 100 mL of $CH_2Cl_2$ and stirred vigorously with 1N HCl (150 mL) for 15 min, and then the organic phase was dried ($MgSO_4$) and filtered through a pad of silica gel (100 mL, packed with $CH_2Cl_2$). After rinsing the silica gel with ethyl acetate (100 mL) the solution was concentrated to give toluene-4-sulfonic acid 2-(5-methyl-2-(4-thiophen-2-yl-phenyl)-oxazol-4-yl)ethyl ester.

C. 2-Methyl-3-(4-{2-[5-methyl-2-(4-thiophen-2-yl-phenyl)-oxazol-4-yl]-ethoxy}-phenyl)-2-phenoxypropionic acid Toluene-4-sulfonic acid 2-(5-methyl-2-(4-thiophen-2-yl-phenyl)-oxazol-4-yl)ethyl ester (0.132 mmol) was added to a one dram, screw-cap vial and diluted with ethanol (0.5 mL). To this solution are added 3-(4-hydroxyphenyl)-2-methyl-2-phenoxypropionic acid ethyl ester (see Ex. 1, Part C) (0.5 mL of a 0.264 M solution in ethanol, 0.132 mmol) and polystyrene bound 1,5,7-triazabicyclo[4.4.0]dec-5-ene (100–125 mg, 2.6 mmol/g) and the vial was tightly closed. The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100 μl) and the vial resealed tightly. The solution was heated in a block heater at 55° C. for 3–16 h, or until MS analysis indicates the completion of the hydrolysis. The solvents are removed with a stream of nitrogen or under reduced pressure and the residue redissolved in 1 mL water. The solution was acidified with aqueous HCl (5N solution, 150 μl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by mass-directed HPLC to produce the product as a white solid (24%). MS [EI+] 540 (M+H)+, 562 (M+Na)+, [EI−] 538 (M−H)+; HPLC: T=3.24 min, purity 100%.

Example 4

3-(4-{2-[2-(4'-Fluorobiphenyl-3-yl)-5-methyloxazol-4-yl]ethoxy}phenyl)-2-methyl-2-phenoxypropionic acid

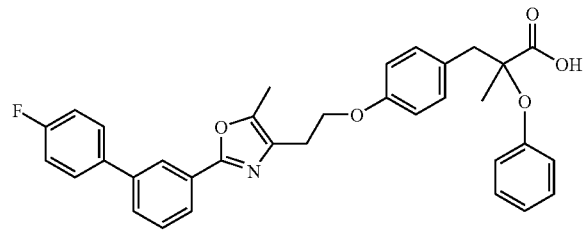

A. 2-[2-(4'-Fluorobiphenyl-3-yl)-5-methyloxazol-4-yl]ethanol

2-[2-(3-Bromo-phenyl)-5-methyloxazol-4-yl]ethanol (1.0 g, 3.54 mmol) (see Ex. 2, Part D) and para-fluorophenyl boronic acid (744 mg, 5.32 mmol) were stirred in n-PrOH (10 mL) under nitrogen, to which 2M $Na_2CO_3$ (3.54 mL) was added. The mixture was heated at 85° C., and after $Pd(PPh_3)_4$ (41 mg, 0.0354 mmol) was added, the reaction proceeded for 0.5 h. Once the reaction mixture had cooled to room temperature, it was concentrated and taken up in $CH_2Cl_2$ (20 mL), then washed with 0.5M NaOH (20 mL). The aqueous layer was back-extracted with $CH_2Cl_2$ (10 mL), combined organics were washed with 1M NaOH (10 mL), followed by $H_2O$ (10 mL), then dried over $Na_2SO_4$, and concentrated to a crude solid. Recrystallized from ethyl acetate:hexanes (1:1) and vacuum oven-dried at 50° C. to yield a tan solid (375 mg, 36%). $^1$H NMR (400 MHz, $CDCl_3$) δ 8.17 (s, 1H), 7.96 (d, J=7.6 Hz, 1H) 7.63–7.59 (m, 3H), 7.50 (t, J=7.6 Hz, 1H), 7.18–7.13 (m, 2H) 3.95 (t, J=5.6 Hz, 2H), 2.76 (t, J=5.6 Hz, 2H), 2.37 (s, 3H); MS (EI) 298.1 (M+H)+.

B. Toluene-4-sulfonic acid 2-[2-(4'-fluorobiphenyl-3-yl)-5-methyloxazol-4-yl]ethyl ester To a solution of 2-[2-(4'-fluorobiphenyl-3-yl)-5-methyloxazol-4-yl]ethanol (11.6 mmol) in $CH_2Cl_2$ (46 mL) at room temperature under $N_2$ was added pyridine (3.28 mL) and DMAP (0.43 g, 3.48 mmol) followed by portionwise addition of tosyl anhydride (4.54 g, 13.9 mmol). The reaction exothermed to 32° C. and was stirred 2 h before 1N HCl (50 mL) was added. The mixture was stirred vigorously 15 min, and then the organic phase was dried ($MgSO_4$) and then concentrated under reduced pressure. The residue was purified by column chromatography (40 mL $SiO_2$, 50% EtOAc/hexanes) to provide toluene-4-sulfonic acid 2-[2-(4'-fluorobiphenyl-3-yl)-5-methyloxazol-4-yl]ethyl ester: $^1$H NMR (400 MHz, $CDCl_3$) δ 8.08 (s, 1H), 7.86 (d, J=7.6 Hz, 1H), 7.67 (d, J=8.4 Hz, 2H), 7.63–7.59 (m, 3H), 7.50 (t, J=7.6 Hz, 1H), 7.19–7.14 (m, 4H), 4.33 (t, J=6.4 Hz, 2H), 2.86 (t, J=6.4 Hz, 2H), 2.33 (s, 3H), 2.19 (s, 3H); MS (EI) 452.1 (M+H)+.

C. 3-(4-{2-[2-(4'-Fluorobiphenyl-3-yl)-5-methyloxazol-4-yl]ethoxy}phenyl)-2-methyl-2-phenoxypropionic acid ethyl ester 3-(4-Hydroxyphenyl)-2-methyl-2-phenoxypropionic acid ethyl ester (495 mg, 1.7 mmol) (see Ex. 1, Part C), toluene-4-sulfonic acid 2-[2-(4'-fluorobiphenyl-3-yl)-5-methyloxazol-4-yl]ethyl ester (2.2 mmol) and $Cs_2CO_3$ (700 mg, 2.2 mmol) are combined in anhydrous DMF (25 mL) and stirred for 16 h at 55° C. under an atmosphere of nitrogen. The mixture was then cooled and diluted with ethyl acetate (100 mL), and washed with water then brine. The organic layer was dried with Na$_2$SO$_4$ and concentrated in vacuo to a viscous yellow oil. The residue was purified by flash column chromatography (100 g silica, 60×15 mL fractions, gradient elution 0–20% ethyl acetate in hexanes) to provide the title compound as a colorless oil. $^1$H NMR (400 MHz, CDCl$_3$) δ 8.18–8.17 (m, 1H), 7.96–7.94 (m, 1H), 7.62–7.57 (m, 3H), 7.51–7.47 (m, 1H), 7.23–7.11 (m, 2H), 7.16–7.11 (m, 3H), 6.98–6.94 (m, 1H), 6.84–6.81 (m, 4H), 6.78–6.75 (m, 1H), 4.24 (t, J=6.4 Hz, 2H), 4.20 (q, J=7.2 Hz, 2H), 3.26 (d, J=14.0 Hz, 1H), 3.10 (d, J=14.0 Hz, 1H), 2.99 (t, J=6.4 Hz, 2H), 2.40 (s, 3H), 1.38 (s, 3H), 1.21 (t, J=7.2 Hz, 3H); MS (EI) 580.2 (M+)$^+$.

D. 3-(4-{2-[2-(4'-Fluorobiphenyl-3-yl)-5-methyloxazol-4-yl]ethoxy)phenyl)-2-methyl-2-phenoxypropionic acid 3-(4-{2-[2-(4'-Fluorobiphenyl-3-yl)-5-methyloxazol-4-yl]phenyl)-2-methyl-2-phenoxypropionic acid ethyl ester (3.6 mmol) in MeOH (7 mL) was treated with 2N NaOH (7 mL) and warmed to 55° C. After 18 h, the mixture was concentrated under reduced pressure and then acidified with 5N HCl to pH=1. The solution was extracted with EtOAc and then the organic phases dried (Na$_2$SO$_4$), filtered and concentrated to a white solid. $^1$H NMR (400 MHz, CDCl$_3$) δ 8.18, (s, 1H), (d, J=7.6 Hz, 1H), 7.62–7.58 (m, 3H),7.48 (t, J=7.6 Hz, 1H), 7.24–7.03 (m, 7H), 6.90 (t, J=8.4 Hz, 2H), 6.83 (t, J=8.4 Hz, 2H), 4.22 (t, J=6.8 Hz, 2H), 3.25 (d, J=14.0 Hz, 1H), 3.15 (d, J=14.0 Hz, 1H), 3.01 (t, J=6.8 Hz, 2H), 2.40 (s, 3H), 1.42 (s, 3H); MS (EI) 552.3 (M+H)$^+$, 550.3 (M−H)$^-$.

Example 5

2-Methyl-3-(4-{2-[5-methyl-2-(3-thiophen-2-ylphenyl)oxazol-4-yl]ethoxy}phenyl)-2-phenoxypropionic acid

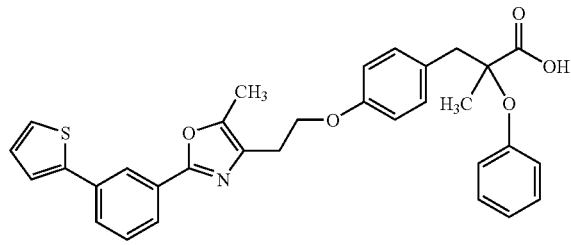

A. 2-[5-Methyl-2-(3-thiophen-2-ylphenyl)oxazol-4-ylethanol:

2-[2-(3-Bromo-phenyl)-5-methyloxazol-4-yl]ethanol (1.0 g, 3.54 mmol) (see Ex. 2, Part D) and 2-thiophene boronic acid (5.32 mmol) were stirred in n-PrOH (10 mL) under nitrogen, to which 2M Na$_2$CO$_3$ (3.54 mL) was added. The mixture was heated at 85° C., and after Pd(PPh$_3$)$_4$ (41 mg, 0.0354 mmol) was added, the reaction proceeded for 0.5 h. Once the reaction mixture had cooled to room temperature, it was concentrated and taken up in CH$_2$Cl$_2$ (20 mL), then washed with 0.5M NaOH (20 mL). The aqueous layer was back-extracted with CH$_2$Cl$_2$ (10 mL), combined organics were washed with 1M NaOH (10 mL), followed by H$_2$O (10 mL), then dried over Na$_2$SO$_4$, and concentrated to a crude solid. Recrystallized from ethyl acetate:hexanes (1:1) and vacuum oven-dried at 50° C. to yield a tan solid. $^1$H NMR (400 MHz, CDCl$_3$) δ 8.24 (s, 1H), 7.91 (d, J=8.0 Hz, 1H), 7.66 (d, J=8.0 Hz, 1H), 7.45 (t, J=8.0 Hz, 1H),7.42 (dd, J=3.6 Hz, J=0.8 Hz, 1H), 7.32 (dd, J=5.2 Hz, J=0.8 Hz, 1H), 7.12 (dd, J=5.2 Hz, J=3.6 Hz 1H), 3.95 (t, J=5.6 Hz, 2H), 2.76 (t, J=5.6 Hz, 2H), 2.37 (s, 3H); MS (EI) 286.1 (M+H)$^+$.

B. Toluene-4-sulfonic acid 2-[5-methyl-2-(3-thiophen-2-ylphenyl)oxazol-4-yl]ethyl ester To a solution of 2-[5-methyl-2-(3-thiophen-2-ylphenyl) oxazol-4-ylethanol (11.6 mmol) in CH$_2$Cl$_2$ (46 mL) at room temperature under N$_2$ was added pyridine (3.28 mL) and DMAP (0.43 g, 3.48 mmol) followed by portionwise addition of tosyl anhydride (4.54 g, 13.9 mmol). The reaction exothermed to 32° C. and was stirred 2 h before 1N HCl (50 mL) was added. The mixture was stirred vigorously 15 min, and then the organic phase was dried (MgSO$_4$) and then concentrated under reduced pressure. The residue was purified by column chromatography (40 mL SiO$_2$, 50% EtOAc/hexanes) to provide toluene-4-sulfonic acid 2-[5-methyl-2-(3-thiophen-2-ylphenyl)oxazol-4-yl]ethyl ester: $^1$H NMR (400 MHz, CDCl$_3$) δ 8.10 (s, 1H), 7.78 (d, J=7.6 Hz, 1H), 7.66 (d, J=8.4 Hz, 2H), 7.65 (d, J=7.6 Hz, 1H), 7.44 (t, J=7.6 Hz, 1H), 7.41 (dd, J=4.0 Hz, J=1.2 Hz, 1H), 7.33 (dd, J=5.2 Hz, J=1.2 Hz, 1H), 7.17 (d, J=8.4 Hz, 2H), 7.12 (dd, J=4.0 Hz, J=5.2 Hz, 1H), 4.33 (t, J=6.2 Hz, 2H), 2.84 (t, J=6.2 Hz, 2H), 2.33 (s, 3H), 2.17 (s, 3H); MS (EI) 440.1 (M+H)$^+$.

C. 2-Methyl-3-(4-{2-[5-methyl-2-(3-thiophen-2-ylphenyl) oxazol-4-yl]ethoxy}phenyl)-2-phenoxypropionic acid ethyl ester 3-(4-Hydroxyphenyl)-2-methyl-2-phenoxypropionic acid ethyl ester (495 mg, 1.7 mmol) (see Ex. 1, Part C), toluene-4-sulfonic acid 2-[5-methyl-2-(3-thiophen-2-ylphenyl)oxazol-4-yl]ethyl ester (2.2 mmol) and Cs$_2$CO$_3$ (700 mg, 2.2 mmol) are combined in anhydrous DMF (25 mL) and stirred for 16 h at 55° C. under an atmosphere of nitrogen. The mixture was then cooled and diluted with ethyl acetate (100 mL), and washed with water then brine. The organic layer was dried with Na$_2$SO$_4$ and concentrated in vacuo to a viscous yellow oil. The residue was purified by flash column chromatography (100 g silica, 60×15 mL fractions, gradient elution 0–20% ethyl acetate in hexanes) to provide the title compound as a colorless oil. $^1$H NMR (400 MHz, CDCl$_3$) δ 8.23 (s, 1H), 7.90 (d, J=7.6 Hz, 1H), 7.65 (d, J=7.6 Hz, 1H), 7.44 (t, J=8.0 Hz, 1H), 7.42–7.41 (m, 1H), 7.31 (d, J=5.2 Hz, 1H), 7.23–7.09 (m, 5H), 6.96 (t, J=7.2 Hz, 1H), 6.85–6.81 (m, 4H), 4.25 (t, J=6.8 Hz, 2H), 7.20 (q, J=7.2 Hz, 2H), 3.26 (d, J=14.0 Hz, 1H), 3.10 (d, J=14.0 Hz, 1H), 3.00 (t, J=6.8 Hz, 2H), 2.40 (s, 3H), 1.38 (s, 3H), 1.21 (t, J=7.2 Hz, 3H); MS (EI) 568.2 (M+H)$^+$.

D. 2-Methyl-3-(4-{2-[5-methyl-2-(3-thiophen-2-ylphenyl) oxazol-4-yl]ethoxy}phenyl)-2-phenoxypropionic acid 2-Methyl-3-(4-{2-[5-methyl-2-(3-thiophon-2-ylphenyl) oxazol-4-yl]ethoxy}phenyl)-2-phenoxypropionic acid ethyl ester (3.6 mmol) in MeOH (7 mL) was treated with 2N NaOH (7 mL) and warmed to 55° C. After 18 h, the mixture was concentrated under reduced pressure and then acidified with 5N HCl to pH=1. The solution was extracted with EtOAc and then the organic phases dried (Na$_2$SO$_4$), filtered and concentrated to a white solid. $^1$H NMR (400 MHz, DMSO-d$_6$) δ 8.09 (s, 1H), 7.82 (d, J=7.6 Hz, 1H), 7.77 (d, J=7.6 Hz, 1H), 7.62–7.59 (m, 2H), 7.53 (t, J=7.6 Hz, 1H), 7.24 (t, J=7.6 Hz, 2H), 7.17–7.16 (m, 1H), 7.13 (d, J=8.8 Hz, 2H), 6.93 (t, J=8.4 Hz, 1H), 6.85 (d, J=8.4 Hz, 2H), 6.79 (d, J=8.8 Hz, 2H), 4.19 (t, J=6.4 Hz, 2H), 3.16 (d, J=13.6 Hz, 1H), 3.04 (d, J=6.4 Hz, 1H), 2.93 (t, J=6.4 Hz, 2H), 2.49–2.48 (m, 2H), 2.36 s, 3H),1.26 (s, 3H); MS (EI) 540.1 (M+H)+, 538.2 (M–H)–.

Example 6

2-Methyl-3-(4-{2-[5-methyl-2-(3-thiophen-3-ylphenyl)oxazol-4-yl]ethoxy}phenyl)-2-phenoxypropionic acid

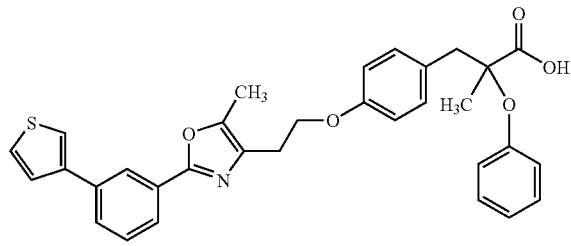

A. 2-[5-Methyl-2-(3-thiophen-3-ylphenyl)oxazol-4-yl]ethanol

2-[2-(3-Bromo-phenyl)-5-methyloxazol-4-yl]ethanol (1.0 g, 3.54 mmol) (see Ex. 2, Part D) and 3-thiophene boronic acid (5.32 mmol) were stirred in n-PrOH (10 mL) under nitrogen, to which 2M Na2CO3 (3.54 mL) was added. The mixture was heated at 85° C., and after Pd(PPh3)4 (41 mg, 0.0354 mmol) was added, the reaction proceeded for 0.5 h. Once the reaction mixture had cooled to room temperature, it was concentrated and taken up in CH2Cl2 (20 mL), then washed with 0.5M NaOH (20 mL). The aqueous layer was back-extracted with CH2Cl2 (10 mL), combined organics were washed with 1M NaOH (10 mL), followed by H2O (10 mL), then dried over Na2SO4, and concentrated to a crude solid. Recrystallized from ethyl acetate:hexanes (1:1) and vacuum oven-dried at 50° C. to yield a tan solid. 1H NMR (400 MHz, CDCl3) δ 8.22 (s, 1H), 7.92 (d, J=8.0 Hz, 1H), 7.62 (d, J=8.0 Hz, 1H), 7.57 (s, 1H), 7.48 (t, J=8.0 Hz, 1H) 7.46(m, 1H), 7.41 (m, 1H), 3.95 (t, J=5.6 Hz, 2H), 2.74 (t, J=5.6 Hz, 1H), 2.36 (s, 3H); MS (EI) 286.1 (M+H)+.

B. Toluene-4-sulfonic acid 2-[5-methyl-2-(3-thiophen-3-ylphenyl)oxazol-4-yl]ethyl ester To a solution of 2-[5-methyl-2-(3-thiophen-3-ylphenyl) oxazol-4-ylethanol (11.6 mmol) in CH2Cl2 (46 mL) at room temperature under N2 was added pyridine (3.28 mL) and DMAP (0.43 g, 3.48 mmol) followed by portionwise addition of tosyl anhydride (4.54 g, 13.9 mmol). The reaction exothermed to 32° C. and was stirred 2 h before 1N HCl (50 mL) was added. The mixture was stirred vigorously 15 min, and then the organic phase was dried (MgSO4) and then concentrated under reduced pressure. The residue was purified by column chromatography (40 mL SiO2, 50% EtOAc/hexanes) to provide toluene-4-sulfonic acid 2-[5-methyl-2-(3-thiophen-3-ylphenyl)oxazol-4-yl]ethyl ester: 1H NMR (400 MHz, CDCl3) δ 8.11 (s, 1H), 7.43 (d, J=7.6 Hz, 1H), 7.67 (d, J=8.4 Hz, 2H), 7.64 (m, 1H), 7.56–7.44 (m, 1H), 7.48–7.42 (m, 3H), 7.17 (d, J=8.4 Hz, 2H), 4.33 (t, J=6.2 Hz, 2H), 2.84 (t, J=6.2 Hz, 1H), 2.33 (s, 3H), 2.18 (s, 3H); MS (EI) 440.1 (M+H)+.

C. 2-Methyl-3-(4-{2-[5-methyl-2-(3-thiophen-3-ylphenyl)oxazol-4-yl]ethoxy}phenyl)-2-phenoxypropionic acid ethyl ester 3-(4-Hydroxyphenyl)-2-methyl-2-phenoxypropionic acid ethyl ester (495 mg, 1.7 mmol) (see Ex. 1, Part C), toluene-4-sulfonic acid 2-[5-methyl-2-(3-thiophen-3-ylphenyl)oxazol-4-yl]ethyl ester (2.2 mmol) and Cs2CO3 (700 mg, 2.2 mmol) are combined in anhydrous DMF (25 mL) and stirred for 16 h at 55° C. under an atmosphere of nitrogen. The mixture was then cooled and diluted with ethyl acetate (100 mL), and washed with water then brine. The organic layer was dried with Na2SO4 and concentrated in vacuo to a viscous yellow oil. The residue was purified by flash column chromatography (100 g silica, 60×15 mL fractions, gradient elution 0–20% ethyl acetate in hexanes) to provide the title compound as a colorless oil. 1H NMR (400 MHz, CDCl3) δ 8.23 (s, 1H), 7.90 (dt, J=7.6 Hz, J=1.2 Hz, 1H), 7.64 (dt, J=7.6 Hz, J=1.2 Hz, 1H), 7.56–7.55 (m, 1H), 7.48–7.39 (m, 3H), 7.23–7.14 (m, 5H), 6.96 (t, J=7.2 Hz, 1H), 6.83–6.81 (m, 4H), 4.24 (t, J=6.8 Hz, 2H), 4.12 (q, J=7.2 Hz, 2H), 3.26 (d, J=14.0 Hz, 1H), 3.10 (d, J=14.0 Hz, 1H), 3.00 (t, J=6.4 Hz, 2H), 2.39 (s, 3H), 1.38 (s, 3H) 1.21 (t, J=7.2 Hz, 3H); MS (EI) 568.2 (M+H)+.

D. 2-Methyl-3-(4-{2-[5-methyl-2-(3-thiophen-3-ylphenyl)oxazol-4-yl]ethoxy}phenyl)-2-phenoxypropionic acid 2-Methyl-3-(4-{2-[5-methyl-2-(3-thiophen-3-ylphenyl)oxazol-4-yl]ethoxy}phenyl)-2-phenoxypropionic acid ethyl ester (3.6 mmol) in MeOH (7 mL) was treated with 2N NaOH (7 mL) and warmed to 55° C. After 18 h, the mixture was concentrated under reduced pressure and then acidified with 5N HCl to pH=1. The solution was extracted with EtOAc and then the organic phases dried (Na2SO4), filtered and concentrated to a white solid. 1H NMR (400 MHz, DMSO-d6) δ8.15 (t, J=1.6 Hz, 1H), 7.98 (dd, J=2.8 Hz, J=1.6 Hz, 1H), 7.82–7.79 (m, 2H), 7.66 (dd, J=7.6 Hz, J=2.8 Hz, 1H), 7.59 (dd, J=6.4 Hz, J=1.2 Hz, 1H), 7.52 (t, J=7.6 Hz, 1H), 7.24 (t, J=8.0 Hz, 2H), 7.13 (d, J=8.4 Hz, 2H), 6.93 (t, J=7.6 Hz, 1H), 6.85 (d, J=8.4 Hz, 1H), 6.79 (dd, J=7.6 Hz, J=1.2 Hz, 2H), 4.19 (t, J=6.4 Hz, 2H), 3.16 (d, J=13.2 Hz, 1H), 3.04 (d, J=13.2 Hz, 1H), 2.92 (t, J=6.4 Hz, 2H), 2.36 (s, 3H), 1.26 (s, 3H); MS (EI) 540.2 (M+H)+, 538.3 (M–M)–.

Example 7

3-{4-[2-(2-Biphenyl-4-yl-5-methyloxazol-4-yl)ethoxy]-3-methoxyphenyl}-2-methyl-2-phenoxypropionic acid

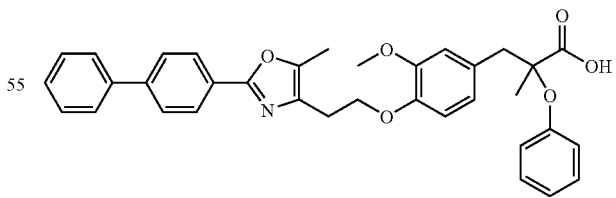

A. 3-(4-Benzyloxy-3-methoxyphenyl)-3-hydroxy-2-methyl-2-phenoxypropionic acid

A stirred solution of LDA in cyclohexane (1.5 M) was cooled to –20° C., to which a solution of 2-phenoxypropionic acid (10 g, 60.2 mmol) in THF (80.3 mL) was slowly added, keeping the temperature below –10° C. The resulting dianion solution was stirred for 15 min, then a solution of 4-benzyloxy-3-methoxybenzaldehyde (14.58 g, 60.2 mmol) in THF (80.3 mL) was added over 1 h, maintaining temperature below −10° C. Fifteen minutes after completion of aldehyde addition, the reaction mixture was poured onto ice water (200 mL), and extracted using 1:2 $Et_2O$:hexane (500 mL). The aqueous layer was isolated, extracted again with 1:2 $Et_2O$:hexane (240 mL), then acidified with concentrated HCl until pH=3. The product acid was extracted into ethyl acetate (2×165 mL), which was dried over $Na_2SO_4$ and concentrated to an orange paste (16.5 g crude, 67%): MS (EI) 426.2 $(M+NH_4)^+$, 407.2 $(M-H)^-$.

B. 3-(4-Benzyloxy-3-methoxyphenyl)-2-methyl-2-phenoxypropionic acid

A stirred solution of $Et_3SiH$ (8.67 mL, 54.3 mmol) in $CH_2Cl_2$ (45 mL) was treated with $BF_3.Et_2O$ (6.8 mL, 54.3 mmol). 3-(4-Benzyloxy-3-methoxyphenyl)-3-hydroxy-2-methyl-2-phenoxypropionic acid (7.39 g, 18.1 mmol) in $CH_2Cl_2$ (90.5 mL) was then added dropwise via addition funnel, maintaining temperature below −7° C. After the addition was complete, the reaction was stirred for 1.5 h at −10° C., then quenched with 1 M NaOH (18.1 mL) and diluted with $H_2O$ (12 mL). 1N HCl was used to adjust pH to 4, followed by separation of layers. The aqueous layer was extracted with $CH_2Cl_2$ (2×15 mL), and combined organic layers were washed first with 1N HCl (15 mL), then $H_2O$ (15 mL), followed by drying over $Na_2SO_4$ and concentration to a gummy orange solid (6.86 g, 97%): MS (EI) 410.2 $(M+NH_4)^+$, 391.3 $(M-H)^-$.

C. 3-(4-Hydroxy-3-methoxy-phenyl)-2-methyl-2-phenoxypropionic acid

A solution of 3-(4-benzyloxy-3-methoxyphenyl)-2-methyl-2-phenoxypropionic acid (6.86 g, 17.5 mmol) in EtOH (175 mL) was added to 5% Pd/C (186 mg, 10 wt %). The mixture was purged first with nitrogen, then with $H_2$, which was then applied at 45 p.s.i. for 2 h. Pd/C was subsequently filtered off through celite, and the filtrate was concentrated to a crude oil (5.42 g, in excess of theory). MS (EI) 301.2 $(M-H)^-$.

D. 3-(4-Hydroxy-3-methoxyphenyl)-2-methyl-2-phenoxypropionic acid ethyl ester

A solution of 3-(4-hydroxy-3-methoxyphenyl)-2-methyl-2-phenoxy-propionic acid (4.56 g, 15.08 mmol) in EtOH (150 mL) was treated with $SOCl_2$ and heated at 75° C. for 14 h, then cooled to room temperature and partitioned between ethyl acetate (300 mL) and $H_2O$ (400 mL). The aqueous layer was removed and back-extracted with ethyl acetate (100 mL). Combined organic phases were washed with 10% $Na_2CO_3$, which was isolated and back-extracted with EtOAc (100 mL). Combined organic phases were washed with brine (200 mL), dried over $Na_2SO_4$, concentrated, and purified by column chromatography (200 g $SiO_2$, 1:4 ethyl acetate:hexanes) to provide a colorless oil, which developed a green color over a 24-hour period. The material was taken up in ethyl acetate and filtered through celite, then concentrated to yield a colorless oil (1.99 g, 40%): Rf=0.40 in 1:4 ethyl acetate:hexanes; $^1H$ NMR (400 MHz, $CDCl_3$) δ 7.66–7.55(m, 1H), 7.25–7.21 (m, 2H), 6.99–6.92 (m, 1H) 6.84–6.79 (m, 3H), 6.74–6.71 (m, 1H), 5.54 (s, 1H), 4.22 (q, J=6.8 Hz, 2H), 3.84 (s, 3H), 3.30 (d, J=14 Hz, 1H), 3.07 (d, J=14 Hz, 1H), 1.40 (s, 3H), 1.23 (t, J=6.8 Hz, 3H).

E. 3-{4-[2-(2-Biphenyl-4-yl-5-methyloxazol-4-yl)ethoxy]-3-methoxyphenyl}-2-methyl-2-phenoxypropionic acid Toluene-4-sulfonic acid 2-(2-biphenyl-4-yl-5-methyl-oxazol-4-yl)-ethyl ester (0.132 mmol) (see Ex. 1, Part I) was added to a one dram, screw-cap vial and diluted with ethanol (0.5 mL). To this solution are added 3-(4-hydroxy-3-methoxyphenyl)-2-methyl-2-phenoxypropionic acid ethyl ester (0.5 mL of a 0.264 M solution in ethanol, 0.132 mmol) and polystyrene bound 1,5,7-triazabicyclo[4.4.0]dec-5-ene (100–125 mg, 2.6 mmol/g) and the vial was tightly closed. The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100 µl) and the vial resealed tightly. The solution was heated in a block heater at 55° C. for 3–16 h, or until MS analysis indicates the completion of the hydrolysis. The solvents are removed with a stream of nitrogen or under reduced pressure and the residue redissolved in 1 mL water. The solution was acidified with aqueous HCl (5N solution, 150 µl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by mass directed HPLC to provide analytically pure material. MS (EI) 564.4 $(M+H)^+$.

Example 8

3-{4-[2-(2-Biphenyl-3-yl-5-methyloxazol-4-yl)ethoxy]-3-methoxyphenyl}-2-methyl-2-phenoxypropionic acid

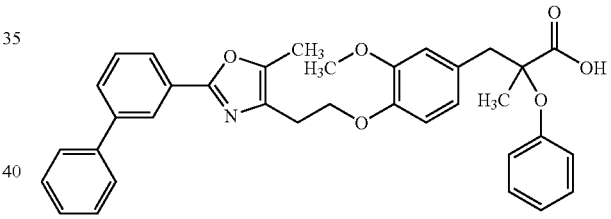

Toluene-4-sulfonic acid 2-(2-biphenyl-3-yl-5-methyl-oxazol-4-yl)-ethyl ester (0.132 mmol) (see Ex. 2, Part F) was added to a one dram, screw-cap vial and diluted with ethanol (0.5 mL). To this solution are added 3-(4-hydroxy-3-methoxyphenyl)-2-methyl-2-phenoxypropionic acid ethyl ester (see Ex. 7, Part D) (0.5 mL of a 0.264 M solution in ethanol, 0.132 mmol) and polystyrene bound 1,5,7-triazabicyclo[4.4.0]dec-5-ene (100–125 mg, 2.6 mmol/g) and the vial was tightly closed. The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100 µl) and the vial resealed tightly. The solution was heated in a block heater at 55° C. for 3–16 h, or until MS analysis indicates the completion of the hydrolysis. The solvents are removed with a steam of nitrogen or under reduced pressure and the residue redissolved in 1 mL water. The solution was acidified with aqueous HCl (5N solution, 150 µl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by mass-directed HPLC to provide analytically pure material. MS (EI) 564.4 (M+H)+.

Example 9

3-(3-Methoxy-4-{2-[5-methyl-2-(4-thiophen-2-ylphenyl)oxazol-4-yl]ethoxy}phenyl)-2-methyl-2-phenoxypropionic acid

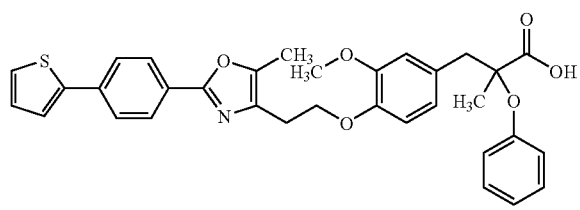

Toluene-4-sulfonic acid 2-(5-methyl-2-(4-thiophen-2-yl-phenyl)-oxazol-4-yl)ethyl ester (0.132 mmol) (see Ex. 3, Part B) was added to a one dram, screw-cap vial and diluted with ethanol (0.5 mL). To this solution are added 3-(4-hydroxy-3-methoxyphenyl)-2-methyl-2-phenoxypropionic acid ethyl ester(see Ex. 7, Part D) (0.5 mL of a 0.264 M solution in ethanol, 0.132 mmol) and polystyrene bound 1,5,7-triazabicyclo[4.4.0]dec-5-ene (100–125 mg, 2.6 mmol/g) and the vial was tightly closed. The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100 µl) and the vial resealed tightly. The solution was heated in a block heater at 55° C. for 3–16 h, or until MS analysis indicates the completion of the hydrolysis. The solvents are removed with a stream of nitrogen or under reduced pressure and the residue redissolved in 1 mL water. The solution was acidified with aqueous HCl (5N solution, 150 µl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by mass-directed HPLC to provide analytically pure material. MS (EI) 570.4 (M+H)+.

Example 10

3-{4-[2-(2-Biphenyl-3-yl-5-methyl-oxazol-4-yl)ethoxy]-3-propyl-phenyl}-2-methyl-2-phenoxy-propionic acid

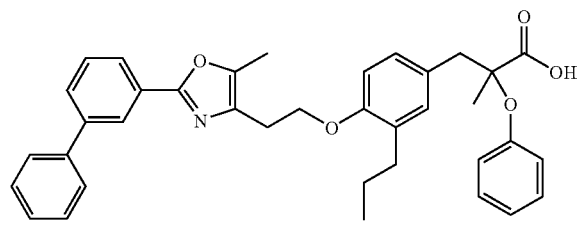

A. 3-(4-Allyloxyphenyl)-2-methyl-2-phenoxy-propionic acid ethyl ester

A solution of 3-(4-hydroxyphenyl)-2-methyl-2-phenoxy-propionic acid ethyl ester (500 mg, 1.67 mmol) in methyl ethyl ketone (6 mL) was treated with allyl bromide (232 mg, 1.92 mmol, 0.17 mL) and potassium carbonate (311 mg, 2.25 mmol) and then heated to reflux. After 18 h, the mixture was cooled to ambient temperature and then partitioned between ethyl acetate and water. The aqueous phase was extracted with ethyl acetate and then the organic phases were dried (MgSO$_4$), filtered and concentrated under reduced pressure. The residue was purified by column chromatography (100 mL SiO$_2$, hexanes to 10% ethyl acetate/hexanes) to provide the desired product (478 mg, 84%) as a clear, colorless oil: $^1$H NMR (400 MHz, CDCl$_3$) δ 7.22 (t, J=8.0 Hz, 2H), 7.16 (d, J=8.8 Hz, 2H), 6.97 (dt, J=7.6, 1.2 Hz, 1H), 6.83 (d, J=7.8 Hz, 2H), 6.84 (t, J=8.4 Hz, 2H), 6.05 (ddd, J=17.2, 10.6, 5.2 Hz, 1H), 5.41 (dd, J=17.2, 1.6 Hz, 1H), 5.28 (dd, J=10.8, 1.4 Hz, 1H), 4.22 (d, J=5.2 Hz, 2H), 4.19 (q, J=6.8 Hz, 2H), 3.27 (A of AB, J=14 Hz, 1H), 3.11 (B of AB, J=14 Hz, 1H), 1.40 (s, 3H), 1.21 (t, J=6.8 Hz, 3H).

B. 3-(3-Allyl-4-hydroxyphenyl)-2-methyl-2-phenoxy-propionic acid ethyl ester

A solution of 3-(4-allyloxyphenyl)-2-methyl-2-phenoxy-propionic acid ethyl ester (475 mg, 1.39 mmol) in dimethylaniline (1.5 mL) was heated at reflux for 18 h. After cooling to ambient temperature, the reaction mixture was partitioned between ethyl acetate and 1N H$_2$SO$_4$. The organic phase was dried (MgSO$_4$), filtered and concentrated. The residue was purified by column chromatography (100 mL SiO$_2$, hexanes to 30% ethyl acetate/hexanes) to provide the desired product (343 mg, 72%) as a pale yellow oil: $^1$H NMR (400 MHz, CDCl$_3$) δ 7.23 (t, J=8.4 Hz, 2H), 7.02–6.96 (m, 3H), 6.83 (d, J=8.8 Hz, 2H), 6.72 (d, J=7.6 Hz, 1H), 6.05 (m, 1H), 5.16–5.09 (m, 2H), 4.21 (q, J=6.8 Hz, 2H), 3.38 (d, J=6.4 Hz, 2H), 3.25 (A of AB, J=13.6 Hz, 1H), 3.10 (B of AB, J=13.6 Hz, 1H), 1.41 (s, 3H), 1.23 (t, J=6.8 Hz, 3H).

C. 3-(4-Hydroxy-3-propylphenyl)-2-methyl-2-phenoxy-propionic acid ethyl ester

A solution of 3-(3-allyl-4-hydroxyphenyl)-2-methyl-2-phenoxy-propionic acid ethyl ester(330 mg, 0.97 mmol) in absolute ethanol (5 mL) was treated with 5% Pd/C and then the mixture was evacuated thee times with N$_2$. The reaction mixture was hydrogenated at 1 atm with an H$_2$-filled balloon for 24 h before filtering the mixture over celite and rinsing with ethanol. The product was used without further purification. $^1$H NMR (400 MHz, CDCl$_3$) δ 7.22 (t, J=7.6 Hz, 2H), 7.99–6.95 (m, 3H), 6.82 (m, 2H), 6.68 (d, J=8.0 Hz, 1H), 4.20 (q, J=6.8 Hz, 2H), 3.24 (A of AB, J=13.6 Hz, 1H), 3.08 (B of AB, J=13.6 Hz, 1H), 2.55 (t, J=7.6 Hz, 2h), 1.62 (sextet, J=7.6 Hz, 2H), 1.41 (s, 3H), 1.23 (t, J=6.8 Hz, 3H), 0.96 (t, J=7.2 Hz, 3H).

D. 3-(4-[2-(2-Biphenyl-3-yl-5-methyl-oxazol-4-yl)-ethoxy]-3-propyl-phenyl}-2-methyl-2-phenoxy-propionic acid ethyl ester A solution of 3-(4-hydroxy-3-propylphenyl)-2-methyl-2-phenoxy-propionic acid ethyl ester (266 mg, 1.0 mmol) in DMF (10 mL) was treated with cesium carbonate (407 mg, 1.25 mmol) and toluene-4-sulfonic acid 2-(2-biphenyl-3-yl-5-methyl-oxazol-4-yl)-ethyl ester (520 mg, 1.20 mmol) (see Ex. 2, Part F) and then heated at 55° C. for 18 h. After cooling to ambient temperature, the mixture was partitioned between ethyl acetate and water. The aqueous phase was extracted with ethyl acetate and then the organic phases were dried (MgSO$_4$), filtered and concentrated under reduced pressure. The residue was purified by column chromatography (100 mL SiO$_2$, hexanes to 30% ethyl acetatelhexanes) to provide the desired product (315 mg, 60%) as a clear, colorless oil: $^1$H NMR (400 MHz, CDCl$_3$) δ 8.24 (s, 1H), 7.97 (d, J=8.0 Hz, 1H), 7.68–7.63 (m, 3H), 7.51 (t, J=7.6 Hz, 1H), 7.46 (t, J=8.0 Hz, 2H), 7.38 (t, J=7.2 Hz, 1H), 7.25–7.21 (m, 2H), 7.04–6.96 (m, 3H), 6.85–6.69 (m, 3H), 4.26 (t, J=6.4 Hz, 2H), 4.21 (q, J=6.8 Hz, 2H), 3.26 (A of AB, J=13.6 Hz, 1H), 3.09 (B of AB, J=13.6 Hz, 1H), 3.01 (t, J=6.4 Hz, 2H), 2.54 (t, J=7.6 Hz, 2H), 2.41 (s, 3H), 1.54 (sextet, J=7.6 Hz, 2H), 1.41 (s, 3H), 1.23 (t, J=6.8 Hz, 3H), 0.91 (t, J=7.2 Hz, 3H); MS (EI) 604.3 (M+H)$^+$.

E. 3-{4-[2-(2-Biphenyl-3-yl-5-methyl-oxazol-4-yl)-ethoxy]-3-propyl-phenyl}-2-methyl-2-phenoxy-propionic acid A solution of 3-{4-[2-(2-biphenyl-3-yl-5-methyl-oxazol-4-yl)-ethoxy]-3-propyl-phonyl}-2-methyl-2-phenoxy-propionic acid ethyl ester in ethanol (1.5 mL) was treated with 5 N NaOH (140 mL) and then warmed to 65° C. After 18 h, the mixture was acidified to pH=1 with 5 N HCl. The mixture was extracted with ethyl acetate and then the combined organic phases were dried (MgSO$_4$), filtered and concentrated under reduced pressure to yield the desired product (61 mg, 91%) as a pale yellow oil: $^1$H NMR (400 MHz, CDCl$_3$) δ 8.24 (s, 1H), 7.95 (d, J=7.6 Hz, 1H), 7.65 (d, J=7.6 Hz, 3H), 7.50–7.36 (m, 4H), 7.20 (t, J=8.4 H, 2H), 7.06–6.89 (m, 5H), 6.74 (d, J=8.0 Hz, 1H), 4.21 (t, J=6.4 Hz, 2H), 3.27 (A of AB, J=13.6 Hz, 1H), 3.12 (B of AB, J=13.6 Hz, 1H), 3.03 (t, J=6.4 Hz, 2H), 2.51 (t, J=7.6 Hz, 2H), 2.41 (s, 3H), 1.51 (sextet, J=7.6 Hz, 2H), 1.41 (s, 3H), 0.88 (t, J=7.2 Hz, 3H).

Example 11

2-Methyl-3-(4-{2-[5-methyl-2-(4-thiophen-2-yl-phenyl)-oxazol-4-yl]-ethoxy}-3-propyl-phenyl)-2-phenoxy-propionic acid

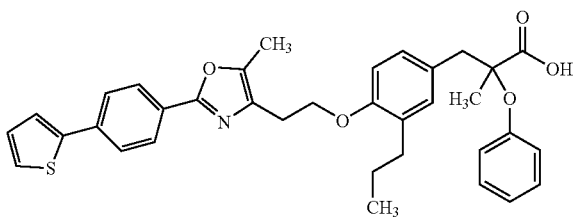

A. 2-Methyl-3-(4-{2-[5-methyl-2-(4-thiophen-2-yl-phenyl)-oxazol-4-yl]-ethoxy}-3-propyl-phenyl)-2-phenoxy-propionic acid Toluene-4-sulfonic acid 2-(5-methyl-2-(4-thiophen-2-yl-phenyl)-oxazol-4-yl)ethyl ester (see Ex. 3, Part B) (0.132 mmol) was added to a one dram, screw-cap vial and diluted with ethanol (0.5 mL). To this solution are added 3-(4-hydroxy-3-propylphenyl)-2-methyl-2-phenoxy-propionic acid ethyl ester (0.5 mL of a 0.264 M solution in ethanol, 0.132 mmol) (see Ex. 10, Part C) and polystyrene bound 1,5,7-triazabicyclo[4.4.0]dec-5-ene (100–125 mg, 2.6 mmol/g) and the vial was tightly closed. The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100 µl) and the vial resealed tightly. The solution was heated in a block heater at 55 ° C. for 3–16 h, or until MS analysis indicates the completion of the hydrolysis. The solvents are removed with a stream of nitrogen or under reduced pressure and the residue redissolved in 1 mL water. The solution was acidified with aqueous HCl (5N solution, 150 µl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by mass-directed HPLC to provide analytically pure material. MS (EI) 582.1 (M+H)$^+$; LC RT=3.56 min (>99% pure).

Example 12

3-{4-[2-(2-Biphenyl-4-yl-5-methyl-oxazol-4-yl)-ethoxy]-naphthalen-1-yl}-2-methyl-2-phenoxypropionic acid

A. 2-Phenoxy-3-(4-benzyloxynaphthalen-1-yl)-2-methyl-propionic acid ethyl ester

A solution of lithium diisopropyl amide (LDA) (3.5 mL, 5.2 mmol, 1.5M in cyclohexane) was added dropwise slowly to a solution of 3-(4-hydroxyphenyl)-2-methyl-2-phenoxypropionic acid ethyl ester (1.0 g, 5.2 mmol) in anhydrous THF (10 mL) which was cooled to −78° C. under an atmosphere of nitrogen. After ten min 4-benzyloxynaphthalene-1-carbaldehyde (1.23 g, 4.7 mmol) in anhydrous THF (5 mL) was added dropwise. After stirring for 30 min, the reaction mixture was quenched with saturated solution of aqueous NH$_4$Cl (10 mL) and the mixture allowed to warm to ambient temperature. The biphasic mixture was diluted with ether (20 mL) and partitioned, and the organic layer was washed with brine, dried over MgSO$_4$ and concentrated in vacuo to provide a viscous golden oil (1.80 g, 81%) as a mixture of inseparable diastereomers of 3-(4-benzyloxynaphthalen-1-yl)-2-phenoxy-3-hydroxy-2-methylpropionic acid ethyl ester which was used without further characterization or purification. R$_f$ (7:3 hexanes:ethyl acetate)=0.51

3-(4Benzyloxynaphthalen-1-yl)-2-phenoxy-3-hydroxy-2-methylpropionic acid ethyl ester (1.80 g, 3.9 mmol) in anhydrous CH$_2$Cl$_2$ (20 mL) was cooled to 0° C. and treated with BF$_3$-Et$_2$O (0.48 mL, 3.9 mmol, d=1.154) and triethylsilane (0.63 mL, 3.9 mmol, d=0.728). The mixture was stirred for 2 hr, gradually warming to ambient temperature. Saturated aqueous Na$_2$CO$_3$ (15 mL) was added and the mixture was stirred vigorously for 15 min. The solution was partitioned and the organic layer was washed twice with water and brine, dried over Na$_2$SO$_4$, and concentrated in vacuo to 3-(4-benzyloxynaphthalen-1-yl)-2-phenoxy-2-methylpropionic acid ethyl ester as a golden oil (1.55 g, 89%). R$_f$=0.41 (9:1 hexanes:ethyl acetate). $^1$H NMR (300 MHz, CDCl$_3$): δ 8.33 (d, 1H, J=8.3), 8.11 (d, 1H, J=8.3), 7.47 (d, 2H, J=7.8), 7.40 (t, 1H, J=8.3), 7.37 (t, 1H, J=8.3), 7.36 (t, 2H, J=7.8) 7.28 (d, 2H, J=7.8), 7.11 (t, 2H, J=8.8), 6.87 (t, 1H, J=7.8), 6.79 (d, 1H, J=7.8), 6.69 (d, 2H, J=8.8), 5.18 (s, 2H, 4.08 (q, 2H, J=7.0), 3.66 (d, 1H, J=14.4), 3.54 (d, 1H, J=14.4), 1.38 (s, 3H), 1.13 (t, 3H, J=7.0). MS [EI+] 458 (M+NH$_4$)$^+$ B. 2-Phenoxy-3-(naphthalen-1-yl)-2-methylpropionic acid ethyl ester 2-Phenoxy-3-(4-benzyloxynaphthalen-1-yl)-2-methylpropionic acid ethyl ester (1.55 g, 3.5 mmol) was dissolved in ethyl acetate (50 mL) and treated with 5% palladium on carbon (400 mg), and stirred under an atmosphere of hydrogen for 20 h. The suspension was filtered through celite and concentrated in vacuo to a golden oil (1.20 g, 98%) $^1$H NMR (300 MHz, CDCl$_3$): δ 8.14 (d, 1H, J=8.3), 8.10 (d, 1H, J=8.3), 7.46 (t, 1H, J=8.3), 7.42 (t, 1H, J=8.3), 7.21 (d, 1H, J=7.8), 7.12 (dd, 2H, J=8.8, 7.4), 6.87 (t, 1H, J=7.4), 6.70 (m, 3H), 4.05 (q, 2H, J=6.8), 3.65 (d, 1H, J=14.2), 3.54 (d, 1H, J=14.2), 1.37 (s, 3H), 1.17 (t, 3H, J=6.8). MS [EI+] 373 (M+Na)$^+$, [EI−] 349 (M−H).

C. 3-{4-[2-(2-Phenyl-5-methyloxazol-4-yl)ethoxy]-naphthalen-1-yl}-2-methyl-2-phenoxypropionic acid ethyl ester Toluene-4-sulfonic acid 2-(5-methyl-2-biphenyl-4-yl-oxazol-4-yl)ethyl ester (0.132 mmol) (see Ex. 1, Part I) was added to a one dram, screw-cap vial and diluted with ethanol (0.5 mL). To this solution are added 2-phenoxy-3-(naphthalen-1-yl)-2-methylpropionic acid ethyl ester (0.5 mL of a 0.264 M solution in ethanol, 0.132 mmol) and polystyrene bound 1,5,7-triazabicyclo[4.4.0]dec-5-ene (100–125 mg, 2.6 mmol/g) and the vial was tightly closed. The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100 µl) and the vial resealed tightly. The solution was heated in a block heater at 55° C. for 3–16 h, or until MS analysis indicates the completion of the hydrolysis. The solvents are removed with a stream of nitrogen or under reduced pressure and the residue dissolved in 1 mL water. The solution was acidified with aqueous HCl (5N solution, 150 µl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by mass-directed HPLC to produce a white solid (2%). MS [EI+] 584 (M+H)$^+$, [EI−] 582 (M−H)$^+$ Example 13

3-{4-[2-(2-Biphenyl-3-yl-5-methyl-oxazol-4-yl)-ethoxy]-naphthalen-1-yl}-2-methyl-2-phenoxypropionic acid

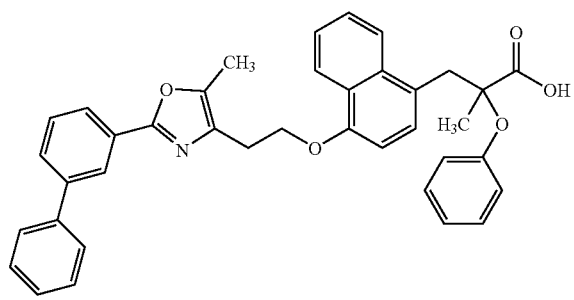

A. 3-{4-[2-(2-Biphenyl-3-yl-5-methyl-oxazol-4-yl)-ethoxy]-naphthalen-1-yl}-2-methyl-2-phenoxypropionic acid Toluene-4-sulfonic acid 2-(2-biphenyl-3-yl-5-methyl-oxazol-4-yl)-ethyl ester (0.132 mmol) (see Ex. 2, Part F) was added to a one dram, screw-cap vial and diluted with ethanol (0.5 mL). To this solution are added 2-phenoxy-3-(naphthalen-1-yl)-2-methylpropionic acid ethyl ester (see Ex. 12, Part B) (0.5 mL of a 0.264 M solution in ethanol, 0.132 mmol) and polystyrene bound 1,5,7-triazabicyclo[4.4.0]dec-5-ene (100–125 mg, 2.6 mmol/g) and the vial was tightly closed. The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100 µl) and the vial resealed tightly. The solution was heated in a block heater at 55° C. for 3–16 h, or until MS analysis indicates the completion of the hydrolysis. The solvents are removed with a stream of nitrogen or under reduced pressure and the residue redissolved in 1 mL water. The solution was acidified with aqueous HCl (5N solution, 150 µl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by mass-directed HPLC to produce a white solid (24%). MS [EI+] 584 (M+H)$^+$, [EI−] 582 (M−H)$^+$ Example 14

2-Methyl-3-(4-{2-[5-methyl-2-(4-thiophen-2-yl-phenyl)-oxazol-4-yl]-ethoxy}-naphthalen-1-yl)-2-phenoxypropionic acid

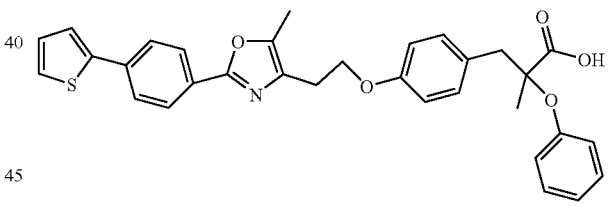

A. 3-{4-[2-(2-Biphenyl-3-yl-5-methyl-oxazol-4-yl)-ethoxy]-naphthalen-1-yl}-2-methyl-2-phenoxypropionic acid Toluene-4-sulfonic acid 2-(5-methyl-2-(4-thiophen-2-yl-phenyl)-oxazol-4-yl)-ethyl ester (0.132 mmol) (see Ex. 3, Part B) was added to a one dram, screw-cap vial and diluted with ethanol (0.5 mL). To this solution are added 2-phenoxy-3-(naphthalen-1-yl)-2-methylpropionic acid ethyl ester (see Ex. 12, Part B) (0.5 mL of a 0.264 M solution in ethanol, 0.132 mmol) and polystyrene bound 1,5,7-triazabicyclo[4.4.0]dec-5-ene (100–125 mg, 2.6 mmol/g) and the vial was tightly closed. The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100·1) and the vial resealed tightly. The solution was heated in a block heater at 55° C. for 3–16 h, or until MS analysis indicates the completion of hew hydrolysis. The solvents are removed with a stream of nitrogen or under reduced pressure and the residue redissolved in 1 mL water. The solution was acidified with aqueous HCl (5N solution, 150·1), often causing precipitation of product. The suspension was diluted with dichloromethane (3 mL) and the resultant biphasic solution was filtered through a Chrom-Elut column to remove water. The filtrate was concentrated in vacuo and the resultant residue was purified by mass-directed HPLC to produce a white solid (7%). MS [EI+] 590 (M+H)$^+$, [EI−] 588 (M−H)$^+$ Example 15

3-{4-[2-(2-Biphenyl-4-yl-5-methyl-oxazol-4-yl)-ethoxy]-phenyl}-2-methyl-2-(4-tert-butylphenoxy)-propionic acid

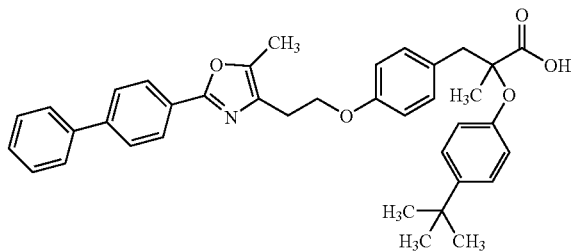

A. 2-(4-tert-Butyl-phenoxy)-propionic acid ethyl ester 4-tert-butylphenol (7.52 g, 50 mmol) in anhydrous DMF (40 mL) was added dropwise to NaH (2.2 g, 55 mmol, 60% w/w in mineral oil) at 0° C. under an atmosphere of nitrogen. After five min, ethyl 2-bromopropionate (6.49 mL, 50 mmol, d=1.394) was added rapidly dropwise and the resultant mixture was allowed to stir for 18 h, gradually warming to ambient temperature. The reaction mixture was diluted with ethyl acetate (300 mL) and extracted twice with water and once with brine. The organic layer was dried over Na$_2$SO$_4$ and concentrated in vacuo to produce a colorless oil (12.5 g, 100%) $^1$H NMR (300 MHz, CDCl$_3$): δ 7.28 (d, 2H, J=5.5), 6.80 (d, 2H, J=5.5), 4.70 (q, 1H, J=6.6), 4.22 (q, 2H, J=7.1), 1.59 (d, 3H, J=6.6), 1.28 (s, 9H), 1.25 (t, 3H, J=7.1). MS [EI+] 251 (M+H)$^+$, 268 (M+NH$_4$)$^+$.

B. 2-(4-tert-Butyl-phenoxy)-3-(4-hydroxyphenyl)-2-methylpropionic acid ethyl ester A solution of LDA (12.7 mL, 19.1 mmol, 1.5M in cyclohexane) was cooled to −78° C. in a dry ice/acetone bath and then added to a solution of 2-(4-tert-butyl-phenoxy)-propionic acid ethyl ester in anhydrous THF (20 mL) also cooled to −78° C. under an atmosphere of nitrogen. After five min, 4-benzyloxybenzaldehyde (3.69 g, 17.4 mmol) was added in one portion. After stirring for 10 min, the reaction mixture was quenched with saturated solution of aqueous NH$_4$Cl (10 mL) and the mixture allowed to warm to ambient temperature. The biphasic mixture was diluted with ether (100 mL) and partitioned, and the organic layer was washed with brine, dried over MgSO$_4$ and concentrated in vacuo. The residue was purified by flash column chromatography (600 g silica, 25×200 mL fractions, gradient elution 0–20% ethyl acetate in hexanes) to provide a colorless oil (3.46 g, 58%) as a mixture of inseparable diastereomers of 3-(4-benzyloxy-phenyl)-2-(4-tert-butyl-phenoxy)-3-hydroxy-2-methylpropionic acid ethyl ester which was used without further characterization or purification.

3-(4-Benzyloxy-phenyl)-2-(4-tert-butyl-phenoxy)-3-hydroxy-2-methylpropionic acid ethyl ester (3.46 g, 7.5 mmol) in anhydrous CH$_2$Cl$_2$ (50 mL) was cooled to 0° C. and treated with pyridine (6.0 mL, 75 mmol, d=0.978). Trifluoroacetic anhydride (2.11 mL, 15 mmol, d=1.487) was added dropwise and the mixture was stirred for 1 h, gradually warming to ambient temperature. The solution was washed twice with 1N HCl and the organic layer dried over Na$_2$SO$_4$ and concentrated in vacuo to produce 3-(4-benzyloxyphenyl)-2-(4-tert-butyl-phenoxy)-3-trifluoroacetoxy-2-methylpropionic acid ethyl ester which was used without characterization.

The material was dissolved in ethyl acetate (50 mL) and treated with 10% palladium on carbon (1.5 g), and stirred under an atmosphere of hydrogen for 48 h. The suspension was filtered through celite and concentrated in vacuo to a golden oil. The residue was purified by flash column chromatography (200 g silica, 30×20 mL fractions, 2% ethyl acetate in CDCl$_3$) to provide the title compound as a colorless oil (1.06 g, two steps 40%) $^1$H NMR (300 MHz, CDCl$_3$): δ 7.21 (d, 2H, J=8.6), 7.12 (d, 2H, J=8.6), 4.19 (q, 1H, J=7.1), 3.24 (d, 1H, J=12.3), 3.11 (d, 1H, J=12.3), 1.38 (s, 3H), 1.27 (s, 9H), 1.23 (t, J=7.1). MS [EI+] 357 (M+H)$^+$, [EI−] 355 (M−H)$^+$.

C. 3-{4-[2-(2-Biphenyl-4-yl-5-methyl-oxazol-4-yl)-ethoxy]-phenyl}-2-methyl-2-(4-tert-butylphenoxy)-propionic acid:

Toluene-4-sulfonic acid 2-(2-biphenyl-4-yl-5-methyl-oxazol-4-yl)-ethyl ester (0.132 mmol) (see Ex. 1, Part I) was added to a one dram, screw-cap vial and diluted with ethanol (0.5 mL). To this solution are added 3-(4-hydroxyphenyl)-2-methyl-2-(4-tert-butylphenoxy)-propionic acid ethyl ester (0.5 mL of a 0.264 M solution in ethanol, 0.132 mmol) and polystyrene bound 1,5,7-triazabicyclo[4.4.0]dec-5-ene (100–125 mg, 2.6 mmol/g) and the vial was tightly closed. The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100 µl) and the vial resealed tightly. The solution was heated in a block heater at 55° C. for 3–16 h, or until MS analysis indicates the completion of the hydrolysis. The solvents are removed with a stream of nitrogen or under reduced pressure and the residue redissolved in 1 mL water. The solution was acidified with aqueous HCl (5N solution, 150 µl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by preparative thin-layer silica chromatography eluting with 93:7 CH$_2$Cl$_2$:methanol to produce a white solid (22%). MS [EI+] 590 (M+H)$^+$, [EI−] 588 (M−H)$^+$

Example 16

3-{4-[2-(2-Biphenyl-3-yl-5-methyl-oxazol-4-yl)-ethoxy]-phenyl}-2-methyl-2-(4-tert-butylphenoxy)-propionic acid

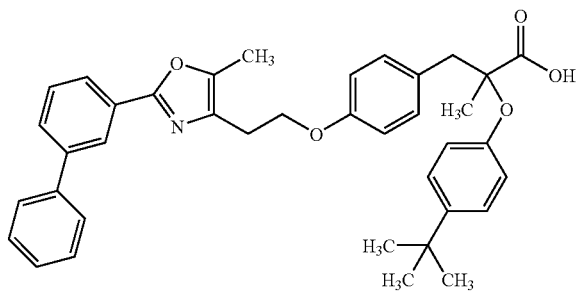

A. 3-{4-[2-(2-Biphenyl-3-yl-5-methyl-oxazol-4-yl)-ethoxy]-phenyl}-2-methyl-2-(4-tert-butylphenoxy)-propionic acid Toluene-4-sulfonic acid 2-(2-biphenyl-3-yl-5-methyl-oxazol-4-yl)-ethyl ester (0.132 mmol) (see Ex. 2, Part F) was added to a one dram, screw-cap vial and diluted with ethanol (0.5 mL). To this solution are added 3-(4-hydroxyphenyl)-2-methyl-2-(4-tert-butylphenoxy)-propionic acid ethyl ester (0.5 mL of a 0.264 M solution in ethanol, 0.132 mmol) (see Ex. 15, Part B) and polystyrene bound 1,5,7-triazabicyclo[4.4.0]dec-5-ene (100–125 mg, 2.6 mmol/g) and the vial was tightly closed. The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100 µl) and the vial resealed tightly. The solution was heated in a block heater at 55° C. for 3–16 h, or until MS analysis indicates the completion of the hydrolysis. The solvents are removed with a stream of nitrogen or under reduced pressure and the residue redissolved in 1 mL water. The solution was acidified with aqueous HCl (5N solution, 150 µl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by preparative thin-layer silica chromatography eluting with 95:5 CH$_2$Cl$_2$:MeOH to produce a white solid (45%). MS [EI+] 590 (M+H)$^+$, [EI−] 588 (M−H)$^+$

Example 17

2-Methyl-3-(4-{2-[5-methyl-2-(4-thiophen-2-yl-phenyl)-oxazol-4-yl]-ethoxy}-phenyl)-2-(4-tert-butylphenoxy)-propionic acid

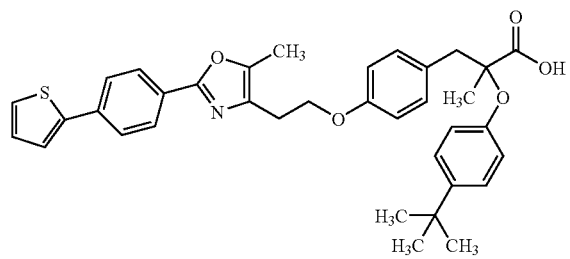

A. 2-Methyl-3-(4-{2-[5-methyl-2-(4-thiophen-2-yl-phenyl)-oxazol-4-yl]-ethoxy}-phenyl)-2-(4-tert-butylphenoxy)-propionic acid Toluene-4-sulfonic acid 2-(5-methyl-2-(4-thiophen-2-yl-phenyl)oxazol-4-yl)-ethyl ester(0.132 mmol) (see Ex. 3, Part B) was added to a one dram, screw-cap vial and diluted with ethanol (0.5 mL). To this solution are added 3-(4-hydroxyphenyl)-2-methyl-2-(4-tert-butylphenoxy)-propionic acid ethyl ester (0.5 mL of a 0.264 M solution in ethanol, 0.132 mmol) (see Ex. 15, Part B) and polystyrene bound 1,5,7-triazabicyclo[4.4.0]dec-5-ene (100–125 mg, 2.6 mmol/g) and the vial was tightly closed. The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100 µl) and the vial resealed tightly. The solution was heated in a block heater at 55° C. for 3–16 h, or until MS analysis indicates the completion of the hydrolysis. The solvents are removed with a stream of nitrogen or under reduced pressure and the residue redissolved in 1 mL water. The solution was acidified with aqueous HCl (5N solution, 150 µl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by preparative thin-layer silica chromatography eluting with 95:5 CH$_2$Cl$_2$:MeOH to produce a white solid (11%). MS [EI+] 596 (M+H)$^+$, [EI−] 594 (M−H)$^+$

Example 18

2-Methyl-3-(4-{2-[5-methyl-2-(3-thiophen-2-yl-phenyl)-oxazol-4-yl]-ethoxy}-phenyl)-2-(4-tert-butylphenoxy)-propionic acid

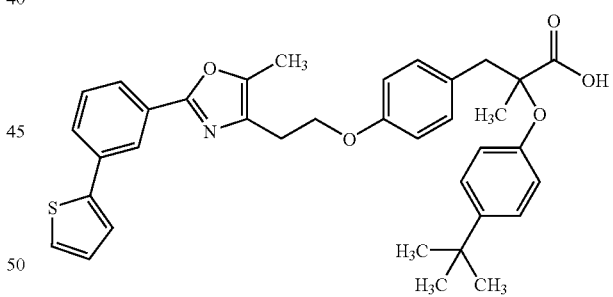

A. 2-Methyl-3-(4-{2-[5-methyl-2-(3-thiophen-2-yl-phenyl)-oxazol-4-yl]-ethoxy}-phenyl)-2-(4-tert-butylphenoxy)-propionic acid:

Toluene-4-sulfonic acid 2-(5-methyl-2-(3-thiophen-2-yl-phenyl)-oxazol-4-yl)-ethyl ester(0.132 mmol) (see Ex. 5, Part B) was added to a one dram, screw-cap vial and diluted with ethanol (0.5 mL). To this solution are added 3-(4-hydroxyphenyl)-2-methyl-2-(4-tert-butylphenoxy)-propionic acid ethyl ester (0.5 mL of a 0.264 M solution in ethanol, 0.132 mmol) (see Ex. 15, Part B) and polystyrene bound 1,5,7-triazabicyclo[4.4.0]dec-5-ene (100–125 mg, 2.6 mmol/g) and the vial was tightly closed. The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100 µl) and the vial resealed tightly. The solution was heated in a block heater at 55° C. for 3–16 h, or until MS analysis indicates the completion of the hydrolysis. The solvents are removed with a stream of nitrogen or under reduced pressure and the residue redissolved in 1 mL water. The solution was acidified with aqueous HCl (5N solution, 150 µl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by preparative thin-layer silica chromatography eluting with 95:5 $CH_2Cl_2$:MeOH to produce a white solid (10%). MS [EI+] 596 (M+H)$^+$, [EI−] 594 (M−H)$^+$ Example 19

2-Methyl-3-(4-{2-[5-methyl-2-(3-thiophen-3-yl-phenyl)-oxazol-4-yl]-ethoxy}-phenyl)-2-(4-tert-butylphenoxy)-propionic acid

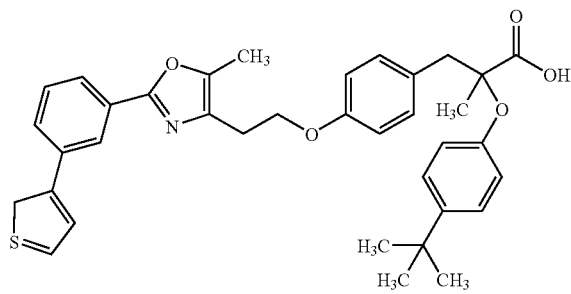

A. 2-Methyl-3-(4-{2-[5-methyl-2-(3-thiophen-3-yl-phenyl)-oxazol-4-yl]-ethoxy}-phenyl)-2-(4-tert-butylphenoxy) -propionic acid:

Toluene-4-sulfonic acid 2-(5-methyl-2-(3-thiophen-3-yl-phenyl)-oxazol-4-yl)-ethyl ester(0.132 mmol) (see Ex. 6, Part B) was added to a one dram, screw-cap vial and diluted with ethanol (0.5 mL). To this solution are added 3-(4-hydroxyphenyl)-2-methyl-2-(4-tert-butylphenoxy)-propionic acid ethyl ester (0.5 mL of a 0.264 M solution in ethanol, 0.132 mmol) (see Ex. 15, Part B) and polystyrene bound 1,5,7-triazabicyclo[4.4.0]dec-5-ene (100–125 mg, 2.6 mmol/g) and the vial was tightly closed. The reaction vessel was heated in a block heater for 24–48 h at 55° C., or until TLC or MS analysis indicates the disappearance of starting materials. The suspension was filtered while warm and the residue washed with ethanol (1 mL). The solution was treated with aqueous NaOH (5N solution, 100 µl) and the vial resealed tightly. The solution was heated in a block heater at 55° C. for 3–16 h, or until MS analysis indicates the completion of the hydrolysis. The solvents are removed with a stream of nitrogen or under reduced pressure and the residue redissolved in 1 mL water. The solution was acidified with aqueous HCl (5N solution, 150 µl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by preparative thin-layer silica chromatography eluting with 95:5 $CH_2Cl_2$:MeOH to produce a white solid (8%). MS [EI+] 596 (M+H)$^+$, [EI−] 594 (M−H)$^+$ Example 20

3-{4-[2-(2-Biphenyl-3-yl-5-methyl-oxazol-4-yl) ethoxy]-phenyl}-2-(3-fluoro-phenoxy)-2-methyl-propionic acid

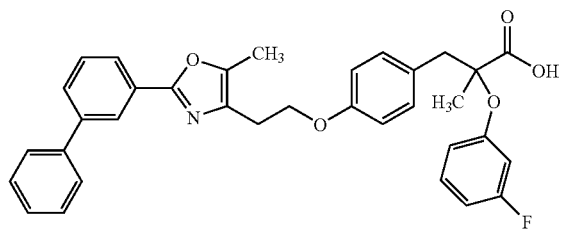

A. 2-(3-Fluorophenoxy)propionic acid ethyl ester

3-Fluorophenol (0.30 mol), $Cs_2CO_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over $Na_2SO_4$ and concentrated in vacuo to produce an oil.

B. 2-(3-Fluorophenoxy)-3-(4-benzyloxyphenyl)-2-methyl-propionic acid ethyl ester A solution of LDA (16.5 mL, 24.7 mmol, 1.5M in cyclohexane) was cooled to −78° C. in a dry ice/acetone bath and then added to a solution 2-(3-fluorophenoxy)propionic acid ethyl ester (24.7 mmol) in anhydrous THF (30 mL) also cooled to −78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous $NH_4Cl$ (10 mL) and the mixture allowed to warm to ambient temperature. The biphasic mixture was diluted with ether (100 mL) and partitioned, and the organic layer was washed with brine, dried over $MgSO_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxy-phenyl)-2-(3-fluoro-phenoxy)-3-hydroxy-2-methylpropionic acid ethyl ester which was used without further characterization or purification.

3-(4Benzyloxyphenyl)-3-hydroxy-2-(3-fluorophenoxy)-2-methylpropionic acid ethyl ester (9.5 mmol) in anhydrous $CH_2Cl_2$ (30 mL) was cooled to 0° C. and treated with $BF_3$-$Et_2O$ (1.16 mL, 9.5 mmol) and triethylsilane (1.51 mL 9.5 mmol). The mixture was stirred for 2 h and gradually warmed to ambient temperature. Saturated aqueous $Na_2CO_3$ (15 mL) was added and the mixture was stirred vigorously. The solution was partitioned and the organic layer was washed twice with water and brine, dried over $Na_2SO_4$, and concentrated in vacuo to produce 3-(4-benzyloxyphenyl)-2-(3-fluorophenoxy)-2-methylpropionic acid ethyl ester as an oil.

C. 2-(3-Fluorophenoxy)-3-(4-hydroxyphenyl)-2-methyl-propionic acid ethyl ester 2-(3-Fluorophenoxy)-3-(4-benzyloxyphenyl)-2-methyl-propionic acid ethyl ester (2.1 mmol) was dissolved in ethyl acetate (30 mL) and treated with 5% palladium on carbon (300 mg), and stirred under an atmosphere of hydrogen for 20 h. The suspension was filtered rough celite and concentrated in vacuo to an oil.

D. 3-{4-[2-(2-Biphenyl-3-yl-5-methyl-oxazol-4-yl)-ethoxy]-phenyl}-2-(3-fluoro-phenoxy)-2-methyl-propionic acid A mixture of 2-(3-fluorophenoxy)-3-(4-hydroxyphenyl)-2-methyl-propionic acid ethyl ester (0.030 mmol), toluene-4-sulfonic acid 2-(2-biphenyl-3-yl-5-methyloxazol-4-yl)ethyl ester (0.030 mmol) (see Ex. 2, Part F) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-{4-[2-(2-Biphenyl-3-yl-5-methyl-oxazol-4-yl)ethoxy]-phenyl}-2-(3-fluoro-phenoxy)-2-methyl-propionic acid $^1$H NMR (400 MHz, CDCl$_3$) δ 8.14 (s, 1H), 7.87 (d, 1H, J=7.8 Hz), 7.57 (d, 2H, J=7.8 Hz), 7.50–7.27 (m, 5H), 7.12 (m, 3H), 6.76 (d, 2H, J=8.6 Hz), 6.72–6.58 (m, 3H), 4.14 (t, 2H, J=6.7 Hz), 3.18 (d, 1H, J=14.1 Hz), 3.08 (d, 1H, J=14.1 Hz), 2.94 (t, 2H, J=6.7 Hz), 2.37 (s, 3H), 1.38 (s, 3H). MS (ES$^+$) m/z mass calcd for $C_{34}H_{31}FNO_5$ 552.21, found 552.2.

Example 21

3-{4-[2-(2-Biphenyl-4-yl-5-methyl-oxazol-4-yl)-ethoxy]-phenyl}-2-(3-fluoro-phenoxy)-2-methyl-propionic acid

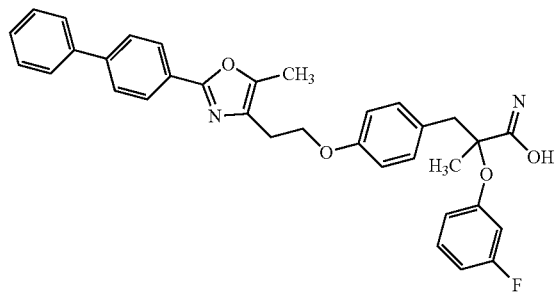

A. 3-{4-[2-(2-Biphenyl-4-yl-5-methyl-oxazol-4-yl)-ethoxy]-phenyl}-2-(3-fluoro-phenoxy)-2-methyl-propionic acid A mixture of 2-(3-fluoro-phenoxy)-3-(4-hydroxyphenyl)-2-methyl-propionic acid ethyl ester (0.030 mmol) (see Ex. 20, Part C), toluene-4-sulfonic acid 2-(5-methyl-2-biphenyl-4-yl-oxazol-4-yl)ethyl ester (0.030 mmol) (see Ex. 1, Part I) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-(3-fluoro-phenoxy)-2-methyl-propionic acid $^1$H NMR (400 MHz, CDCl$_3$) δ 8.06 (d, 2H, J=8.2 Hz), 7.71 (d, 2H, J=8.2 MHz), 7.63 (d, 2H, J=7.0 Hz), 7.47 (t, 2H, J=7.6 Hz), 7.41–7.38 (m, 1H), 7.21–7.15 (m, 3H), 6.82 (d, 2H, J=8.6 Hz), 6.76–6.60 (m, 3H), 4.22 (t, 2H, J=6.3 Hz), 3.27 (d, 1H, J=14.1 Hz), 3.13 (d, 1H, J=14.1 Hz), 3.08 (t, 2H, J=6.3 Hz), 2.45 (s, 3H), 1.44 (s, 3H). MS (ES$^+$) m/z exact mass calcd for $C_{34}H_{30}FNO_5$ 552.2186, found 552.2183.

Example 22

2-(3-Fluoro-phenoxy)-2-methyl-3-(4-{2-[5-methyl-2-(4-thiophen-2-yl-phenyl)-oxazol-4-yl]-ethoxy}-phenyl)-propionic acid

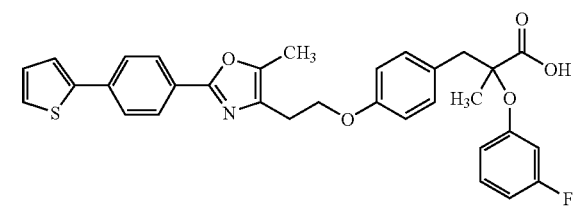

A. 2-(3-Fluoro-phenoxy)-2-methyl-3-(4-{2-[5-methyl-2-(4-thiophen-2-yl-phenyl)-oxazol-4-yl]-ethoxy}-phenyl)-propionic acid A mixture of 2-(3-fluoro-phenoxy)-3-(4-hydroxyphenyl)-2-methyl-propionic acid ethyl ester (0.030 mmol), toluene-4-sulfonic acid 2-(5-methyl-2-(4-thiophen-2-yl-phenyl)-oxazol-4-yl)ethyl ester (0.030 mmol) (see Ex. 3, Part B) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-(3-fluoro-phenoxy)-2-methyl-3-(4-{2-[5-methyl-2-(4-thiophen-2-yl-phenyl)-oxazol-4-yl]-ethoxy}-phenyl)-propionic acid. $^1$H NMR (400 MHz, CDCl$_3$) δ 7.99 (d, 2H, J=8.6 Hz), 7.70 (d, 2H, J=8.6 Hz), 7.42 (dd, 1H, J=3.5 Hz, 1.17 Hz), 7.36 (dd, 1H, J=5.1 Hz, 1.17 Hz), 7.18–7.10 (m, 4H), 6.82 (d, 2H, J=8.6 Hz), 6.76–6.60 (m, 3H), 4.21 (t, 2H, J=6.3 Hz), 3.26 (d, 1H, J=14.1 Hz), 3.12 (d, 1H, J=14.1 Hz), 3.07 (t, 2H, J=6.3 Hz), 2.73 (s, 3H), 1.45 (s, 3H). HRMS (ES$^+$) m/z exact mass calcd for $C_{32}H_{28}FNO_5S$ 558.1750, found 558.1743.

Example 23

3-}4-[2-(2-Biphenyl-4-yl-5-methyl-oxazol-4-yl)-ethoxy]-phenyl}-2-(3-tert-butyl-phenoxy)-2-methyl-propionic acid

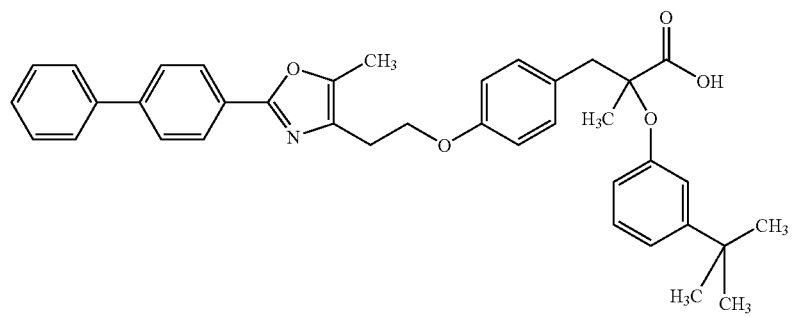

A. 2-(3-tert-Butyl-phenoxy)-propionic acid ethyl ester 3-tert-Butylphenol (7.52 g, 50 mmol) in anhydrous DMF (40 mL) was added dropwise to NaH (2.2 g, 55 mmol, 60% w/w in mineral oil) at 0° C. under an atmosphere of nitrogen. After five min, ethyl 2-bromopropionate (6.49 mL, 50 mmol, d=1.394) was added rapidly dropwise and the resultant mixture was allowed to stir for 18 h, gradually warming to ambient temperature. The reaction mixture was diluted with ethyl acetate (300 mL) and extracted twice with water and once with brine. The organic layer was dried over $Na_2SO_4$ and concentrated in vacuo to produce a colorless oil.

B. 2-(3-tert-Butyl-phenoxy)-3-(4-hydroxyphenyl)-2-methylpropionic acid ethyl ester A solution of LDA (12.7 mL, 19.1 mmol, 1.5M in cyclohexane) was cooled to –78° C. in a dry ice/acetone bath and then added to a solution of 2-(3-tert-butyl-phenoxy)-propionic acid ethyl ester in anhydrous THF (20 mL) also cooled to –78° C. under an atmosphere of nitrogen After five min, 4-benzyloxybenzaldehyde (3.69 g, 17.4 mmol) was added in one portion. After stirring for 10 min, the reaction mixture was quenched with saturated solution of aqueous $NH_4Cl$ (10 mL) and the mixture allowed to warm to ambient temperature. The biphasic mixture was diluted with ether (100 mL) and partitioned, and the organic layer was washed with brine, dried over $MgSO_4$ and concentrated in vacuo. The residue was purified by flash column chromatography (600 g silica, 25×200 mL fractions, gradient elution 0–20% ethyl acetate in hexanes) to provide a colorless oil (3.46 g, 58%) as a mixture of inseparable diastereomers of 3-(4-benzyloxy-phenyl)-2-(3-tert-butyl-phenoxy)-3-hydroxy-2-methylpropionic acid ethyl ester which was used without further characterization or purification.

3-(4-Benzyloxy-phenyl)-2-(4-tert-butyl-phenoxy)-3-hydroxy-2-methylpropionic acid ethyl ester (3.46 g, 7.5 mmol) in anhydrous $CH_2Cl_2$ (50 mL) was cooled to 0° C. and treated with pyridine (6.0 mL, 75 mmol, d=0.978). Trifluoroacetic anhydride (2.11 mL, 15 mmol, d=1.487) was added dropwise and the mixture was stirred for 1 h, gradually warming to ambient temperature. The solution was washed twice with 1N HCl and the organic layer dried over $Na_2SO_4$ and concentrated in vacuo to produce 3-(4-benzyloxyphenyl)-2-(3-tert-butyl-phenoxy)-3-trifluoroacetoxy-2-methylpropionic acid ethyl ester which was used without characterization.

The material was dissolved in ethyl acetate (50 mL) and treated with 10% palladium on carbon (1.5 g), and stirred under an atmosphere of hydrogen for 48 h. The suspension was filtered through celite and concentrated in vacuo to a golden oil. The residue was purified by flash column chromatography (200 g silica, 30×20 mL fractions, 2% ethyl acetate in $CHCl_3$) to provide the title compound as a colorless oil.

C. 3-{4-[2-(2-Biphenyl-4-yl-5-methyl-oxazol-4-yl)-ethoxy]-phenyl}-2-(3-tert-butyl-phenoxy)-2-methyl-propionic acid A mixture of 2-(3-tert-butyl-phenoxy)-3-(4-hydroxyphenyl)-2-methylpropionic acid ethyl ester (0.030 mmol) toluene-4-sulfonic acid 2-(5-methyl-2-biphenyl-4-yl-oxazol-4-yl)ethyl ester (0.030 mmol) (see Ex. 1, Part I) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-(3-tert-butyl-phenoxy)-2-methyl-propionic acid. $^1$H NMR (400 MHz, $CDCl_3$) δ 8.05 (d, 2H, J=8.21 Hz), 7.68 (d, 2H, J=8.21 Hz), 7.63 (d, 2H, J=7.04 Hz), 7.46 (t, 2H, J=7.04 Hz), 7.40–7.36 (m, 1H), 7.20–7.15 (m, 3H), 7.07 (d, 1H, J=7.04 Hz), 6.90 (s, 1H), 6.83 (d, 2H, J=8.60 Hz), 6.71 (dd, 1H, J=8.21 Hz, 2.74 Hz), 4.23 (t, 2H, J=6.26 Hz), 3.25 (d, 1H, J=14.08 Hz), 3.15 (d, 1H, J=14.08 Hz), 3.05 (t, 2H, J=6.26 Hz), 2.42 (s, 3H), 1.43 (s, 3H), 1.26 (s, 9H). HRMS (ES$^+$) m/z exact mass calcd for $C_{38}H_{40}NO_5$ 590.2906, found 590.2891.

Example 24

2-(3-tert-Butyl-phenoxy)-2-methyl-3-(4-{2-[5-methyl-2-(4-thiophen-2-yl-phenyl)-oxazol-4-yl]-ethoxy}-phenyl)-propionic acid

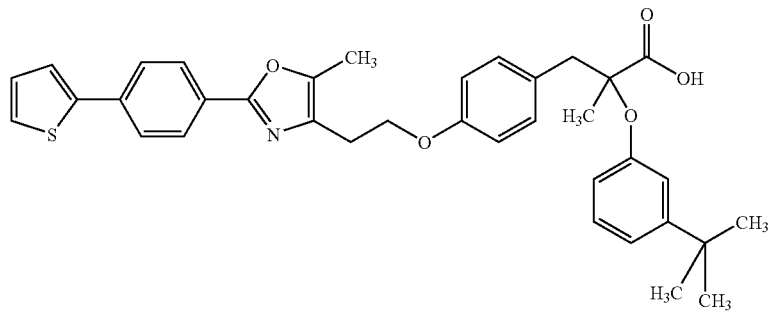

A. 2-(3-tert-Butyl-phenoxy)-2-methyl-3-(4-{2-[5-methyl-2-(4-thiophen-2-yl-phenyl)-oxazol-4-yl]-ethoxy}-phenyl)-propionic acid A mixture of 2-(3-tert-butyl-phenoxy)-3-(4-hydroxyphenyl)-2-methylpropionic acid ethyl ester (0.030 mmol) (see Ex. 23, Part B), toluenesulfonic acid 2-(5-methyl-2-(4-thiophen-2-yl-phenyl)-oxazol-4-yl)ethyl ester (0.030 mmol) (see Ex. 3, Part B) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-(3-tert-butyl-phenoxy)-2-methyl-3-(4-{2-[5-methyl-2-(4-thiophen-2-yl-phenyl)-oxazol-4-yl]-ethoxy)-phenyl)-propionic acid. $^1$H NMR (400 MHz, CDCl$_3$) δ 7.97 (d, 2H, J=8.60 Hz), 7.67 (d, 2H, J=8.60 Hz), 7.36 (dd, 1H, J=3.91 Hz, 1.17 Hz), 7.33 (dd, 1H, J=3.91 Hz, 1.17 Hz), 7.20–7.16 (m, 3H), 7.12–7.07 (m, 2H), 6.89 (t, 1H, J=1.96 Hz), 6.84 (d, 2H, J=8.60 Hz), 6.72 (dd, 1H, J=8.60 Hz, 2.74 Hz), 4.22 (t, 2H, J=6.65 Hz), 3.25 (d, 1H, J=14.08 Hz), 3.15 (d, 1H, J=14.08 Hz), 3.01 (t, 2H, J=6.65 Hz), 2.40 (s, 3H), 1.43 (s, 3H), 1.26 (s, 9H). HRMS (ES$^+$) m/z exact mass calcd for $C_{36}H_{38}NO_5S$ 596.2471, found 596.2454.

Example 25

2-(2-Fluoro-phenoxy)-2-methyl-3-(4-{2-[5-methyl-2-(4-thiophen-2-yl-phenyl)-oxazol-4-yl]-ethoxy}-phenyl)-propionic acid

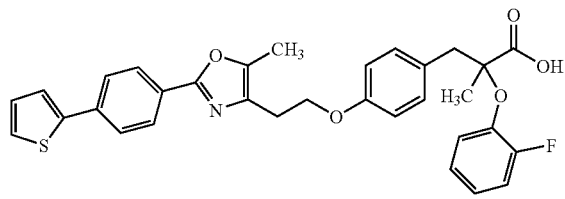

A. 2-(2-Fluorophenoxy)propionic acid ethyl ester

2-Fluorophenol (0.30 mol), $Cs_2CO_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over $Na_2SO_4$ and concentrated in vacuo to produce an oil.

B. 2-(2-Fluorophenoxy)-3-(4-benzyloxyphenyl)-2-methylpropionic acid ethyl ester

A solution of LDA (16.5 mL, 24.7 mmol, 1.5M in cyclohexane) was cooled to −78° C. in a dry ice/acetone bath and then added to a solution 2-(2-fluorophenoxy)propionic acid ethyl ester (24.7 mmol) in anhydrous THF (30 mL) also cooled to −78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous NH$_4$Cl (10 mL) and the mixture allowed to warm to ambient temperature. The biphasic mixture was diluted with ether (100 mL) and partitioned, and the organic layer was washed with brine, dried over MgSO$_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxy-phenyl)-2-(2-fluorophenoxy)-3-hydroxy-2-methylpropionic acid ethyl ester which was used without further characterization or purification.

3-(4-Benzyloxyphenyl)-3-hydroxy-2-(2-fluorophenoxy)-2-methylpropionic acid ethyl ester (9.5 mmol) in anhydrous $CH_2Cl_2$ (30 mL) was cooled to 0° C. and treated with BF$_3$-Et$_2$O (1.16 mL, 9.5 mmol) and triethylsilane (1.51 mL, 9.5 mmol). The mixture was stirred for 2 h and gradually warmed to ambient temperature. Saturated aqueous $Na_2CO_3$ (15 mL) was added and the mixture was stirred vigorously. The solution was partitioned and the organic layer was washed twice with water and brine, dried over $Na_2SO_4$, and concentrated in vacuo to produce 3-(4-benzyloxyphenyl)-2-(2-fluorophenoxy)-2-methylpropionic acid ethyl ester as an oil.

C. 2-(2-Fluorophenoxy)-3-(4-hydroxyphenyl)-2-methyl-propionic acid ethyl ester 2-(2-Fluorophenoxy-3-(4-benzyloxyphenyl)-2-methyl-propionic acid ethyl ester (2.1 mmol) was dissolved in ethyl acetate (30 mL) and treated with 5% palladiun on carbon (300 mg), and stirred under an atmosphere of hydrogen for 20 h. The suspension was filtered through celite and concentrated in vacuo to an oil.

D. 2-(2-Fluoro-phenoxy)-2-methyl-3-(4-{2-[5-methyl-2-(4-thiophen-2-yl-phenyl)-oxazol-4-yl]-ethoxy}-phenyl)-propionic acid A mixture of 2-(2-fluoro-phenoxy)-3-(4-hydroxyphenyl)-2-methyl-propionic acid ethyl ester (0.030 mmol), toluene-4-sulfonic acid 2-(5-methyl-2-(4-thiophen-2-yl-phenyl)-oxazol-4-yl)ethyl ester (0.030 mmol) (see Ex. 3, Part B) and 325 mesh K$_2$CO$_3$ (0.084 g, 0.60 mmol) in ethanol (2 mL) was heated to reflux for 24 h under N$_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and CH$_2$Cl$_2$ and the organic layer dried by passing it through a Varian Chem Elut 1003 cartridge. The solvent was removed in vacuo to give 2-(2-fluoro-phenoxy)-2-methyl-3-(4-{2-[5-methyl-2-(4-thiophen-2-yl-phenyl)-oxazol-4-yl]-ethoxy}-phenyl)-propionic acid. $^1$H NMR (400 MHz, CDCl$_3$) δ 7.96 (d, 2H, J=8.60 Hz), 7.38 (d, 2H, J=3.52 Hz), 7.33 (d, 2H, J=3.52 Hz), 7.23 (d, 2H, J=8.60 Hz), 7.10 (dd, 2H, J=5.08 Hz, 3.52 Hz), 7.08–7.04 (m, 1H), 7.00–6.96 (m, 2H), 6.82 (d, 2H, J=8.60 Hz), 4.19 (t, 2H, J=6.65 Hz), 3.26 (d, 1H, J=14.08 Hz), 3.20 (d, 1H, J=14.08 Hz), 3.01 (t, 2H, J=6.65 Hz), 2.38 (s, 3H), 1.43 (s, 3H). MS (ES$^+$) m/z mass calcd for C$_{32}$H$_{28}$FNO$_5$S 558.17, number found 558.2.

Example 26

2-(4-Chlorophenoxy)-2-methyl-3-(4-{2-[5-methyl-2-(3-thiophen-2-yl-phenyl)-oxazol-4-yl]-ethoxy}-phenyl)-propionic acid

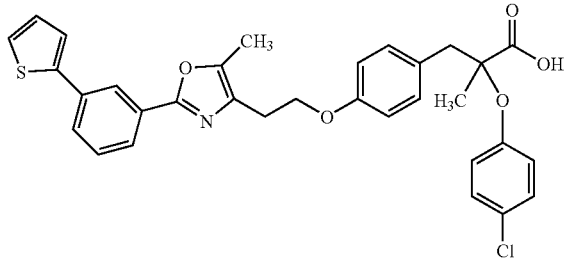

A. 2-(4-Chlorophenoxy)propionic acid ethyl ester

4-Chlorophenol (0.30 mol), Cs$_2$CO$_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over Na$_2$SO$_4$ and concentrated in vacuo to produce an oil.

B. 2-(4-Chlorophenoxy)-3-(4-benzyloxyphenyl)-2-methyl-propionic acid ethyl ester A solution of LDA (16.5 mL, 24.7 mmol, 1.5M in cyclohexane) was cooled to −78° C. in a dry ice/acetone bath and then added to a solution 2-(4-chlorophenoxy)propionic acid ethyl ester (24.7 mmol) in anhydrous THF (30 mL) also cooled to −78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous NH$_4$Cl (10 mL) and the mixture allowed to warm to ambient temperature. The biphasic mixture was diluted with ether (100 mL) and partitioned, and the organic layer was washed with brine, dried over MgSO$_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxy-phenyl)-2-(4-chlorophenoxy)-3-hydroxy-2-methylpropionic acid ethyl ester which was used without further characterization or purification.

3-(4-Benzyloxyphenyl)-3-hydroxy-2-(4-chlorophenoxy)-2-methylpropionic acid ethyl ester (9.5 mmol) in anhydrous CH$_2$Cl$_2$ (30 mL) was cooled to 0° C. and treated with BF$_3$-Et$_2$O (1.16 mL, 9.5 mmol) and triethylsilane (1.51 mL, 9.5 mmol). The mixture was stirred for 2 h and gradually warmed to ambient temperature. Saturated aqueous Na$_2$CO$_3$ (15 mL) was added and the mixture was stirred vigorously. The solution was partitioned and the organic layer was washed twice with water and brine, dried over Na$_2$SO$_4$, and concentrated in vacuo to produce 3-(4-benzyloxyphenyl)-2-(4-chlorophenoxy)-2-methylpropionic acid ethyl ester as an oil.

C. 2-(4-Chlorophenoxy)-3-(4-hydroxyphenyl)-2-methyl-propionic acid ethyl ester 2-(4-Chlorophenoxy-3-(4-benzyloxyphenyl)-2-methyl-propionic acid ethyl ester (2.1 mmol) was dissolved in ethyl acetate (30 mL) and treated with 5% palladium on carbon (300 mg), and stirred under an atmosphere of hydrogen for 1 h. The suspension was filtered through celite and concentrated in vacuo to an oil.

D. 2-(4-Chlorophenoxy)-2-methyl-3-(4-{2-[5-methyl-2-(3-thiophen-2-yl-phenyl)-oxazol-4-yl]-ethoxy}-phenyl)-propionic acid A mixture of 2-(4-chlorophenoxy)-3-(4-hydroxyphenyl)-2-methyl-propionic acid ethyl ester (0.030 mmol), toluene-4-sulfonic acid 2-[5-methyl-2-(3-thiophen-2-ylphenyl)-oxazol-4-yl]ethyl ester (0.030 mmol) (see Ex. 5, Part B) and 325 mesh K$_2$CO$_3$ (0.084 g, 0.60 mmol) in ethanol (2 mL) was heated to reflux for 24 h under N$_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and CH$_2$Cl$_2$ and the organic layer dried by passing it through a Varian Chem Elut 1003 cartridge. The solvent was removed in vacuo to give 2-(4-chlorophenoxy)-2-methyl-3-(4-{2-[5-methyl-2-(3-thiophen-2-yl-phenyl)-oxazol-4-yl]ethoxy}-phenyl)-propionic acid. $^1$H NMR (400 MHz, CDCl$_3$) δ 8.23 (s, 1H), 8.87 (d, 1H, J=8.21 Hz), 7.69–7.67 (m, 1H), 7.46 (d, 1H, J=8.21 Hz), 7.42 (dd, 1H, J=3.52 Hz, 2.74 Hz), 7.32 (dd, 1H, J=5.08 Hz, 2.74 Hz), 7.19–7.15 (m, 3H), 7.18 (dd, 2H, J=6.26 Hz, 2.74 Hz), 6.82 (dd, 4H, J=8.60 Hz, 2.74 Hz), 4.22 (t, 2H, J=6.26 Hz), 3.24 (d, 1H, J=14.08 Hz), 3.10 (d, 1H, J=14.08

Hz), 3.05 (t, 2H, J=6.26 Hz), 2.42 (s, 3H), 1.40 (s, 3H). MS (ES⁺) m/z mass calcd for $C_{32}H_{29}ClNO_5S$ 574.15, found 574.2.

Example 27

3-{4-[2-(2-Biphenyl-4-yl-5-methyl-oxazol-4-yl)-ethoxy]-phenyl}-2-(4-chloro-phenoxy)-2-methyl-propionic acid

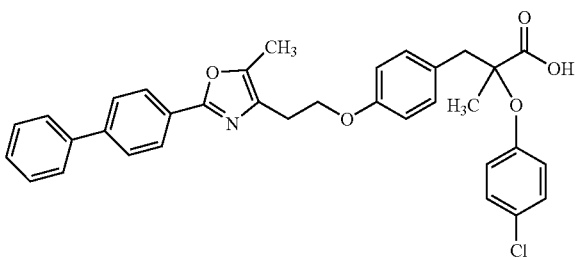

A.  3-{4-[2-(2-Biphenyl-4-yl-5-methyl-oxazol-4-yl)-ethoxy]-phenyl}-2-(4-chloro-phenoxy)-2-methyl-propionic acid A mixture of 2-(4-chlorophenoxy)-3-(4-hydroxyphenyl)-2-methyl-propionic acid ethyl ester (0.030 mmol) (see Ex. 26, Part C), toluene-4-sulfonic acid 2-(5-methyl-2-biphenyl-4-yl-oxazol-4-yl)ethyl ester (0.030 mmol) (see Ex. 1, Part I) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-(4-chloro-phenoxy)-2-methyl-propionic acid. ¹H NMR (400 MHz, CDCl₃) δ 8.05 (d, 2H, J=8.60 Hz), 7.69 (d, 2H, J=8.21 Hz), 7.63 (d, 2H, J=6.65 Hz), 7.48–7.45 (m, 2H), 7.40 (d, 2H, J=7.04 Hz), 7.20–7.15 (m, 4H), 6.82 (d, 3H, J=8.60 Hz), 4.22 (s, 2H), 3.24 (d, 1H, J=13.30 Hz), 3.13–3.07 (m, 3H), 2.43 (s, 3H), 1.25 (s, 3H). MS (ES⁺) m/z mass calcd for $C_{34}H_{31}ClNO_5$ 568.19, found 568.2

Example 28

3-{4-[2-(2-Biphenyl-3-yl-5-methyl-oxazol-4-yl)-ethoxy]-phenyl}-2-(4-chloro-phenoxy)-2-methyl-propionic acid

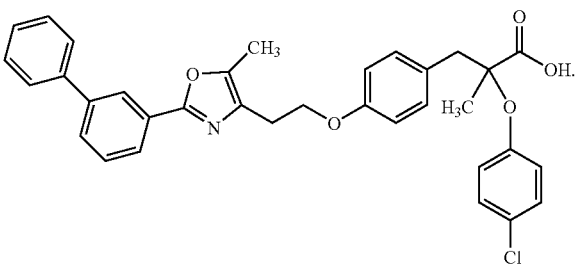

A.  3-{4-[2-(2-Biphenyl-3-yl-5-methyl-oxazol-4-yl)-ethoxy]-phenyl}-2-(4-chloro-phenoxy)-2-methyl-propionic acid A mixture of 2-(4-chlorophenoxy)-3-(4-hydroxyphenyl)-2-methyl-propionic acid ethyl ester (0.030 mmol) (see Ex. 26, Part C), toluene-4-sulfonic acid 2-(2-biphenyl-3-yl-5-methyloxazol-4-yl)ethyl ester (0.030 mmol) (see Ex. 2, Part F) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-(4-chloro-phenoxy)-2-methyl-propionic acid. ¹H NMR (400 MHz, CDCl₃ δ 8.12 (t, 1H, J=19.94 Hz), 7.87 (td, 1H, J=19.16 Hz, 7.43 Hz), 7.61 (t, 3H, J=7.43 Hz), 7.48–7.28 (m, 4H), 7.08 (t, 4H, J=6.65 Hz), 6.77 (td, 4H, J=24.63 Hz, 12.12 Hz), 4.16 (t, 2H, J=6.65 Hz), 3.18 (d, 1H, J=13.29 Hz), 3.00 (d, 1H, J=13.29 Hz), 2.90 (t, 2H, J=6.65 Hz), 2.52 (d, 1H, J=15.25 Hz), 2.32 (t, 2H, J=19.55 Hz), 1.29 (s, 3H) MS (ES⁺) m/z mass calcd for $C_{34}H_{31}ClNO_5$ 568.19, found 568.2.

Example 29

2-(4-Cyclohexyl-phenoxy)-2-methyl-3-(4-{2-[5-methyl-2-(3-thiophen-2-yl-phenyl)-oxazol-4-yl]-ethoxy}-phenyl)-propionic acid

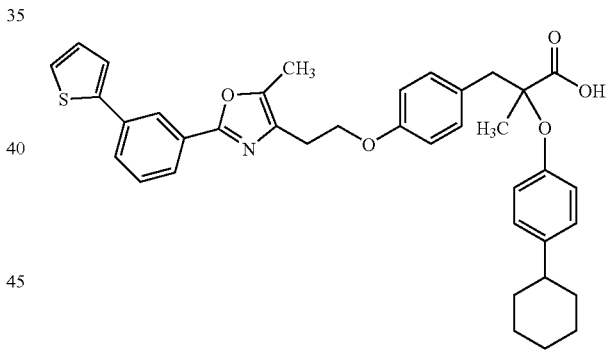

A. 2-(4-Cyclohexylphenoxy)propionic acid ethyl ester

4-Cyclohexylphenol (0.30 mol), $Cs_2CO_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over $Na_2SO_4$ and concentrated in vacuo to produce an oil.

B. 2-(4-Cyclohexylphenoxy)-3-(4-benzyloxyphenyl)-2-methyl-propionic acid ethyl ester A solution of LDA (16.5 mL, 24.7 mmol, 1.5M in cyclohexane) was cooled to −78° C. in a dry ice/acetone bath and then added to a solution 2-(4-cyclohexylphenoxy)propionic acid ethyl ester (24.7 mmol) in anhydrous THF (30 mL) also cooled to −78° C. under an atmosphere of nitrogen. After 5 min, 4-benzyloxybenzaldehyde (4.76 g, 22.4 mmol)

was added in one portion. After stirring for 10 min, the reaction mixture was quenched with saturated solution of aqueous NH$_4$Cl (10 mL) and the mixture allowed to warm to ambient temperature. The biphasic mixture was diluted with ether (100 mL) and partitioned, and the organic layer was washed with brine, dried over MgSO$_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxyphenyl)-2-(4-cyclohexylphenoxy)-3-hydroxy-2-methylpropionic acid ethyl ester which was used without further characterization or purification.

3-(4-Benzyloxyphenyl)-3-hydroxy-2-(4-cyclohexylphenoxy)-2-methylpropionic acid ethyl ester (9.5 mmol) in anhydrous CH$_2$Cl$_2$ (30 mL) was cooled to 0° C. and treated with BF$_3$-Et$_2$O (1.16 mL, 9.5 mmol) and triethylsilane (1.51 mL, 9.5 mmol). The mixture was stirred for 2 h and gradually warmed to ambient temperature. Saturated aqueous Na$_2$CO$_3$ (15 mL) was added and the mixture was stirred vigorously. The solution was partitioned and the organic layer was washed twice with water and brine, dried over Na$_2$SO$_4$, and concentrated in vacuo to produce 3-(4-benzyloxyphenyl)-2-(4-cyclohexylphenoxy)-2-methylpropionic acid ethyl ester as an oil.

C. 2-(4-Cyclohexylphenoxy)-3-(4-hydroxyphenyl)-2-methyl-propionic acid ethyl ester 2-(4-Cyclohexylphenoxy-3-(4-benzyloxyphenyl)-2-methyl-propionic acid ethyl ester (2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to an oil.

D. 2-(4-Cyclohexyl-phenoxy)-2-methyl-3-(4-{2-[5-methyl-2-(3-thiophen-2-yl-phenyl)-oxazol-4-yl]-ethoxy}-phenyl)-propionic acid A mixture of 2-(4-cyclohexylphenoxy)-3-(4-hydroxyphenyl)-2-methyl-propionic acid ethyl ester (0.030 mmol), toluene-4-sulfonic acid 2-[5-methyl-2-(3-thiophen-2-ylphenyl)oxazol-4-yl]ethyl ester (0.030 mmol) (see Ex. 5, Part B) and 325 mesh K$_2$CO$_3$ (0.084 g, 0.60 mmol) in ethanol (2 mL) was heated to reflux for 24 h under N$_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and CH$_2$Cl$_2$ and the organic layer dried by passing it through a Varian Chem Elut 1003 cartridge. The solvent was removed in vacuo to give 2-(4-cyclohexyl-phenoxy)-2-methyl-3-(4-{2-[5-methyl-2-(3-thiophen-2-yl-phenyl)-oxazol-4-yl]-ethoxy}-phenyl)-propionic acid. $^1$H NMR (400 MHz, CDCl$_3$) δ 8.21 (s, 1H), 7.88 (d, 1H, J=7.82 Hz), 7.64 (d, 1H, J=7.82 Hz), 7.43 (d, 1H, J=7.82 Hz), 7.41 (dd, 1H, J=3.52 Hz, 1.17 Hz), 7.31 (dd, 1H, J=3.91 Hz, 1.17 Hz), 7.19 (d, 2H, J=8.60 Hz), 7.10–7.06 (m, 3H), 6.84 (d, 2H, J=7.04 Hz), 6.82 (d, 2H, J=8.21 Hz), 4.23 (t, 2H, J=6.65 Hz), 3.22 (d, 1H, J=14.08 Hz), 3.13 (d, 1H, J=14.08 Hz), 2.99 (t, 2H, J=6.65 Hz), 2.39 (s, 3H), 1.81 (d, 5H, J=8.60 Hz), 1.40 (s, 3H), 1.38–1.32 (m, 5H). MS (ES$^+$) m/z mass calcd C$_{38}$H$_{40}$NO$_5$S 622.26, found 622.3.

Example 30

3-{4-[2-(2-Biphenyl-4-yl-5-methyl-oxazol-4-yl)-ethoxy]-phenyl}-2-(4-cyclohexyl-phenoxy)-2-methyl-propionic acid

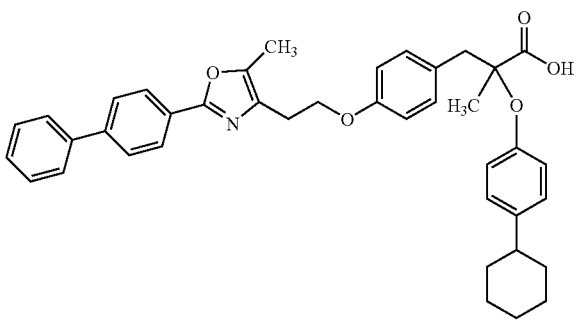

A. 3-{4-[2-(2-Biphenyl-4-yl-5-methyl-oxazol-4-yl)-ethoxy]-phenyl}-2-(4-cyclohexyl-phenoxy)-2-methyl-propionic acid A mixture of 2-(4-cyclohexylphenoxy)-3-(4-hydroxyphenyl)-2-methyl-propionic acid ethyl ester (0.030 mmol) (see Ex. 29, Part C), toluene-4-sulfonic acid 2-(5-methyl-2-biphenyl-4-yl-oxazol-4-yl)ethyl ester (0.030 mmol) (see Ex. 1, Part I) and 325 mesh K$_2$CO$_3$ (0.084 g, 0.60 mmol) in ethanol (2 mL) was heated to reflux for 24 h under N$_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and CH$_2$Cl$_2$ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-(4-cyclohexyl-phenoxy)-2-methyl-propionic acid. $^1$H NMR (400 MHz, CDCl$_3$) δ 8.03 (d, 2H, J=8.60 Hz), 7.66–7.62 (m, 4H), 7.48–7.44 (m, 2H), 7.39–7.36 (m, 1H), 7.19 (d, 3H, J=8.60 Hz), 7.07 (d, 2H, J=8.60 Hz), 6.83 (q, 3H, J=3.52 Hz), 4.13 (t, 2H, J=6.65 Hz), 3.24 (d, 1H, J=13.30 Hz), 3.12 (d, 1H, J=13.30 Hz), 2.99 (t, 2H, J=66.5 Hz), 2.38 (s, 3H), 1.82–1.69 (m, 4H), 1.41 (s, 3H), 1.37–1.22 (m, 6H). MS (ES$^+$) m/z mass calcd for C$_{40}$H$_{42}$NO$_5$ 616.31, found 616.3.

Example 31

3-{4-[2-(2-Biphenyl-3-yl-5-methyl-oxazol-4-yl)-ethoxy]-phenyl}-2-(4-cyclohexyl-phenoxy)-2-methyl-propionic acid

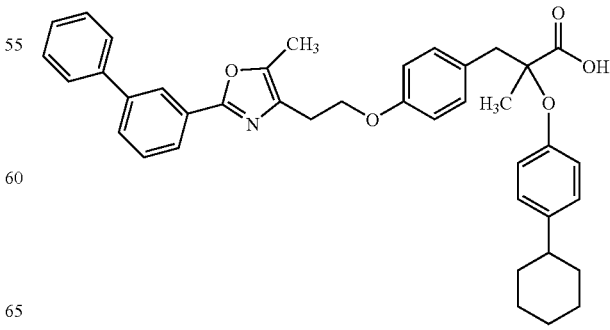

A. 3-{4-[2-(2-Biphenyl-3-yl-5-methyl-oxazol-4-yl)ethoxy]-phenyl}-2-(4-cyclohexyl-phenoxy)-2-methyl-propionic acid A mixture of 2-(4-cyclohexylphenoxy)-3-(4-hydroxyphenyl)-2-methyl-propionic acid ethyl ester (0.030 mmol) (see Ex. 29, Part C), toluene-4-sulfonic acid 2-(2-biphenyl-3-yl-5-methyloxazol-4-yl)ethyl ester (0.030 mmol) (see Ex. 2, Part P) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-{4-[2-(2-biphenyl-3-yl-5-methyl-oxazol-4-yl)-ethoxy]-phenyl}-2-(4-cyclohexyl-phenoxy)-2-methyl-propionic acid. $^1$H NMR (400 MHz, $CDCl_3$) δ 8.21 (s, 1H), 7.96–7.93 (m, 1H), 7.64 (t, 3H, J=8.21 Hz), 7.50–7.43 (m, 3H), 7.37 (d, 1H, J=8.21 Hz), 7.18 (d, 2H, J=8.60 Hz), 7.07 (d, 2H, J=8.60 Hz), 6.83 (dd, 4H, J=8.60 Hz, 5.47 Hz), 4.22 (t, 2H, J=6.65 Hz), 3.26 (d, 1H, J=14.08 Hz), 3.16 (d, 1H, J=14.08 Hz), 2.99 (t, 2H, J=6.65 Hz), 2.39 (s, 3H), 2.17 (s, 1H), 1.81 (d, 4H, J=9.78 Hz), 1.41 (s, 3H), 1.37–1.22 (m, 5H). MS ($ES^+$) m/z mass calcd for $C_{40}H_{42}NO_5$ 616.31, found 616.3.

Example 32

2-(3,4-Dimethyl-phenoxy)-2-methyl-3-(4-{2-[5-methyl-2-(4-thiophen-2-yl-phenyl)-oxazol-4-yl]-ethoxy}-phenyl)-propionic acid

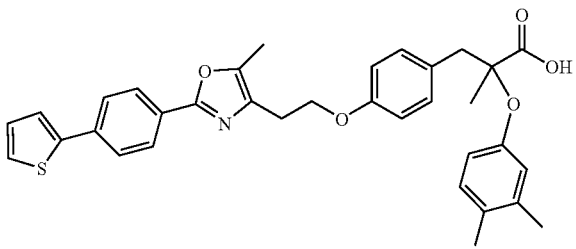

A. 2-(3,4-Dimethylphenoxy)propionic acid ethyl ester 3,4-Dimethylphenol (0.30 mol), $Cs_2CO_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over $Na_2SO_4$ and concentrated in vacuo to produce an oil.

B. 3-(4-Benzyloxyphenyl)-2-(3,4-dimethylphenoxy)-2-methyl-3-(2,2,2-trifluoroacetoxy)propionic acid ethyl ester A solution of LDA (16.5 mL, 24.7 mmol, 1.5M in cyclohexane) was cooled to −78° C. in a dry ice/acetone bath and then added to a solution 2-(3,4-dimethylphenoxy)propionic acid ethyl ester (24.7 mmol) in anhydrous THF (30 mL) also cooled to −78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous $NH_4Cl$ (10 mL) and the mixture allowed to warm to ambient temperature. The biphasic mixture was diluted with ether (100 mL) and partitioned, and the organic layer was washed with brine, dried over $MgSO_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxyphenyl)-2-(3,4-dimethylphenoxy)-3-hydroxy-2-methylpropionic acid ethyl ester which was used without further characterization or purification.

3-(4-Benzyloxyphenyl)-3-hydroxy-2-(3,4-dimethylphenoxy)-2-methylpropionic acid ethyl ester (9.5 mmol) in anhydrous $CH_2Cl_2$ (30 mL) and pyridine (9.5 mmol) was cooled to 0° C. and treated with trifluoroacetic anhydride (19 mmol). The mixture was stirred for 2 h and gradually warmed to ambient temperature. An aqueous solution of 1N HCl (25 mL) was added and the mixture was stirred vigorously. The solution was partitioned and the organic layer was washed twice with water and brine, dried over $Na_2SO_4$, and concentrated in vacuo to produce 3-(4-benzyloxyphenyl)-2-(3,4-dimethylphenoxy)-2-methyl-3-(2,2,2-trifluoroacetoxy) propionic acid ethyl ester as an oil.

C. 2-(3,4-Dimethylphenoxy)-3-(4-hydroxyphenyl)-2-methyl-propionic acid ethyl ester 3-(4-Benzyloxyphenyl)-2-(3,4-dimethylphenoxy)-2-methyl-3-(2,2,2-trifluoroacetoxy)propionic acid ethyl ester (2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to an oil.

D. 2-(3,4-Dimethyl-phenoxy)-2-methyl-3-(4-{2-[5-methyl-2-(4-thiophen-2-yl-phenyl)-oxazol-4-yl]-ethoxy]-phenyl)-propionic acid A mixture of 2-(3,4-dimethylphenoxy)-3-(4-hydroxyphenyl)-2-methyl-propionic acid ethyl ester (0.030 mmol), toluene-4-sulfonic acid 2-(5-methyl-2-(4-thiophen-2-yl-phenyl)-oxazol-4-yl)ethyl ester (0.030 mmol) (see Ex. 3, Part B) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-(3,4-dimethyl-phenoxy)-2-methyl-3-(4-{2-[5-methyl-2-(4-thiophen-2-yl-phenyl)-oxazol-4-yl]-ethoxy}-phenyl)-propionic acid. $^1$H NMR (400 MHz, $CDCl_3$) δ 8.16–8.07 (m, 2H), 7.74–7.71 (m, 2H), 7.44–7.35 (m, 2H), 7.18 (d, 2H, J=8.8 Hz), 7.14–7.11 (m, 1H), 7.00 (d, 1H, J=8.4 Hz), 6.83 (d, 2H, J=8.8 Hz), 6.70 (d, 1H, J=2.6 Hz), 6.64 (dd, 1H, J=8.4, 2.6 Hz), 4.31–4.26 (m, 2H), 3.21 and 3.11 (d of Abq, 2H, J=14.0 Hz), 3.12–3.08 (m, 2H), 2.44 (s, 3H), 2.20 (s, 3H), 2.18 (s, 3H), 1.39 (s, 3H). IR (KBr) 3480, 3000, 1716, 1610, 1512, 1250, 1119 $cm^{-1}$. HRMS ($ES^+$) m/z exact mass calcd for $C_{34}H_{34}NO_5S$ 568.2158, found 568.2168.

Example 33

3-{4-[2-(2-Biphenyl-4-yl-5-methyl-oxazol-4-yl)-ethoxy]-phenyl}-2-(3,4-dimethyl-phenoxy)-2-methyl-propionic acid

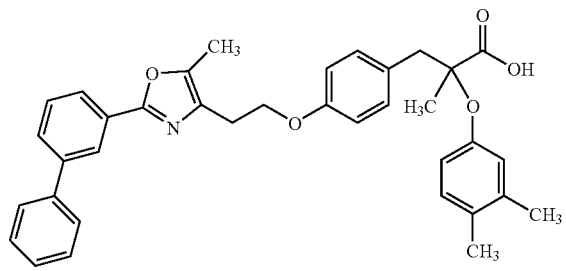

A. 3-{4-[2-(2-Biphenyl-4-yl-5-methyl-oxazol-4-yl)ethoxy]-phenyl}-2-(3,4-dimethyl-phenoxy)-2-methyl-propionic acid A mixture of 2-(3,4-dimethylphenoxy)-3-(4-hydroxyphenyl)-2-methyl-propionic acid ethyl ester (0.030 mmol) (Ex. 32, Part C), toluene-4-sulfonic acid 2-(2-biphenyl-3-yl-5-methyloxazol-4-yl)ethyl ester (0.030 mmol) (see Ex. 2, Part F) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-(3,4-dimethyl-phenoxy)-2-methyl-propionic acid $^1$H NMR (400 MHz, $CDCl_3$) δ 8.23–8.21 (m, 1H), 7.95 (d, 1H, J=7.6 Hz), 7.67–7.62(m, 3H), 7.50–7.42 (m, 3H), 7.38–7.34 (m, 1H), 7.19 (d, 2H, J=8.8 Hz), 6.95 (d, 1H, J=8.2 Hz), 6.82 (d, 2H, J=8.8 Hz), 6.71 (d, 1H, J=2.8 Hz), 6.63 (dd, 1H, J=8.2, 2.8 Hz), 4.20 (t, 2H, J=6.4 Hz), 3.24 and 3.13 (d of Abq, 2H, J=14.0 Hz), 3.01 (t, 2H, J=6.4 Hz), 2.39 (s, 3H), 2.16 (s, 6H, 1.38 (s, 3H). IR (KBr) 3480, 2980, 1717, 1611, 1512, 1248, 1118 cm$^{-1}$. HRMS (ES$^+$) m/z exact mass calcd for $C_{36}H_{36}NO_5$ 562.2593, found 562.2598.

Example 34

3-{4-[2-(2-Biphenyl-4-yl-5-methyl-oxazol-4-yl)-ethoxy]-phenyl}-2-(3,4-dimethyl-phenoxy)-2-methyl-propionic acid

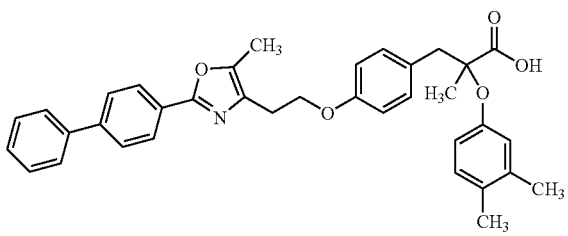

A. 3-{4-[2-(2-Biphenyl-4-yl-5-methyl-oxazol-4-yl)ethoxy]-phenyl}-2-(3,4-dimethyl-phenoxy)-2-methyl-propionic acid A mixture of 2-(3,4-dimethylphenoxy)-3-(4-hydroxyphenyl)-2-methyl-propionic acid ethyl ester (0.030 mmol) (see Ex. 32, Part C), toluene-4-sulfonic acid 2-(5-methyl-2-biphenyl-4-yl-oxazol-4-yl)ethyl ester (0.030 mmol) (see Ex. 1, Part I) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-(3,4-dimethyl-phenoxy)-2-methyl-propionic acid. $^1$H NMR (400 MHz, $CDCl_3$) δ 8.10 (d, 2H, J=8.4 Hz), 7.71 (d, 2H, J=8.4 Hz), 7.65–7.62 (m, 2H), 7.49–7.45 (m, 2H), 7.42–7.30 (m, 1H), 7.19 (d, 2H, J=8.4 Hz), 7.00 (d, 1H, J=8.4 Hz), 6.83 (d, 2H, J=8.4 Hz), 6.70 (d, 1H, J=2.4 Hz), 6.64 (dd, 1H, J=8.4, 2.4 Hz), 4.26 (t, 2H, J=6.0 Hz), 3.22 and 3.11 (d of Abq, 2H, J=14.0 Hz), 3.09 (t, 2H, J=6.0 Hz), 2.44 (s, 3H), 2.19 (s, 3H), 2.18 (s, 3H), 1.39 (s, 3H). IR (KBr) 3480, 2950, 1718, 1611, 1512, 1248, 1177 cm$^{-1}$. HRMS (ES$^+$) m/z exact mass calcd for $C_{36}H_{36}NO_5$ 562.2593, found 562.2595.

Example 35

2-Methyl-3-(4-{2-[5-methyl-2-(4-thiophen-2-yl-phenyl)-oxazol-4-yl]-ethoxy}-phenyl)-2-p-tolyloxy-propionic acid

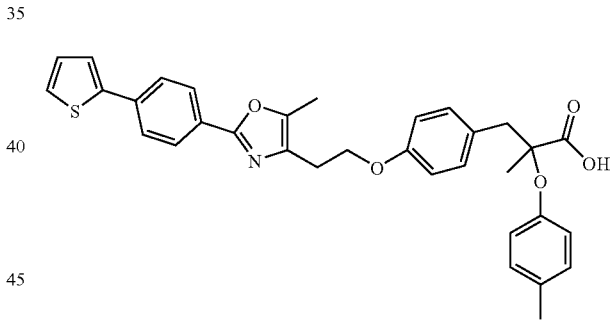

A. 2-(p-Tolyloxy)propionic acid ethyl ester p-Hydroxytoluene (0.30 mol), $Cs_2CO_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over $Na_2SO_4$ and concentrated in vacuo to produce an oil.

B. 2-(p-Tolyloxy)-3-(4-benzyloxyphenyl)-2-methyl-propionic acid ethyl ester

A solution of LDA (16.5 mL, 24.7 mmol, 1.5M in cyclohexane) was cooled to −78° C. in a dry ice/acetone bath and then added to a solution 2-(p-tolylyoxy)propionic acid ethyl ester (24.7 mmol) in anhydrous THF (30 mL) also cooled to −78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous NH₄Cl (10 mL) and the mixture allowed to warm to ambient temperature. The biphasic mixture was diluted with ether (100 mL) and partitioned, and the organic layer was washed with brine, dried over MgSO₄ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxy-phenyl)-2-(p-tolyloxy)-3-hydroxy-2-methylpropionic acid ethyl ester which was used without further characterization or purification.

3-(4-Benzyloxyphenyl)-3-hydroxy-2-(p-tolyloxy)-2-methylpropionic acid ethyl ester (9.5 mmol) in anhydrous CH₂Cl₂ (30 mL) was cooled to 0° C. and treated with BF₃-Et₂O (1.16 mL, 9.5 mmol) and triethylsilane (1.51 mL, 9.5 mmol). The mixture was stirred for 2 h and gradually warmed to ambient temperature. Saturated aqueous Na₂CO₃ (15 mL) was added and the mixture was stirred vigorously. The solution was partitioned and the organic layer was washed twice with water and brine, dried over Na₂SO₄, and concentrated in vacuo to produce 2-(p-tolyloxy)-3-(4-benzyloxyphenyl)-2-methyl-propionic acid ethyl ester as an oil.

C. 2-(p-Tolyloxy)-3-(4-hydroxyphenyl)-2-methyl-propionic acid ethyl ester 2-(p-Tolyloxy)-3-(4-benzyloxyphenyl)-2-methyl-propionic acid ethyl ester (2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to an oil.

D. 2-Methyl-3-(4-{2-[5-methyl-2-(4-thiophen-2-yl-phenyl)-oxazol-4-yl]-ethoxy}-phenyl)-2-p-tolyloxy-propionic acid A mixture 2-(p-tolyloxy)-3-(4-hydroxyphenyl)-2-methyl-propionic acid ethyl ester (0.030 mmol), toluene-4-sulfonic acid 2-(5-methyl-2-(4-thiophen-2-yl-phenyl)-oxazol-4-yl) ethyl ester (0.030 mmol) (see Ex. 3, Part B) and 325 mesh K₂CO₃ (0.084 g, 0.60 mmol) in ethanol (2 mL) was heated to reflux for 24 h under N₂. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and CH₂Cl₂ and the organic layer dried by passing it through a Varian Chem Elut 1003 cartridge. The solvent was removed in vacuo to give 2-methyl-3-(4-{2-[5-methyl-2-(4-thiophen-2-yl-phenyl)-oxazol-4-yl]ethoxy}-phenyl)-2-p-tolyloxy-propionic acid. ¹H NMR (400 MHz, CDCl₃) δ 8.00 (d, 2H, J=8.4 Hz), 7.71 (d, 2H, J=8.4 Hz), 7.42 (dd, 1H, J=3.8, 1.0 Hz), 7.36 (dd, 1H, J=5.0, 1.0 Hz), 7.26–7.25 (m, 1H), 7.18 (d, 2H, J=8.4 Hz), 7.12 (dd, 1H, J=5.0, 3.8 Hz), 7.05 (d, 2H, J=8.4 Hz), 6.81 and 6.81 (d of Abq, 4H, J=8.8 Hz), 4.23 (t, 2H, J=6.2 Hz), 3.23 and 3.12 (d of Abq, 2H, J=14.0 Hz), 3.07 (t, 2H, J=6.2 Hz), 2.43 (s, 3H), 2.28 (s, 3H), 1.39 (s, 3H). IR (KBr) 3450, 1718, 1681, 1509, 1216 cm⁻¹. HRMS (ES⁺) m/z exact mass calcd for C₃₃H₃₂NO₅S 554.2001, found 554.2015.

Example 36

3-{4-[2-(2-Biphenyl-4-yl-5-methyl-oxazol-4-yl)-ethoxy]-phenyl}-2-methyl-2-p-tolyloxy-propionic acid

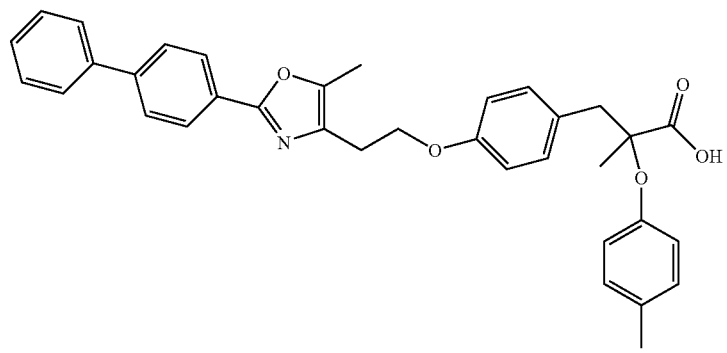

A. 3-{4-[2-(2-Biphenyl-4-yl-5-methyl-oxazol-4-yl)-ethoxy]-phenyl}-2-methyl-2-p-tolyloxy-propionic acid A mixture 2-(p-tolyloxy)-3-(4-hydroxyphenyl)-2-methyl-propionic acid ethyl ester (0.030 mmol) (see Ex. 35, Part C), toluene-4-sulfonic acid 2-(5-methyl-2-biphenyl-4-yl-oxazol-4-yl)ethyl ester (0.030 mmol) (see Ex. 1, Part I) and 325 mesh K₂CO₃ (0.084 g, 0.60 mmol) in ethanol (2 mL) was heated to reflux for 24 h under N₂. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and CH₂Cl₂ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-methyl-2-p-tolyloxy-propionic acid. ¹H NMR (400 MHz, CDCl₃) δ 8.87 (bs, 1H), 8.07 (d, 2H, J=8.6 Hz), 7.72 (d, 2H, J=8.6 Hz), 7.65–7.63 (m, 2H), 7.50–7.38 (m, 3H), 7.19 (d, 2H, J=8.4 Hz), 7.04 (d, 2H, J=8.0 Hz), 6.82 (d, 2H, J=8.4 Hz), 6.80 (d, 2H, J=8.0 Hz), 4.23 (t, 2H, J=6.0 Hz), 3.24 and 3.22 (d of Abq, 2H, J=14.0 Hz), 3.09 (t, 2H, J=6.0 Hz), 2.45 (s, 3H), 2.28 (s, 3H), 1.38 (s, 3H). IR (KBr) 3450, 2924, 1719, 1682, 1509, 1207 cm⁻¹. HRMS (ES⁺) m/z exact mass calcd for C₃₅H₃₄NO₅ 548.2437, found 548.2455.

Example 37

3-{4-[2-(2-Biphenyl-4-yl-5-methyl-oxazol-4-yl)-ethoxy]-phenyl}-2-methyl-2-(4-trifluoromethoxy-phenoxy)-propionic acid

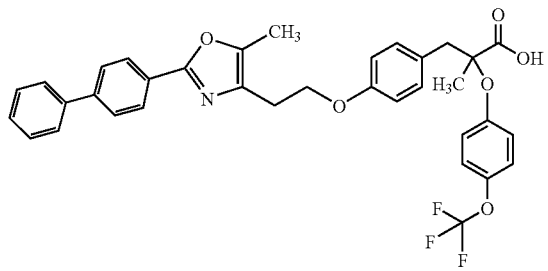

A. 2-(4-Trifluoromethoxyphenoxy)propionic acid ethyl ester

4-Trifluoromethoxyphenol (0.30 mol), Cs$_2$CO$_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over Na$_2$SO$_4$ and concentrated in vacuo to produce an oil.

B. 2-(4-Trifluoromethoxyphenoxy)-3-(4-benzyloxyphenyl)-2-methyl-propionic acid ethyl ester A solution of LDA (16.5 mL, 24.7 mmol, 1.5M in cyclohexane) was cooled to −78° C. in a dry ice/acetone bath and then added to a solution 2-(4-trifluoromethoxyphenoxy) propionic acid ethyl ester (24.7 mmol) in anhydrous THF (30 mL) also cooled to −78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous NH$_4$Cl (10 mL) and the mixture allowed to warm to ambient temperature. The biphasic mixture was diluted with ether (100 mL) and partitioned, and the organic layer was washed with brine, dried over MgSO$_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxy-phenyl)-2-(4-trifluoromethoxyphenoxy)-3-hydroxy-2-methylpropionic acid ethyl ester which was used without further characterization or purification.

3-(4-Benzyloxyphenyl)-3-hydroxy-2-(4-trifluoromethoxyphenoxy)-2-methylpropionic acid ethyl ester (9.5 mmol) in anhydrous CH$_2$Cl$_2$ (30 mL) was cooled to 0° C. and treated with BF$_3$-Et$_2$O (1.16 mL, 9.5 mmol) and triethylsilane (1.51 mL, 9.5 mmol). The mixture was stirred for 2 h and gradually warmed to ambient temperature. Saturated aqueous Na$_2$CO$_3$ (15 mL) was added and the mixture was stirred vigorously. The solution was partitioned and the organic layer was washed twice with water and brine, dried over Na$_2$SO$_4$, and concentrated in vacuo to produce 3-(4-benzyloxyphenyl)-2-(4-trifluoromethoxyphenoxy)-2-methylpropionic acid ethyl ester as an oil.

C. 2-(4-Trifluoromethoxyphenoxy)-3-(4-hydroxyphenyl)-2-methyl-propionic acid ethyl ester 2-(4-Trifluoromethoxyphenoxy)-3-(4-benzyloxyphenyl)-2-methyl-propionic acid ethyl ester (2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to an oil.

D. 3-{4-[2-(2-Biphenyl-4-yl-5-methyl-oxazol-4-yl)-ethoxy]-phenyl}-2-methyl-2-(4-trifluoromethoxy-phenoxy)-propionic acid A mixture of 2-(4-trifluoromethoxyphenoxy)-3-(4-hydroxyphenyl)-2-methyl-propionic acid ethyl (0.030 mmol), toluene-4-sulfonic acid 2-(5-methyl-2-biphenyl-4-yl-oxazol-4-yl)ethyl ester (0.030 mmol) (see Ex. 1, Part I) and 325 mesh K$_2$CO$_3$ (0.084 g, 0.60 mmol) in ethanol (2 mL) was heated to reflux for 24 h under N$_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and CH$_2$Cl$_2$ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-methyl-2-(4-trifluoromethoxy-phenoxy)-propionic acid. $^1$H NMR (400 MHz, CDCl$_3$) δ 8.05 (d, 2H, J=8.4 Hz), 7.68 (d, 2H, J=8.4 Hz), 7.63 (d, 2H, J=8.4 Hz), 7.49–7.43 (m, 2H), 7.41–7.37 (m, 1H), 7.18 (d, 2H, J=8.4 Hz), 7.09 (d, 2H, J=8.4 Hz), 6.90 (d, 2H, J=8.6 Hz), 6.83 (d, 2H, J=8.6 Hz), 4.22 (t, 2H, J=6.4 Hz), 3.25 and 3.14 (d of Abq, 2H, J=14.0 Hz), 3.05 (t, 2H, J=6.4 Hz), 2.42 (s, 3H), 1.43 (s, 3H). IR (KBr) 3600, 3000, 1717, 1612, 1504, 1265 cm$^{-1}$. HRMS (ES$^+$) m/z exact mass calcd for C$_{35}$H$_{31}$NO$_6$F$_3$ 618.2103, found 618.2104.

Example 38

3-{4-[2-(2-Biphenyl-3-yl-5-methyl-oxazol-4-yl)-ethoxy]-phenyl}-2-methyl-2-(4-trifluoromethoxy-phenoxy)-propionic acid

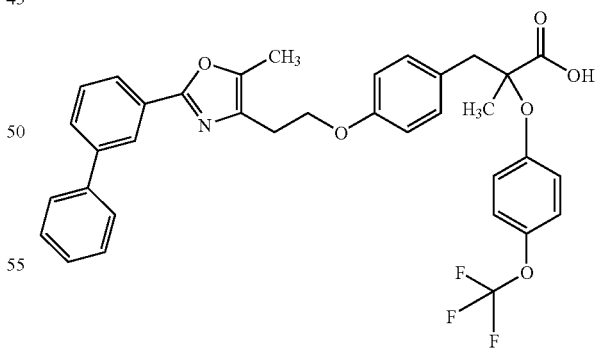

A. 3-{4-[2-(2-Biphenyl-4-yl-5-methyl-oxazol-4-yl)-ethoxy]-phenyl}-2-methyl-2-(4-trifluoromethoxy-phenoxy)-propionic acid A mixture of 2-(4-trifluoromethoxyphenoxy)-3-(4-hydroxyphenyl)-2-methyl-propionic acid ethyl (0.030 mmol) (see Ex. 37, Part C), toluene-4-sulfonic acid 2-(2-biphenyl-3-yl-5-methyloxazol-4-yl)ethyl ester (0.030 mmol) (see Ex.

2, Part F) and 325 mesh K₂CO₃ (0.084 g, 0.60 mmol) in ethanol (2 mL) was heated to reflux for 24 h under N₂. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and CH₂Cl₂ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-methyl-2-(4-trifluoromethoxy-phenoxy)-propionic acid. ¹H NMR (400 MHz, CDCl₃) δ 11.80 (bs, 1H), 8.25 (bs, 1H), 7.98–7.94 (m, 1H), 7.70–7.64 (m, 3H), 7.53–7.43 (m, 3H), 7.39–7.35 (m, 1H), 7.18 (d, 2H, J=8.8 Hz), 7.06 (d, 2H, J=8.8 Hz), 6.88 (d, 2H, J=8.8 Hz), 6.83 (d, 2H, J=8.8 Hz), 4.22 (t, 2H, J=6.6 Hz), 3.24 and 3.14 (d of ABq, 2H, J=14.2 Hz), 3.05 (t, 2H, J=6.6 Hz), 2.42 (s, 3H), 1.42 (s, 3H). IR (KBr) 3600, 3100, 1716, 1612, 1504, 1265 cm⁻¹. HRMS (ES⁺) m/z exact mass calcd for $C_{35}H_{31}NO_6F_3$ 618.2103, found 618.2108.

Example 39

2-Methyl-3-(4-{2-[5-methyl-2-(4-thiophen-2-yl-phenyl)-oxazol-4-yl]-ethoxy}-phenyl)-2-(4-trifluoromethoxy-phenoxy)-propionic acid

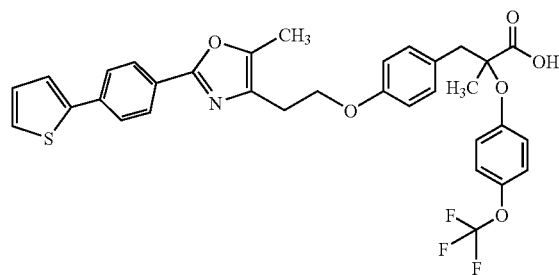

A. 2-Methyl-3-(4-{2-[5-methyl-2-(4-thiophen-2-yl-phenyl)-oxazol-4-yl]-ethoxy}-phenyl)-2-(4-trifluoromethoxy-phenoxy)-propionic acid A mixture of 2-(4-trifluoromethoxyphenoxy)-3-(4-hydroxyphenyl)-2-methyl-propionic acid ethyl (0.030 mmol) (see Ex. 37, Part C), toluene-4-sulfonic acid 2-(5-methyl-2-(4-thiophen-2-yl-phenyl)-oxazol-4-yl)ethyl ester (0.030 mmol) (see Ex. 3, Part B) and 325 mesh K₂CO₃ (0.084 g, 0.60 mmol) in ethanol (2 mL) was heated to reflux for 24 h under N₂. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and CH₂Cl₂ and the organic layer dried by passing it through a Varian Chem Elut 1003 cartridge. The solvent was removed in vacuo to give 2-methyl-3-(4-{2-[5-methyl-2-(4-thiophen-2-yl-phenyl)-oxazol-4-yl]-ethoxy}-phenyl)-2-(4-trifluoromethoxy-phenoxy)-propionic acid. ¹H NMR (400 MHz, CDCl₃) δ 7.96 (d, 2H, J=8.4 Hz), 7.66 (d, 2H, J=8.4 Hz), 7.39 (dd, 1H, J=3.6, 1.2 Hz), 7.33 (dd, 1H, J=5.2, 1.2 Hz), 7.18 (d, 2H, J=8.4 Hz), 7.12–7.07 (m, 3H), 6.92–6.88 (m, 2H), 6.83 (d, 2H, J=8.4 Hz), 4.20 (t, 2H, J=6.4 Hz), 3.25 and 3.14 (d of ABq, 2H, J=14.0 Hz), 3.00 (t, 2H, J=6.4 Hz), 2.40 (s, 3H), 1.43 (s, 3H). IR (KBr) 3600, 3000, 1718, 1504, 1265 cm⁻¹. HRMS (ES⁺) m/z exact mass calcd for $C_{33}H_{29}NO_6F_3S$ 624.1667, found 624.1675.

Example 40

2-{4-[2-(2-Biphenyl-4-yl-5-methyl-oxazol-4-yl)-ethoxy]-benzyl}-2-phenoxy-butyric acid

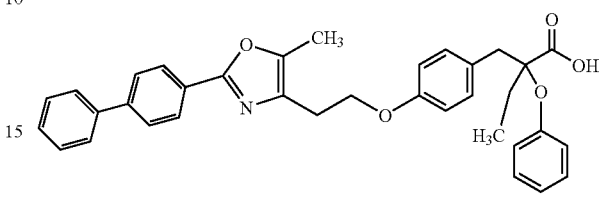

A. 2-Phenoxybutyric acid ethyl ester

Phenol (28.5 g, 0.30 mol), Cs₂CO₃ (197.0 g, 0.61 mol), and ethyl 2-bromobutyrate (0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over Na₂SO₄ and concentrated in vacuo to produce an oil.

B. 2-(4-Benzyloxybenzyl)-2-phenoxybutric acid ethyl ester

A solution of LDA (16.5 mL, 24.7 mmol, 1.5M in cyclohexane) was cooled to –78° C. in a dry ice/acetone bath and then added to a solution of 2-phenoxybutyric acid ethyl ester (24.7 mmol) in anhydrous THF (30 mL) also cooled to –78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous NH₄Cl (10 mL) and the mixture allowed to warm to ambient temperature. The biphasic mixture was diluted with ether (100 mL) and partitioned, and the organic layer was washed with brine, dried over MgSO₄ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 2-[(4-benzyloxyphenyl)hydroxymethyl]-2-phenoxy-butyric acid ethyl ester which was used without further characterization or purification.

2-[(4-Benzyloxyphenyl)-hydroxymethyl]-2-phenoxy-butyric acid ethyl ester (9.5 mmol) in anhydrous CH₂Cl₂ (30 mL) was cooled to 0° C. and treated with BF₃-Et₂O (1.16 mL, 9.5 mmol) and triethylsilane (1.51 mL, 9.5 mmol). The mixture was stirred for 2 h and gradually warmed to ambient temperature. Saturated aqueous Na₂CO₃ (15 mL) was added and the mixture was stirred vigorously. The solution was partitioned and the organic layer was washed twice with water and brine, dried over Na₂SO₄, and concentrated in vacuo to produce 2-(4-benzyloxybenzyl)-2-phenoxybutyric acid ethyl ester as an oil.

C. 2-(4-Hydroxybenzyl)-2-phenoxybutyric acid ethyl ester 2-(4-Benzyloxybenzyl)-2-phenoxybutyric acid ethyl ester (2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to an oil.

D. 2-{4-[2-(2-Biphenyl-4-yl-5-methyl-oxazol-4-yl)-ethoxy]-benzyl}-2-phenoxy-butyric-acid A mixture of 2-(4-hydroxybenzyl)-2-phenoxybutyric acid ethyl ester (0.030 mmol), toluene-4-sulfonic acid 2-(5-methyl-2-biphenyl-4-yl-oxazol-4-yl)ethyl ester (0.030 mmol) (see Ex. 1, Part I) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-{4-[2-(2-Biphenyl-4-yl-5-methyl-oxazol-4-yl)-ethoxy]-benzyl}-2-phenoxy-butyric acid. $^1$H NMR (400 MHz, CDCl$_3$) δ 8.05–8.03 (m, 2H), 7.68–7.61 (m, 4H), 7.48–7.44 (m, 2H), 7.40–7.35 (m, 1H), 7.32–7.25 (m, 2H), 7.09–6.96 (m, 5H), 6.79–6.70 (m, 2H), 4.19 (t, 2H, J=6.4 Hz), 3.29 (s, 2H), 2.99 (t, 2H, J=6.4 Hz), 2.39 (s, 3H), 2.14 (qd, 1H, J=14.8, 7.6 Hz), 2.07 (qd, 1H, J=14.8, 7.6 Hz), 0.91 (t, 3H, J=7.6 Hz).

Example 41

2-{4-[2-(2-Biphenyl-3-yl-5-methyl-oxazol-4-yl)-ethoxy]-benzyl}-2-phenoxy-butyric acid

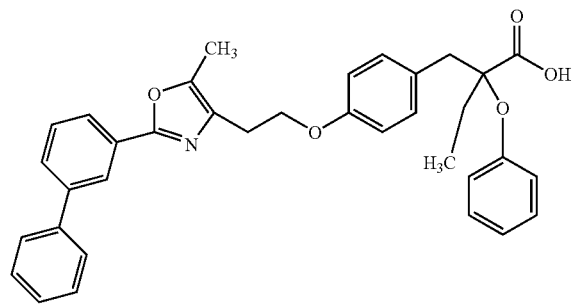

A. 2-{4-[2-(2-Biphenyl-3-yl-5-methyl-oxazol-4-yl)-ethoxy]-benzyl}-2-phenoxy-butyric acid A mixture of 2-(4-hydroxybenzyl)-2-phenoxybutyric acid ethyl ester (0.030 mmol) (see Ex. 40, Part C), toluene-4-sulfonic acid 2-(2-biphenyl-3-yl-5-methyloxazol-4-yl)ethyl ester (0.030 mmol) (see Ex. 2, Part F) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-{4-[2-(2-biphenyl-3-yl-5-methyl-oxazol-4-yl)-ethoxy]-benzyl}-2-phenoxy-butyric acid. $^1$H NMR (400 MHz, CDCl$_3$) δ 8.30–8.20 (m, 1H), 7.96–7.93 (m, 1H), 7.68–7.63 (m, 3H), 7.53–7.43 (m, 3H), 7.39–7.34 (m, 1H), 7.32–7.24 (m, 2H), 7.09–7.05 (m, 1H), 7.02–6.97 (m, 4H), 6.78–6.73 (m, 2H), 4.20 (t, 2H, J=6.4 Hz), 3.29 (s, 2H), 3.01 (t, 2H, J=6.4 Hz), 2.39 (s, 3H), 2.14 (qd, 1H, J=14.8, 7.6 Hz), 2.08 (qd, 1H, J=14.8, 7.6 Hz), 0.91 (t, 3H, J=7.6 Hz.

Example 42

2-(4-{2-[5-Methyl-2-(3-thiophen-2-yl-phenyl)-oxazol-4-yl]-ethoxy}-benzyl)-2-phenoxy-butyric acid

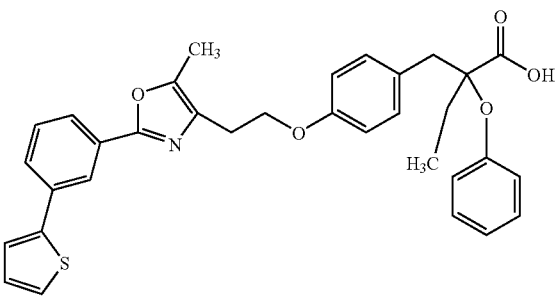

A. 2-(4-{2-[5-Methyl-2-(3-thiophen-2-yl-phenyl)-oxazol-4-yl]-ethoxy}-benzyl)-2-phenoxy-butyric acid A mixture of 2-(4-hydroxybenzyl)-2-phenoxybutyric acid ethyl ester (0.030 mmol) (see Ex. 40, Part C), toluene-4-sulfonic acid 2-[5-methyl-2-(3-thiophen-2-ylphenyl)oxazol-4-yl]ethyl ester (0.030 mmol) (see Ex. 5, Part B) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-(4-{2-[5-methyl-2-(3-thiophen-2-yl-phenyl)-oxazol-4-yl]-ethoxy}-benzyl)-2-phenoxy-butyric acid. $^1$H NMR (400 MHz, CDCl$_3$) δ 8.22–8.21 (m, 1H), 7.89–7.85 (m, 1H), 7.66–7.62 (m, 1H), 7.45–7.40 (m, 2H), 7.32–7.25 (m, 3H), 7.11–6.97 (m, 6H), 6.77 (d, 2H, J=8.4 Hz), 4.20 (t, 2H, J=6.4 Hz), 3.29 (s, 2H), 2.98 (t, 2H, J=6.4 Hz), 2.39 (s, 3H), 2.14 (qd, 1H, J=14.6, 7.6 Hz), 2.07 (qd, 1H, J=14.6, 7.6 Hz), 0.91 (t, 3H, J=7.6 Hz).

Example 43

3-{4-[2-(2-Biphenyl-4-yl-5-methyl-oxazol-4-yl)-ethoxy]-phenyl}-2-methyl-2-(4-trifluoromethyl-phenoxy)-propionic acid

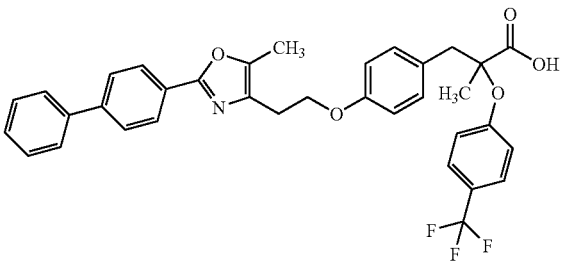

A. 2-(4-Trifluoromethylphenoxy)propionic acid ethyl ester
4-Trifluoromethylphenol (0.30 mol), $Cs_2CO_3$ (197.0 g, 0.61 mol), and ethyl 2-bromopropionate (54.3 g, 0.30 mol)

were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over $Na_2SO_4$ and concentrated in vacuo to produce an oil.

B. 2-(4-Trifluoromethylphenoxy)-3-(4-benzyloxyphenyl)-2-methyl-propionic acid ethyl ester A solution of LDA (16.5 mL, 24.7 mmol, 1.5M in cyclohexane) was cooled to −78° C. in a dry is ice/acetone bath and then added to a solution 2-(4-trifluoromethylphenoxy)propionic acid ethyl ester (24.7 mmol) in anhydrous THF (30 mL) also cooled to −78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous $NH_4Cl$ (10 mL) and the mixture allowed to warm to ambient temperature. The biphasic mixture was diluted with ether (100 mL) and partitioned, and the organic layer was washed with brine, dried over $MgSO_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxy-phenyl)-2-(4-trifluoromethylphenoxy)-3-hydroxy-2-methylpropionic acid ethyl ester which was used without further characterization or purification.

3-(4-Benzyloxyphenyl)-3-hydroxy-2-(4-trifluoromethylphenoxy)-2-methylpropionic acid ethyl ester (9.5 mmol) in anhydrous $CH_2Cl_2$ (30 mL) was cooled to 0° C. and treated with $BF_3$-$Et_2O$ (1.16 mL, 9.5 mmol) and triethylsilane (1.51 mL, 9.5 mmol). The mixture was stirred for 2 h and gradually warmed to ambient temperature. Saturated aqueous $Na_2CO_3$ (15 mL) was added and the mixture was stirred vigorously. The solution was partitioned and the organic layer was washed twice with water and brine, dried over $Na_2SO_4$, and concentrated in vacuo to produce 3-(4-benzyloxyphenyl)-2-(4-trifluoromethylphenoxy)-2-methyl-propionic acid ethyl ester as an oil.

C. 2-(4-Trifluoromethylphenoxy)-3-(4-hydroxyphenyl)-2-methyl-propionic acid ethyl ester 2-(4-Trifluoromethylphenoxy-3-(4-benzyloxyphenyl)-2-methyl-propionic acid ethyl ester (2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to an oil.

D. 3-{4-[2-(2-Biphenyl-4-yl-5-methyl-oxazol-4-yl)ethoxy]-phenyl}-2-methyl-2-(4-trifluoromethyl-phenoxy)-propionic acid A mixture of 2-(4-trifluoromethylphenoxy)-3-(4-hydroxyphenyl)-2-methyl-propionic acid ethyl (0.030 mmol), toluene-4-sulfonic acid 2-(5-methyl-2-biphenyl-4-yl-oxazol-4-yl)ethyl ester (0.030 mmol) (see Ex. 1, Part I) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-methyl-2-(4-trifluoromethyl-phenoxy)-propionic acid. $^1$H NMR (400 MHz, $CDCl_3$) δ 8.01 (d, 2H, J=8.4 Hz), 7.67–7.60 (m, 4H), 7.52–7.44 (m, 4H), 7.42–7.36 (m, 1H), 7.18 (d, 2H, J=8.4 Hz), 6.96 (d, 2H, J=8.8 Hz), 6.83 (d, 2H, J=8.8 Hz), 4.18 (t, 2H, J=6.2 Hz), 3.89 (bs, 1H), 3.27 and 3.19 (d of ABq, 2H, J=13.8 Hz), 3.03 (t, 2H, J=6.2 Hz), 2.41 (s, 3H), 1.50 (s, 3H). IR (KBr) 3420, 2950, 1721, 1613, 1513, 1327, 1248 cm$^{-1}$. HRMS (ES$^+$) m/z exact mass calcd for $C_{35}H_{31}NO_5F_3$ 602.2154, found 602.2151.

Example 44

2-Methyl-3-(4-{2-[5-methyl-2-(4-thiophen-2-yl-phenyl)-oxazol-4-yl]-ethoxy}-phenyl}-2-(4-trifluoromethyl-phenoxy)-propionic acid

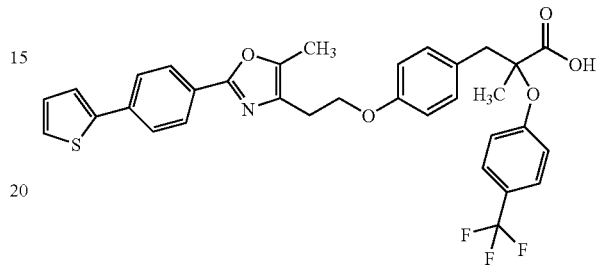

A. 2-Methyl-3-(4-{2-[5-methyl-2-(4-thiophen-2-yl-phenyl)-oxazol-4-yl]-ethoxy}-phenyl)-2-(4-trifluoromethyl-phenoxy)-propionic acid A mixture of 2-(4-trifluoromethylphenoxy)-3-(4-hydroxyphenyl)-2-methyl-propionic acid ethyl (0.030 mmol) (see Ex. 43, Part C), toluene-4-sulfonic acid 2-(5-methyl-2-(4-thiophen-2-yl-phenyl)-oxazol-4-yl)ethyl ester (0.030 mmol) (see Ex. 3, Part B) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-methyl-3-(4-{2-[5-methyl-2-(4-thiophen-2-yl-phenyl)-oxazol-4-yl]ethoxy}-phenyl)-2-(4-trifluoromethyl-phenoxy)-propionic acid. $^1$H NMR (400 MHz, $CDCl_3$) δ 8.23 (s, 1H), 7.96–7.92 (m, 1H), 7.68–7.61 (m, 3H), 7.51–7.43 (m, 4H), 7.19–7.15 (m, 2H), 6.93 (d, 2H, J=8.4 Hz), 6.82 (d, 2H, J=8.4 Hz), 4.20 (t, 2H, J=6.4 Hz), 3.26 and 3.18 (d of ABq, 2H, J=14.0 Hz), 3.05 (t, 2H, J=6.4 Hz), 2.42 (s, 3H), 1.49 (s, 3H).

Example 45

3-{4-[2-(2-Biphenyl-4-yl-5-methyl-oxazol-4-yl)-ethoxy]-phenyl}-2-(3,4-difluoro-phenoxy)-2-methyl-propionic acid

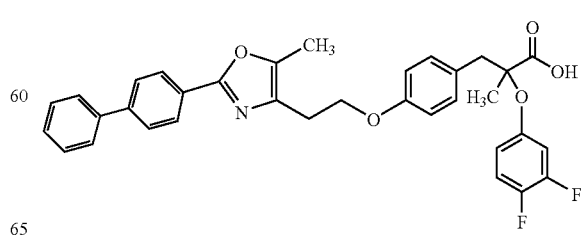

A. 2-(3,4-Difluorophenoxy)propionic acid ethyl ester 3,4-Difluorophenol (0.30 mol), Cs$_2$CO$_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over Na$_2$SO$_4$ and concentrated in vacuo to produce an oil.

B. 2-(3,4-Difluorophenoxy)-3-(4-benzyloxyphenyl)-2-methyl-propionic acid ethyl ester A solution of LDA (16.5 mL, 24.7 mmol, 1.5M in cyclohexane) was cooled to −78° C. in a dry ice/acetone bath and then added to a solution 2-(3,4-difluorophenoxy)propionic acid ethyl ester (24.7 mmol) in anhydrous THF (30 mL) also cooled to −78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous NH$_4$Cl (10 mL) and the mixture allowed to warm to ambient temperature. The biphasic mixture was diluted with ether (100 mL) and partitioned, and the organic layer was washed with brine, dried over MgSO$_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxyphenyl)-2-(3,4-difluoro-phenoxy)-3-hydroxy-2-methylpropionic acid ethyl ester which was used without further characterization or purification.

3-(4-Benzyloxyphenyl)-3-hydroxy-2-(3,4-difluoro-phenoxy)-2-methylpropionic acid ethyl ester (9.5 mmol) in anhydrous CH$_2$Cl$_2$ (30 mL) was cooled to 0° C. and treated with BF$_3$-Et$_2$O (1.16 mL, 9.5 mmol) and triethylsilane (1.51 mL, 9.5 mmol). The mixture was stirred for 2 h and gradually warmed to ambient temperature. Saturated aqueous Na$_2$CO$_3$ (15 mL) was added and the mixture was stared vigorously. The solution was partitioned and the organic layer was washed twice with water and brine, dried over Na$_2$SO$_4$, and concentrated in vacuo to produce 3-(4-benzyloxyphenyl)-2-(3,4-difluorophenoxy)-2-methylpropionic acid ethyl ester as an oil.

C. 2-(3,4-Difluorophenoxy)-3-(4-hydroxyphenyl)-2-methyl-propionic acid ethyl ester 2-(3,4-Difluorophenoxy)-3-(4-benzyloxyphenyl)-2-methyl-propionic acid ethyl ester (2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to an oil.

D. 3-{4-[2-(2-Biphenyl-4-yl-5-methyl-oxazol-4-yl)-ethoxy]-phenyl}-2-(3,4-difluoro-phenoxy)-2-methyl-propionic acid A mixture of 2-(3,4-difluoro-phenoxy)-3-(4-hydroxyphenyl)-2-methyl-propionic acid ethyl ester (0.030 mmol), toluene-4-sulfonic acid 2-(5-methyl-2-biphenyl-4-yl-oxazol-4-yl)ethyl ester (0.030 mmol) (see Ex. 1, Part I) and 325 mesh K$_2$CO$_3$ (0.084 g, 0.60 mmol) in ethanol (2 mL) was heated to reflux for 24 h under N$_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and CH$_2$Cl$_2$ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-(3,4-difluoro-phenoxy)-2-methyl-propionic acid. $^1$H NMR (400 MHz, CDCl$_3$) δ 8.05 (d, 2H, J=8.4 Hz), 7.36 (d, 2H, J=8.4 Hz), 7.63 (dd, 2H, J=7.6, 1.2 Hz), 7.49–7.45 (m,2H), 7.41–7.37 (m, 1H), 7.18 (d, 2H, J=8.8 Hz), 7.00 (q, 1H, J=9.5 Hz), 6.84 (d, 2H, J=8.8 Hz), 6.76 (ddd, 1H, J=11.2, 6.4, 2.8 Hz), 6.64–6.59 (m, 1H), 4.22 (t, 2H, J=6.2 Hz), 3.23 and 3.11 (d of ABq, 2H, J=14.0 Hz), 3.07 (t, 2H, J=6.2 Hz), 2.44 (s, 3H), 1.39 (s, 3H).

Example 46

3-{4-[2-(2-Biphenyl-3-yl-5-methyl-oxazol-4-yl)-ethoxy]-phenyl}-2-(3,4-difluoro-phenoxy)-2-methyl-propionic acid

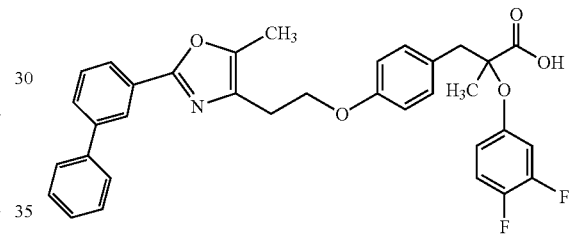

A. 3-{4-[2-(2-Biphenyl-3-yl-5-methyl-oxazol-4-yl)-ethoxy]-phenyl}-2-(3,4-difluoro-phenoxy)-2-methyl-propionic acid A mixture of 2-(3,4-difluorophenoxy)-3-(4-hydroxyphenyl)-2-methyl-propionic acid ethyl ester (0.030 mmol) (see Ex. 45, Part C), toluene-4-sulfonic acid 2-(2-biphenyl-3-yl-5-methyloxazol-4-yl)ethyl ester (0.030 mmol) (see Ex. 2, Part F) and 325 mesh K$_2$CO$_3$ (0.084 g, 0.60 mmol) in ethanol (2 mL) was heated to reflux for 24 h under N$_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and CH$_2$Cl$_2$ and the organic layer dried by passing it through a Varian Chem Elut 1003 cartridge. The solvent was removed in vacuo to give 3-{4-[2-(2-biphenyl-3-yl-5-methyl-oxazol-4-yl)-ethoxy]-phenyl}-2-(3,4-difluoro-phenoxy)-2-methyl-propionic acid. $^1$H NMR (400 MHz, CDCl$_3$) δ 8.24 (s, 1H), 8.23 (bs, 1H), 7.94 (d, 1H, J=8.0 Hz), 7.71 (d, 1H, J=8.0 Hz), 7.65 (d, 2H, J=7.6 Hz), 7.53 (t, 1H, J=7.6 Hz), 7.48–7.43 (m, 2H), 7.40–7.35 (m, 1H), 7.17 (d, 2H, J=8.4 Hz), 6.97 (q, 1H, J=9.6 Hz), 6.83 (d, 2H, J=8.4 Hz), 6.72 (ddd, 1H, J=12.0, 7.2, 3.2 Hz), 6.62–6.58 (m, 1H), 4.22 (t, 2H, J=6.4 Hz), 3.23 and 3.10 (d of ABq, 2H, J=14.0 Hz), 3.08 (t, 2H, J=6.4 Hz), 2.44 (s, 3H), 1.37 (s, 3H).

Example 47

2-(3,4-Difluoro-phenoxy)-2-methyl-3-(4-{2-[5-methyl-2-(4-thiophen-2-yl-phenyl)-oxazol-4-yl]-ethoxy}-phenyl)-propionic acid

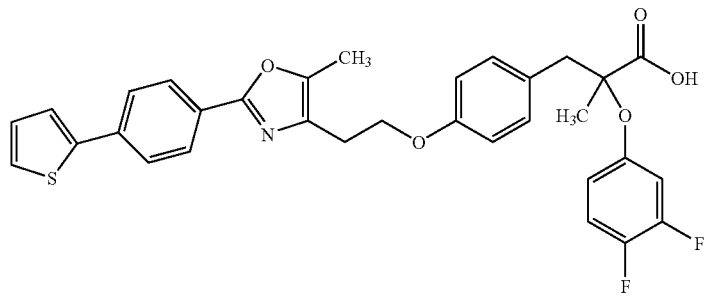

A. 2-(3,4-Difluoro-phenoxy)-2-methyl-3-(4-{2-[5-methyl-2-(4-thiophen-2-yl-phenyl)-oxazol-4-yl]-ethoxy}-phenyl)-propionic acid A mixture of 2-(3,4-difluoro-phenoxy)-3-(4-hydroxyphenyl)-2-methyl-propionic acid ethyl ester (0.030 mmol) (see Ex. 45, Part C), toluene-4-sulfonic acid 2-(5-methyl-2-(4-thiophen-2-yl-phenyl)-oxazol-4-yl)-ethyl ester (0.030 mmol) (see Ex. 3, Part B) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-(3,4-difluoro-phenoxy)-2-methyl-3-(4-{2-[5-methyl-2-(4-thiophen-2-yl-phenyl)-oxazol-4-yl]-ethoxy}-phenyl)-propionic acid. $^1$H NMR (400 MHz, $CDCl_3$) δ 7.99 (d, 2H, J=8.8 Hz), 7.98 (bs, 1H), 7.67 (d, 2H, J=8.8 Hz), 7.42 (dd, 1H, J=4.0, 1.0 Hz), 7.36 (d, 1H, J=4.8 Hz), 7.17 (d, 2H, J=8.8 Hz), 7.12 (dd, 1H, J=4.8, 4.0 Hz), 7.00 (q, 1H, J=9.2 Hz), 6.83 (d, 2H, J=8.8 Hz), 6.76 (ddd, 1H, J=11.6, 6.8, 3.2 Hz), 6.63–6.59 (m, 1H), 4.21 (t, 2H, J=6.6 Hz), 3.23 and 3.10 (d of ABq, 2H, J=14.2 Hz), 3.07 (t, 2H, J=6.6 Hz), 2.43 (s, 3H), 1.38 (s, 3H).

Example 48

3-{4-[2-(2-Biphenyl-3-yl-5-methyl-oxazol-4-yl)-ethoxy]-phenyl}-2-methyl-2-m-tolyloxy-propionic acid

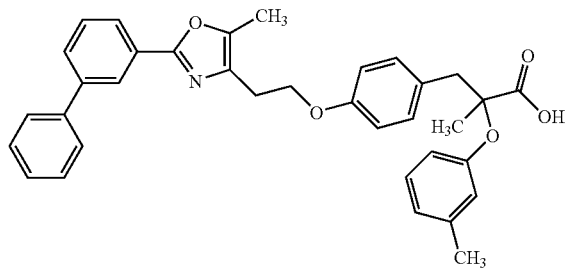

A. 2-(m-Tolyloxy)propionic acid ethyl ester m-Hydroxytoluene (0.30 mol), $Cs_2CO_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over $Na_2SO_4$ and concentrated in vacuo to produce an oil.

B. 3-(4-Benzyloxyphenyl)-2-methyl-2-m-tolyloxy-3-(2,2,2-trifluoroacetoxy)propionic acid ethyl ester A solution of LDA (16.5 mL, 24.7 mmol, 1.5M in cyclohexane) was cooled to –78° C. in a dry ice/acetone bath and then added to a solution 2-(m-tolylyoxy)propionic acid ethyl ester (24.7 mmol) in anhydrous THF (30 mL) also cooled to –78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous $NH_4Cl$ (10 mL) and the mixture allowed to warm to ambient temperature. The biphasic mixture was diluted with ether (100 mL) and partitioned, and the organic layer was washed with brine, dried over $MgSO_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxy-phenyl)-2-(m-tolyloxy)-3-hydroxy-2-methylpropionic acid ethyl ester which was used without further characterization or purification.

3-(4-Benzyloxyphenyl)-3-hydroxy-2-(m-tolyloxy)-2-methylpropionic acid ethyl ester (13.4 mmol) in anhydrous $CH_2Cl_2$ (100 mL) and pyridine (134 mmol) was cooled to 0° C. and treated with trifluoroacetic anhydride (26.9 mmol). The mixture was stirred for 2 h and gradually warmed to ambient temperature. An aqueous solution of 1N HCl (160 mL) was added and the mixture was stirred vigorously. The solution was partitioned and the organic layer was washed twice with water and brine, dried over $Na_2SO_4$, and concentrated in vacuo to produce 3-(4-benzyloxyphenyl)-2-methyl-2-m-tolyloxy-3-(2,2,2-trifluoroacetoxy)propionic acid ethyl ester as an oil.-

C. 2-(m-Tolyloxy)-3-(4-hydroxyphenyl)-2-methyl-propionic acid ethyl ester 3-(4-Benzyloxyphenyl)-2-methyl-2-m-tolyloxy-3-(2,2,2-trifluoroacetoxy)propionic acid ethyl ester (2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to an oil.

D. 3-{4-[2-(2-Biphenyl-3-yl-5-methyl-oxazol-4-yl)-ethoxy]-phenyl}-2-methyl-2-m-tolyloxy-propionic acid A mixture of 2-(m-tolyloxy)-3-(4-hydroxyphenyl)-2-methyl-propionic acid ethyl ester (0.095 g, 0.030 mmol), toluene-4-sulfonic acid 2-(2-biphenyl-3-yl-5-methyloxazol-4-yl)ethyl ester (0.030 mmol) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-(4-[2-(2-biphenyl-3-yl-5-methyl-oxazol-4-yl)-ethoxy]-phenyl}-2-methyl-2-m-tolyloxy-propionic acid. $^1$H NMR (400 MHz, $CDCl_3$) δ 8.18–8.17 (m, 1H), 7.92 (d, 1H, J=7.04 Hz), 7.61–7.57 (m, 3H), 7.45–7.36 (m, 3H), 7.31–7.28 (m, 1H), 7.11 (d, 2H, J=8.60 Hz), 7.05 (t, 1H, J=7.82 Hz), 6.82–6.75 (m, 3H), 6.65–6.61 (m, 2H), 4.17 (t, 2H, J=6.65 Hz), 3.17 (d, 1H, J=13.69 Hz), 3.06 (d, 1H, J=13.69 Hz), 2.96 (t, 2H, J=6.65 Hz) 2.33 (s, 3H), 2.21 (s, 3H), 1.35 (s, 3H); HRMS (ES$^+$) m/z exact mass calcd for $C_{35}H_{34}NO_5$ 548.2437, found 548.2415.

Example 49

3-{4-[2-(2-Biphenyl-4-yl-5-methyl-oxazol-4-yl)-ethoxy]-phenyl}-2-methyl-2-m-tolyloxy-propionic acid

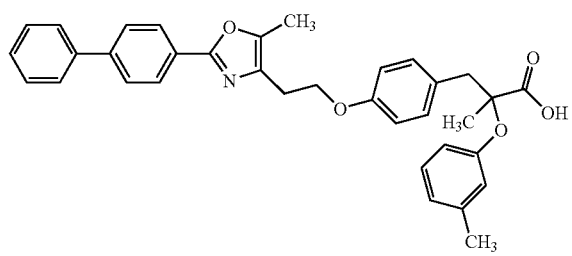

A. 3-{4-[2-(2-Biphenyl-4-yl-5-methyl-oxazol-4-yl)-ethoxy]-phenyl}-2-methyl-2-m-tolyloxy-propionic acid A mixture of 2-(m-tolyloxy)-3-(4-hydroxyphenyl)-2-methyl-propionic acid ethyl ester (0.095 g, 0.030 mmol) (see Ex. 48, Part C), toluene-4-sulfonic acid 2-(5-methyl-2-biphenyl-4-yl-oxazol-4-yl)ethyl ester (0.030 mmol) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-methyl-2-m-tolyloxy-propionic acid. $^1$H NMR (400 MHz, $CDCl_3$) δ 8.06 (d, 2H, J=8.21 Hz), 7.70 (d, 2H, J=8.60 Hz), 7.64–7.62 (m, 2H), 7.48–7.45 (m, 2H), 7.41–7.37 (m, 1H), 7.18 (d, 2H, J=8.60 Hz), 7.12 (t, 1H, J=7.82 Hz), 6.86–6.81 (m, 3H), 6.72–6.68 (m, 2H), 4.22 (t, 2H, J=5.86 Hz), 3.24 (d, 1H, J=14.08 Hz), 3.13 (d, 1H, J=14.08 Hz), 3.08 (t, 2H, J=5.86 Hz) 2.44 (s, 3H), 2.28 (s, 3H), 1.42 (s, 3H); HRMS (ES$^+$) m/z exact mass calcd for $C_{35}H_{34}NO_5$ 548.2437, found 548.2459.

Example 50

2-Methyl-3-(4-{2-[5-methyl-2-(4-thiophen-2-yl-phenyl)-oxazol-4-yl]-ethoxy}-phenyl)-2-m-tolyloxy-propionic acid

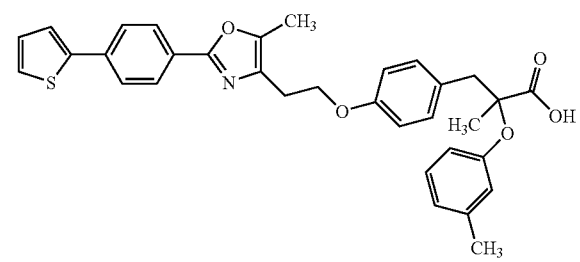

A. 2-Methyl-3-(4-{2-[5-methyl-2-(4-thiophen-2-yl-phenyl)-oxazol-4-yl]-ethoxy}-phenyl)-2-m-tolyloxy-propionic acid A mixture of 2-(m-tolyloxy)-3-(4-hydroxyphenyl)-2-methyl-propionic acid ethyl ester (0.095 g, 0.030 mmol) (see Ex. 48, Part C), toluene-4-sulfonic acid 2-(5-methyl-2-(4-thiophen-2-yl-phenyl)-oxazol-4-yl)ethyl ester (0.030 mmol) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-methyl-3-(4-{2-[5-methyl-2-(4-thiophen-2-yl-phenyl)-oxazol-4-yl]-ethoxy}-phenyl)-2-m-tolyloxy-propionic acid. $^1$H NMR (400 MHz, $CDCl_3$) δ 7.97 (d, 2H, J=8.60 Hz), 7.68 (d, 2H, J=8.60 Hz), 7.40 (d, 1H, J=3.52 Hz), 7.34 (d, 1H, J=4.69 Hz), 7.18 (d, 2H, J=8.21 Hz), 7.15–7.09 (m, 2H), 6.87–6.82 (m, 3H), 6.72–6.69 (m, 2H), 4.22 (t, 2H, J=6.26 Hz), 3.23 (d, 1H, J=14.08 Hz), 3.13 (d, 1H, J=14.08 Hz), 3.03 (t, 2H, J=6.26 Hz) 2.41 (s, 3H), 2.29 (s, 3H), 1.42 (s, 3H); HRMS (ES$^+$) m/z exact mass calcd for $C_{33}H_{32}NO_5S$ 554.2001, found 554.2022.

Example 51

3-{4-[2-(2-Biphenyl-3-yl-5-methyl-oxazol-4-yl)-ethoxy]-phenyl}-2-(4-fluoro-phenoxy)-2-methyl-propionic acid

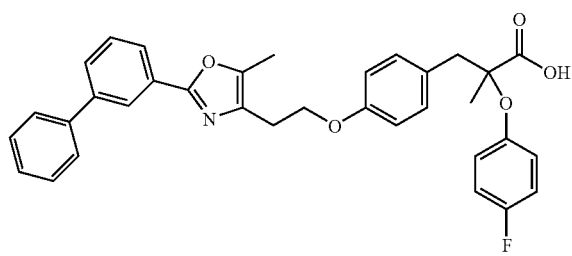

A. 2-(4-Fluorophenoxy)propionic acid ethyl ester

4-Fluorophenol (0.30 mol), $Cs_2CO_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over $Na_2SO_4$ and concentrated in vacuo to produce an oil.

B. 3-(4-Benzyloxyphenyl)-2-(4-fluoro-phenoxy)-2-methyl-3-(2,2,2-trifluoroacetoxy)propionic acid ethyl ester A solution of LDA (16.5 mL, 24.7 mmol, 1.5M in cyclohexane) was cooled to –78° C. in a dry ice/acetone bath and then added to a solution 2-(4-fluoro-phenoxy)propionic acid ethyl ester (24.7 mmol) in anhydrous THF (30 mL) also cooled to –78° C. under an atmosphere of nitrogen. After 5 min, 4-benzyloxybenzaldehyde (4.76 g, 22.4 mmol) was added in one portion. After stirring for 10 min. the reaction mixture was quenched with saturated solution of aqueous $NH_4Cl$ (10 mL) and the mixture allowed to warm to ambient temperature. The biphasic mixture was diluted with ether (100 mL) and partitioned, and the organic layer was washed with brine, dried over $MgSO_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxy-phenyl)-2-(4-fluorophenoxy)-3-hydroxy-2-methylpropionic acid ethyl ester which was used without further characterization or purification.

3-(4-Benzyloxyphenyl)-3-hydroxy-2-(4-fluorophenoxy)-2-methylpropionic acid ethyl ester (13.4 mmol) in anhydrous $CH_2Cl_2$ (100 mL) and pyridine (134 mmol) was cooled to 0° C. and treated with trifluoroacetic anhydride (26.9 mmol). The mixture was stirred for 2 h and gradually warmed to ambient temperature. An aqueous solution of 1N HCl (150 mL) was added and the mixture was stirred vigorously. The solution was partitioned and the organic layer was washed twice with water and brine, dried over $Na_2SO_4$, and concentrated in vacuo to produce 3-(4-benzyloxyphenyl)-2-(4-fluorophenoxy)-2-methyl-3-(2,2,2-trifluoroacetoxy)propionic acid ethyl ester as an oil.

C. 2-(4-Fluorophenoxy)-3-(4-hydroxyphenyl)-2-methyl-propionic acid ethyl ester 3-(4-Benzyloxyphenyl)-2-(4-fluoro-phenoxy)-2-methyl-3-(2,2,2-trifluoroacetoxy)propionic acid ethyl ester (2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to an oil.

D. 3-{4-[2-(2-Biphenyl-3-yl-5-methyl-oxazol-4-yl)-ethoxy]-phenyl}-2-(4-fluoro-phenoxy)-2-methyl-propionic acid A mixture of 2-(4-fluorophenoxy)-3-(4-hydroxyphenyl)-2-methyl-propionic acid ethyl ester (0.030 mmol), toluene-4-sulfonic acid 2-(2-biphenyl-3-yl-5-methyloxazol-4-yl) ethyl ester (0.030 mmol) (see Ex. 2, Part F) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to 3-{4-[2-(2-biphenyl-3-yl-5-methyl-oxazol-4-yl)-ethoxy]-phenyl}-2-(4-fluoro-phenoxy)-2-methyl-propionic acid $^1$H NMR (400 MHz, $CDCl_3$) δ 8.21–8.20 (m, 1H), 7.94–7.92 (m, 1H), 7.65–7.62 (m, 2H), 7.50–7.34 (m, 4H), 7.17 (d, 2H, J=8.60 Hz), 6.93–6.77 (m, 7H), 4.21 (t, 2H, J=6.65 Hz), 3.20 (d, 1H, J=14.00 Hz), 3.13 (d, 1H, J=14.00 Hz), 3.01 (t, 2H, J=6.65 Hz) 2.40 (s, 3H), 1.37 (s, 3H); HRMS (ES$^+$) m/z exact mass calcd for $C_{34}H_{31}NO_5F$ 552.2186, found 552.2175.

Example 52

3-{4-[2-(2-Biphenyl-4-yl-5-methyl-oxazol-4-yl)-ethoxy]-phenyl}-2-(4-fluoro-phenoxy)-2-methyl-propionic acid

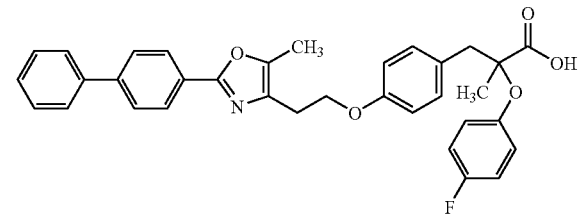

A. 3-{4-[2-(2-Biphenyl-4-yl-5-methyl-oxazol-4-yl)-ethoxy]-phenyl}-2-(4-fluoro-phenoxy)-2-methyl-propionic acid A mixture of 2-(4-fluoro-phenoxy)-3-(4-hydroxyphenyl)-2-methyl-propionic acid ethyl ester (0.030 mmol) (see Ex. 51, Part C), toluene-4-sulfonic acid 2-(5-methyl-2-biphenyl-4-yl-oxazol-4-yl)ethyl ester (0.030 mmol) (see Ex. 1, Part I) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to 3-{4-[2-(2-biphenyl-4-yl-5-methyl-oxazol-4-yl)-ethoxy]-phenyl}-2-(4-fluoro-phenoxy)-2-methyl-propionic acid $^1$H NMR (400 MHz, $CDCl_3$) δ 8.04 (d, 2H, J=6.65 Hz), 7.68 (d, 2H, J=6.65 Hz), 7.64 (d, 2H, J=7.04 Hz), 7.48–7.38 (m, 3H, 7.19 (d, 2H, J=8.99 Hz), 6.94–6.82 (m, 6H), 4.22 (t, 2H, J=6.65 Hz), 3.23 (d, 1H, J=14.08 Hz), 3.12 (d, 1H, J=14.08 Hz), 3.05 (t, 2H, J=6.65 Hz) 2.42 (s, 3H), 1.37 (s, 3H); HRMS (ES$^+$) m/z exact mass calcd for $C_{34}H_{31}NO_5F$ 552.2186, found 552.2202

Example 53

2-(4-Fluoro-phenoxy)-2-methyl-3-(4-{2-[5-methyl-2-(4-thiophen-2-yl-phenyl)-oxazol-4-yl]-ethoxy}-phenyl)-propionic acid

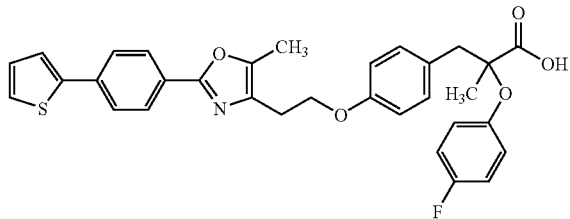

A. 2-(4-Fluoro-phenoxy)-2-methyl-3-(4-{2-[5-methyl-2-(4-thiophen-2-yl-phenyl)-oxazol-4-yl]-ethoxy}-phenyl)-propionic acid A mixture of 2-(4-fluorophenoxy)-3-(4-hydroxyphenyl)-2-methyl-propionic acid ethyl ester (0.030 mmol) (see Ex. 51, Part C), toluene-4-sulfonic acid 2-(5-methyl-2-(4-thiophen-2-yl-phenyl-oxazol-4-yl)ethyl ester (0.030 mmol) (see Ex. 3, Part B) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to 2-(4-fluoro-phenoxy)-2-methyl-3-(4-{2-[5-methyl-2-(4-thiophen-2-yl-phenyl)-oxazol-4-yl]-ethoxy}-phenyl)-propionic acid $^1$H NMR (400 MHz, CDCl$_3$) δ 7.97 (d, 2H, J=8.60 Hz), 7.67 (d, 2H, J=8.60 Hz), 7.40 (dd, 1H, J=5.52 Hz, J=1.17 Hz), 7.33 (dd, 1H, J=5.08 Hz, J=1.17 Hz), 7.18 (d, 2H, J=8.99 Hz), 7.12–7.09 (m, 1H), 7.11 (dd, 1H, J=5.08 Hz, J=3.52 Hz), 6.95–6.82 (m, 5H), 4.21 (t, 2H, J=6.26 Hz), 3.22 (d, 1H, J=14.08 Hz), 3.13 (d, 1H, J=14.08 Hz), 3.03 (t, 2H, J=6.26 Hz) 2.41 (s, 3H), 1.37 (s, 3H); HRMS (ES$^+$) m/z exact mass calcd for $C_{32}H_{29}NO_5FS$ 558.1750, found 558.1769

Example 54

2-Methyl-3-(4-{2-[5-methyl-2-(4-thiophen-2-yl-phenyl)-oxazol-4-yl]-ethoxy}-phenyl)-2-(3-trifluoromethyl-phenoxy)-propionic acid

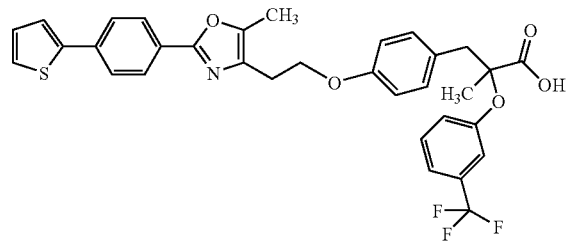

A. 2-(3-Trifluoromethylphenoxy)propionic acid ethyl ester

3-Trifluoromethylphenol (0.30 mol), $Cs_2CO_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over $Na_2SO_4$ and concentrated in vacuo to produce an oil.

B. 3-(4-Benzyloxyphenyl)-2-methyl-3-(2,2,2-trifluoroacetoxy)-2-(3-trifluoromethylphenoxy)-propionic acid ethyl ester A solution of LDA (16.5 mL, 24.7 mmol, 1.5M in cyclohexane) was cooled to −78° C. in a dry ice/acetone bath and then added to a solution 2-(3-trifluoromethylphenoxy) propionic acid ethyl ester (24.7 mmol) in anhydrous THF (30 mL) also cooled to −78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous NH$_4$Cl (10 mL) and the mixture allowed to warm to ambient temperature. The biphasic mixture was diluted with ether (100 mL) and partitioned, and the organic layer was washed with brine, dried over MgSO$_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxy-phenyl)-2-(3-trifluoromethylphenoxy)-3-hydroxy-2-methylpropionic acid ethyl ester which was used without further characterization or purification.

3-(4-Benzyloxyphenyl)-3-hydroxy-2-(3-trifluoromethylphenoxy)-2-methylpropionic acid ethyl ester (13.4 mmol) in anhydrous CH$_2$Cl$_2$ (100 mL) and pyridine (134 mmol) was cooled to 0° C. and treated with trifluoroacetic anhydride (26.9 mmole). The mixture was stirred for 2 h and gradually warmed to ambient temperature. An aqueous solution of 1N HCl (150 mL) was added and the mixture was stirred vigorously. The solution was partitioned and the organic layer was washed twice with water and brine, dried over Na$_2$SO$_4$, and concentrated in vacuo to produce 3-(4-benzyloxyphenyl)-2-methyl-3-(2,2,2-trifluoroacetoxy)-2-(3-trifluoromethylphenoxy)-propionic acid ethyl ester as an oil.

C. 2-(3-Trifluoromethylphenoxy)-3-(4-hydroxyphenyl)-2-methyl-propionic acid ethyl ester 3-(4-Benzyloxyphenyl)-2-methyl-3-(2,2,2-trifluoroacetoxy)-2-(3-trifluoromethylphenoxy)-propionic acid ethyl ester (2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to an oil.

D. 2-Methyl-3-(4-{2-[5-methyl-2-(4-thiophen-2-yl-phenyl)-oxazol-4-yl]-ethoxy}-phenyl)-2-(3-trifluoromethyl-phenoxy) -propionic acid A mixture of 2-(3-trifluoromethylphenoxy)-3-(4-hydroxyphenyl)-2-methyl-propionic acid ethyl (0.030 mmol), toluene-4-sulfonic acid 2-(5-methyl-2-(4-thiophen-2-yl-phenyl-oxazol-4-yl)ethyl ester (0.030 mmol) (see Ex. 3, Part B) and 325 mesh $K_2CO_3$ (0.084 g, 0.60 mmol) in ethanol (2 mL) was heated to reflux for 24 h under N$_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-methyl-3-(4-{2-[5-methyl-2-(4-thiophen-2-yl-phenyl)-oxazol-4-yl]-ethoxy}-phenyl)-2-(3-trifluoromethyl-phenoxy)-propionic acid. $^1$H NMR (400 MHz, $CDCl_3$) δ 7.98 (d, 2H, J=8.60 Hz), 7.69 (d, 2H, J=8.60 Hz), 7.41 (dd, 1H, J=3.52 Hz, J=1.17 Hz), 7.36–7.32 (m, 2H), 7.15 (d, 2H, J=8.60 Hz), 7.16–7.10 (m, 3H), 7.05–7.02 (m, 1H), 6.82 (d, 2H, J=8.60 Hz), 4.21 (t, 2H, J=6.26 Hz), 3.27 (d, 1H, J=14.08 Hz), 3.16 (d, 1H, J=14.08 Hz), 3.02 (t, 2H, J=6.26 Hz), 2.43 (s, 3H), 1.46 (s, 3H); HRMS (ES$^+$) m/z exact mass calcd for $C_{33}H_{29}NO_5F_3S$ 608.1718, found 608.

Example 55

3-{4-[2-(2-Biphenyl-3-yl-5-methyl-oxazol-4-yl)-ethoxy]-phenyl}-2-(3-methoxy-phenoxy)-2-methyl-propionic acid

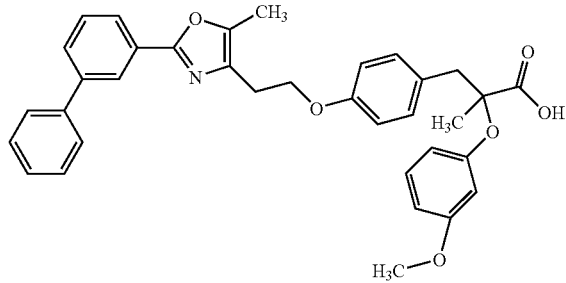

A. 2-(3-Methoxyphenoxy)propionic acid ethyl ester

3-Methoxyphenol (0.30 mol), $Cs_2CO_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over $Na_2SO_4$ and concentrated in vacuo to produce an oil.

B. 3-(4Benzyloxy)-2-(3-methoxyphenoxy)-2-methyl-3-(2,2,2-trifluoroacetoxy)propionic acid ethyl ester A solution of LDA (16.5 mL, 24.7 mmol, 1.5M in cyclohexane) was cooled to −78° C. in a dry ice/acetone bath and then added to a solution 2-(3-methoxyphenoxy)propionic acid ethyl ester (24.7 mmol) in anhydrous THF (30 mL) also cooled to −78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous $NH_4Cl$ (10 mL) and the mixture allowed to warm to ambient temperature. The biphasic mixture was diluted with ether (100 mL) and partitioned, and the organic layer was washed with brine, dried over $MgSO_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxyphenyl)-2-(3-methoxyphenoxy)-3-hydroxy-2-methylpropionic acid ethyl ester which was used without further characterization or purification.

3-(4-Benzyloxyphenyl)-3-hydroxy-2-(3-methoxyphenoxy)-2-methylpropionic acid ethyl ester (13.4 mmol) in anhydrous $CH_2Cl_2$ (100 mL) and pyridine (134 mmol) was cooled to 0° C. and treated with trifluoroacetic anhydride (26.9 mmol). The mixture was stirred for 2 h and gradually warmed to ambient temperature. An aqueous solution of 1N HCl (150 mL) was added and the mixture was stirred vigorously. The solution was partitioned and the organic layer was washed twice with water and brine, dried over $Na_2SO_4$, and concentrated in vacuo to produce 3-(4-benzyloxy)-2-(3-methoxyphenoxy)-2-methyl-3-(2,2,2-trifluoroacetoxy)propionic acid ethyl ester as an oil.

C. 2-(3-Methoxyphenoxy)-3-(4-hydroxyphenyl)-2-methylpropionic acid ethyl ester 3-(4-Benzyloxy)-2-(3-methoxyphenoxy)-2-methyl-3-(2,2,2-trifluoroacetoxy)propionic acid ethyl ester (2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to an oil.

D. 3-{4-[2-(2-Biphenyl-3-yl-5-methyl-oxazol-4-yl)-ethoxy]-phenyl}-2-(3-methoxy-phenoxy)-2-methyl-propionic acid A mixture of 2-(3-methoxyphenoxy)-3-(4-hydroxyphenyl)-2-methyl-propionic acid ethyl (0.030 mmol), toluene-4-sulfonic acid 2-(2-biphenyl-3-yl-5-methyloxazol-4-yl) ethyl ester (0.030 mmol) (see Ex. 2, Part F) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-{4-[2-(2-biphenyl-3-yl-5-methyl-oxazol-4-yl)-ethoxy]-phenyl}-2-(3-methoxy-phenoxy)-2-methyl-propionic acid. $^1$H NMR (400 MHz, $CDCl_3$) δ 8.27 (t, 1H, J=1.76 Hz), 7.97–7.94 (m, 1H), 7.77–7.75 (m, 1H), 7.65–7.64 (m, 2H), 7.56 (t, 1H, J=7.82 Hz), 7.48–7.44 (m, 2H), 7.41–7.39 (m, 1H), 7.17–7.12 (m, 3H), 6.81 (d, 2H, J=8.60 Hz), 6.61–6.58 (m, 1H), 6.49–6.46 (m, 1H), 6.45 (t, 1H, J=2.35 Hz), 4.23 (t, 2H, J=5.86 Hz), 3.74 (s, 3H), 3.24 (d, 1H, J=14.08 Hz), 3.13–3.10 (m, 3H), 2.46 (s, 3H), 1.43 (s, 3H); HRMS (ES$^+$) m/z exact mass calcd for $C_{35}H_{34}NO_6$ 564.2386, found 564.2375

Example 56

3-{4-[2-(2-Biphenyl-4-yl-5-methyl-oxazol-4-yl)-ethoxy]-phenyl}-2-(3-methoxy-phenoxy)-2-methyl-propionic acid

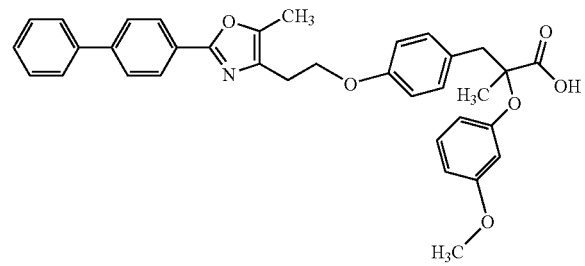

A. 3-{4-[2-(2-Biphenyl-4-yl-5-methyl-oxazol-4-yl)-ethoxy]-phenyl}-2-(3-methoxy-phenoxy)-2-methyl-propionic acid A mixture of 2-(3-methoxyphenoxy)-3-(4-hydroxyphenyl)-2-methyl-propionic acid ethyl (0.030 mmol) (see Ex.

55, Part C), toluene-4-sulfonic acid 2-(5-methyl-2-biphenyl-4-yl-oxazol-4-yl)ethyl ester (0.030 mmol) (see Ex. 1, Part I) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-{4-[2-(2-biphenyl-4-yl-5-methyl-oxazol-4-yl)-ethoxy]-phenyl}-2-(3-methoxy-phenoxy)-2-methyl-propionic acid. $^1$H NMR (400 M&, $CDCl_3$) δ 8.06 (d, 2H, J=8.21 Hz), 7.71–7.67 (m, 3H), 7.65–7.62 (m, 2H), 7.48–7.44 (m, 2H), 7.41–7.37 (m, 1H), 7.18–7.12 (m, 2H), 6.82 (d, 2H, J=8.60 Hz), 6.61–6.45 (m, 3H), 4.22 (t, 2H, J=6.25 Hz), 3.74 (s, 3H), 3.25 (d, 1H, J=14.08 Hz), 3.13 (d, 1H, J=14.08 Hz), 3.07 (t, 2H, J=6.25 Hz) 2.43 (s, 3H), 1.44 (s, 3H); HRMS ($ES^+$) m/z exact mass calcd for $C_{35}H_{34}NO_6$ 564.2386, found 564.2388

Example 57

2-(3-Methoxy-phenoxy)-2-methyl-3-(4-{2-[5-methyl-2-(4-thiophen-2-yl-phenyl)-oxazol-4-yl]-ethoxy}-phenyl)-propionic acid

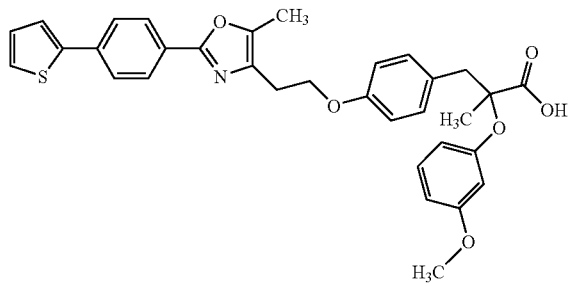

A. 2-(3-Methoxy-phenoxy)-2-methyl-3-(4-{2-[5-methyl-2-(4-thiophen-2-yl-phenyl)-oxazol-4-yl]-ethoxy}-phenyl)-propionic acid A mixture of 2-(3-methoxyphenoxy)-3-(4-hydroxyphenyl)-2-methyl-propionic acid ethyl (0.030 mmol) (see Ex. 55, Part C), Toluene-4-sulfonic acid 2-(5-methyl-2-(4-thiophen-2-yl-phenyl)-oxazol-4-yl)ethyl ester (0.030 mmol) (see Ex. 3, Part B) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-(3-methoxy-phenoxy)-2-methyl-3-(4-{2-[5-methyl-2-(4-thiophen-2-yl-phenyl)-oxazol-4-yl]-ethoxy}-phenyl)-propionic acid. $^1$H NMR (400 MHz, $CDCl_3$) δ 7.99 (d, 2H, J=8.60 Hz), 7.71 (d, 2H, J=8.60 Hz), 7.42–7.40 (m, 1H), 7.36–7.35 (m, 1H), 7.18–7.10 (m, 4H), 6.81 (d, 2H, J=8.60 Hz), 6.61–6.59 (m, 1H), 6.49–6.45 (m, 2H), 4.21 (t, 2H, J=6.26 Hz), 3.74 (s, 3H), 3.25 (d, 1H, J=14.08 Hz), 3.13 (d, 1H, J=14.08 Hz), 3.07 (t, 2H, J=6.26 Hz) 2.43 (s, 3H), 1.43 (s, 3H); HRMS ($ES^+$) m/z exact mass calcd for $C_{33}H_{32}NO_6S$ 570.1950, found 570.1950

Example 58

2-(Benzo[1,3]dioxol-5-yloxy)-3-{4-[2-(2-biphenyl-3-yl-5-methyl-oxazol-4-yl)-ethoxy]-phenyl}-2-methyl-propionic acid

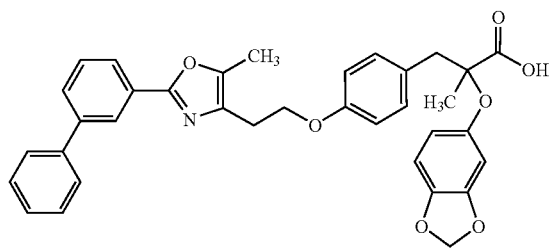

A. 2-(Benzo[1,3]dioxol-5-yloxy)propionic acid ethyl ester

5-Hydroxybenzo[1,3]dioxole (0.30 mol), $Cs_2CO_3$ (197.0 g, 0.61 mol), and ethyl 2-bromopropionate (54.3 g, 0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine, The organic layer was dried over $Na_2SO_4$ and concentrated in vacuo to produce an oil.

B. 2-(Benzo[1,3]dioxol-5-yloxy)-3-(4-benzyloxyphenyl)-2-methyl-3-(2,2,2-trifluoroacetoxy)propionic acid ethyl ester A solution of LDA (16.5 mL, 24.7 mmol, 1.5M in cyclohexane) was cooled to −78° C. in a dry ice/acetone bath and then added to a solution 2-(benzo[1,3]dioxol-5-yloxy)-propionic acid ethyl ester (24.7 mmol) in anhydrous THF (30 mL) also cooled to −78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous $NH_4Cl$ (10 mL) and the mixture allowed to warm to ambient temperature. The biphasic mixture was diluted with ether (100 mL) and partitioned, and the organic layer was washed with brine, dried over $MgSO_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 3-(4-benzyloxy-phenyl)-2-(benzo[1,3]dioxol-5-yloxy)-3-hydroxy-2-methylpropionic acid ethyl ester which was used without further characterization or purification.

3-(4-Benzyloxyphenyl)-2-(benzo[1,3]dioxol-5-yloxy)-3-hydroxy-2-methylpropionic acid ethyl ester (13.4 mmol) in anhydrous $CH_2Cl_2$ (100 mL) and pyridine (134 mmol) was cooled to 0° C. and treated with trifluoroacetic anhydride (26.9 mmol). The mixture was stirred for 2 h and gradually warmed to ambient temperature. An aqueous solution of 1N HCl (150 mL) was added and the mixture was stirred vigorously. The solution was partitioned and the organic layer was washed twice with water and brine, dried over $Na_2SO_4$, and concentrated in vacuo to produce 3-(4-benzyloxyphenyl)-2-(benzo[1,3]dioxol-5-yloxy)-2-methyl-3-(2,2,2-trifluoroacetoxy)propionic acid ethyl ester as an oil.

C. 2-(Benzo[1,3]dioxol-5-yloxy)-3-(4-hydroxyphenyl)-2-methyl-propionic acid ethyl ester 3(4-Benzyloxyphenyl)-2-(benzo[1,3]dioxol-5-yloxy)-2-methyl-3-(2,2,2-trifluoroacetoxy)propionic acid ethyl ester (2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to an oil. 2-(Benzo[1,3]dioxol-5-yloxy)-3-{4-[2-(2-biphenyl-3-yl-5-methyl-oxazol-4-yl)-ethoxy]-phenyl}-2-methyl-propionic acid: A mixture of 2-(benzo[1,3]dioxol-5-yloxy)-3-(4-hydroxyphenyl)-2-methyl-propionic acid ethyl ester (0.030 mmol), toluene-4-sulfonic acid 2-(2-biphenyl-3-yl-5-methyloxazol-4-yl)ethyl ester (0.030 mmol) (see Ex. 2, Part F) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-(benzo[1,3]dioxol-5-yloxy)-3-{4-[2-(2-biphenyl-3-yl-5-methyl-oxazol-4-yl)-ethoxy]-phenyl}-2-methyl-propionic acid. $^1$H NMR (400 MHz, $CDCl_3$) δ 8.19 (t, 1H, J=1.71 Hz), 7.91–7.89 (m, 1H), 7.65–7.59 (m, 3H), 7.48 (t, 1H, J=7.57 Hz), 7.43–7.39 (m, 2H), 7.35–7.31 (m, 1H), 7.13 (d, 2H, J=8.79 Hz), 6.79 (d, 2H, J=8.30 Hz), 6.60 (d, 1H, J=8.30 Hz), 6.41 (d, 1H, J=2.44 Hz), 6.32 (dd, 1H, J=8.30 Hz, J=2.44 Hz), 5.87 (d, 2H, J=0.98 Hz), 4.19 (t, 2H, J=6.35 Hz), 3.15 (d, 1H, J=14.17 Hz), 304–2.99 (m, 3H), 2.38 (s, 3H), 1.30 (s, 3H); HRMS (ES$^+$) m/z exact mass calcd for $C_{35}H_{32}NO_7$ 578.2179, found 578.2190.

Example 59

2-(Benzo[1,3]dioxol-5-yloxy)-3-{4-[2-(2-biphenyl-4-yl-5-methyl-oxazol-4-yl)-ethoxy]-phenyl}-2-methyl-propionic acid

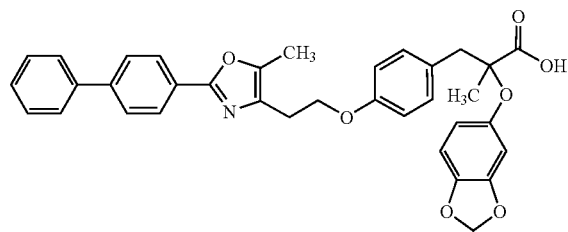

A. 2-(Benzo[1,3]dioxol-5-yloxy)-3-{4-[2-(2-biphenyl-4-yl-5-methyl-oxazol-4-yl)-ethoxy]-phenyl}-2-methyl-propionic acid A mixture of 2-(benzo[1,3]dioxol-5-yloxy)-3-(4-hydroxyphenyl)-2-methyl-propionic acid ethyl ester (0.030 mmol) (see Ex. 58, Part C), toluene-4-sulfonic acid 2-(5-methyl-2-biphenyl-4-yl-oxazol-4-yl)ethyl ester (0.030 mmol) (see Ex. 1, Part I) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-(benzo[1,3]dioxol-5-yloxy)-3-}4-[2-(2-biphenyl-4-yl-5-methyl-oxazol-4-yl)-ethoxy]-phenyl}-2-methyl-propionic acid. $^1$H NMR (400 MHz, $CDCl_3$) δ 8.00 (d, 2H, J=8.79 Hz), 7.63 (d, 2H, J=8.31 Hz), 7.59 (d, 2H, J=8.79 Hz), 7.43–7.33 (m, 3H), 7.14 (d, 2H, J=8.79 Hz), 6.80 (d, 2H, J=8.30 Hz), 6.61 (d, 1H, J=8.79 Hz), 6.41 (d, 1H, J=2.44 Hz), 6.32 (dd, 1H, J=8.30 Hz, J=2.44 Hz), 5.88 (s, 2H), 4.20 (t, 2H, J=6.25 Hz), 3.05 (d, 1H, J=14.08 Hz), 3.04–2.99 (m, 3H), 2.37 (s, 3H), 1.36 (s, 3H); HRMS (ES$^+$) m/z exact mass calcd for $C_{35}H_{32}NO_7$ 578.2179, found 578.2209

Example 60

2-(Benzo[1,3]dioxol-5-yloxy)-2-methyl-3-(4-{2-[5-methyl-2-(3-thiophen-2-yl-phenyl)-oxazol-4-yl]-ethoxy}-phenyl)-propionic acid

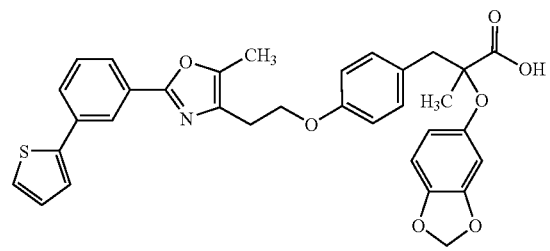

A. 2-(Benzo[1,3]dioxol-5-yloxy)-2-methyl-3-(4-{2-[5-methyl-2-(3-thiophen-2-yl-phenyl)-oxazol-4-yl]-ethoxy}-phenyl)-propionic acid A mixture of 2-(benzo[1,3]dioxol-5-yloxy)-3-(4-hydroxyphenyl)-2-methyl-propionic acid ethyl ester (0.030 mmol) (see Ex. 58, Part C), toluene-4-sulfonic acid 2-[5-methyl-2-(3-thiophen-2-ylphenyl)oxazol-4-yl]ethyl ester (0.030 mmol) (see Ex. 5, Part B) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-(benzo[1,3]dioxol-5-yloxy)-2-methyl-3-(4-{2-[5-methyl-2-(3-thiophen-2-yl-phenyl)-oxazol-4-yl]-ethoxy}-phenyl)-propionic acid. $^1$H NMR (400 MHz, $CDCl_3$) δ 8.19 (t, 1H, J=1.71 Hz), 7.85–7.82 (m, 1H), 7.67–7.63 (m, 1H), 7.42 (t, 1H, J=7.82 Hz), 7.38–7.37 (m, 1H), 7.28–7.26 (m, 1H), 7.13 (d, 2H, J=8.79 Hz), 7.06 (dd, 1H, J=4.88 Hz, J=3.42 Hz), 6.79 (d, 2H, J=8.79 Hz), 6.60 (d, 1H, J=8.30 Hz), 6.40 (d, 1H, J=2.44 Hz), 6.32 (dd, 1H, J=8.30 Hz, J=2.44 Hz), 5.87 (d, 2H, J=0.98 Hz), 4.19 (t, 2H, J=6.11 Hz), 3.15 (d, 1H, J=14.17 Hz), 3.04–3.01 (m, 3H), 2.39 (s, 3H), 1.30 (s, 3H);HRMS (ES$^+$) m/z exact mass calcd for $C_{33}H_{30}NO_7S$ 584.1743, found 584.1744.

Example 61

2-{4-[2-(2-Biphenyl-4-yl-5-methyl-oxazol-4-yl)-ethoxy]-benzyl}-2-phenoxy-hexanoic acid

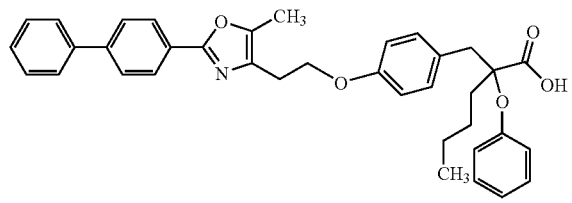

A. 2-Phenoxyhexanoic acid ethyl ester

Phenol (28.5 g, 0.30 mol), $Cs_2CO_3$ (197.0 g, 0.61 mol), and ethyl 2-bromohexanoate (0.30 mol) were combined in anhydrous DMF (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over $Na_2SO_4$ and concentrated in vacuo to produce an oil.

B. 2-(4-Benzyloxybenzyl)-2-phenoxy-3-(2,2,2-trifluoroacetoxy)hexanoic acid ethyl ester A solution of LDA (16.5 mL, 24.7 mmol, 1.5M in cyclohexane) was cooled to −78° C. in a dry ice/acetone bath and then added to a solution of 2-phenoxyhexanoic acid ethyl ester (24.7 mmol) in anhydrous THF (30 mL) also cooled to −78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous $NH_4Cl$ (10 mL) and the mixture allowed to warm to ambient temperature. The biphasic mixture was diluted with ether (100 mL) and partitioned, and the organic layer was washed with brine, dried over $MgSO_4$ and concentrated in vacuo. The residue was purified by flash column chromatography (600 g silica, 25×200 mL fractions, gradient elution 0–20% ethyl acetate in hexanes) to provide an oil as a mixture of inseparable diastereomers of 2-[(4-benzyloxyphenyl)-hydroxymethyl]-2-phenoxy-hexanoic acid ethyl ester which was used without further characterization or purification.

2-[(4-Benzyloxyphenyl)-hydroxymethyl]-2-phenoxy-hexanoic acid ethyl ester (13.4 mmol) in anhydrous $CH_2Cl_2$ (100 mL) and pyridine (134 mmol) was cooled to 0° C. and treated with trifluoroacetic anhydride (26.9 mmol). The mixture was stirred for 2 h and gradually warmed to ambient temperature. An aqueous solution of 1N HCl (150 mL) was added and the mixture was stirred vigorously. The solution was partitioned and the organic layer was washed twice with water and brine, dried over $Na_2SO_4$, and concentrated in vacuo to produce 2-(4-benzyloxybenzyl)-2-phenoxy-3-(2,2,2-trifluoroacetoxy)hexanoic acid ethyl ester as an oil.

C. 2-(4-Hydroxybenzyl)-2-phenoxyhexanoic acid ethyl ester 2-(4-Benzyloxybenzyl)-2-phenoxy-3-(2,2,2-trifluoroacetoxy)hexanoic acid ethyl ester (2.1 mmol) was dissolved in ethyl acetate (30 mL) and treated with 5% palladium on carbon (300 mg), and stirred under an atmosphere of hydrogen for 20 h. The suspension was filtered through celite and concentrated in vacuo to an oil.

D. 2-{4-[2-(2-Biphenyl-4-yl-5-methyl-oxazol-4-yl)-ethoxy]-benzyl}-2-phenoxy-hexanoic acid A mixture of 2-(4-hydroxybenzyl)-2-phenoxyhexanoic acid ethyl ester (0.030 mmol), toluene-4-sulfonic acid 2-(5-methyl-2-biphenyl-4-yl-oxazol-4-yl)ethyl ester (0.030 mmol) (see Ex. 1, Part I) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-{4-[2-(2-biphenyl-4-yl-5-methyl-oxazol-4-yl)-ethoxy]-benzyl}-2-phenoxy-hexanoic acid. $^1$H NMR (400 MHz, $CDCl_3$) δ 8.02 (d, 2H, J=8.60 Hz), 7.65–7.61 (m, 4H), 7.46 (t, 2H, J=7.62 Hz), 7.38–7.26 (m, 3H), 7.07–6.96 (m, 5H), 6.76 (d, 2H, J=8.60 Hz), 4.18 (t, 2H, J=6.65 Hz), 3.29 (s, 2H), 2.97 (t, 2H, J=6.65 Hz), 2.38 (s, 3H), 2.08–1.98 (m, 2H), 1.42–1.18 (m, 4H), 0.79 (t, 3H, J=7.04 Hz); MS ($ES^+$) calcd for $C_{37}H_{38}NO_5$: Found m/e 576.3 (M+1, 100%).

Example 62

2-{4-[2-(2-Biphenyl-3-yl-5-methyl-oxazol-4-yl)-ethoxy]-benzyl}-2-phenoxy-hexanoic acid

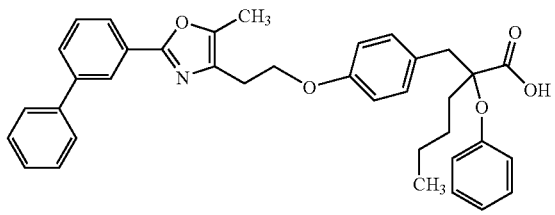

A. 2-{4-[2-(2-Biphenyl-3-yl-5-methyl-oxazol-4-yl)-ethoxy]-benzyl}-2-phenoxy-hexanoic acid A mixture of 2-(4-hydroxybenzyl)-2-phenoxyhexanoic acid ethyl ester (0.030 mmol) (see Ex 61, Part C), toluene-4-sulfonic acid 2-(2-biphenyl-3-yl-5-methyloxazol-4-yl) ethyl ester (0.030 mmol) (see Ex. 2, Part F) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-{4-[2-(2-biphenyl-3-yl-5-methyl-oxazol-4-yl)-ethoxy]-benzyl}-2-phenoxy-hexanoic acid. $^1$H NMR (400 MHz, $CDCl_3$) δ 8.12 (t, 1H, J=1.56 Hz), 7.86 (d, 1H, J=7.82 Hz), 7.58–7.54 (m, 3H), 7.42–7.35 (m, 3H), 7.30–7.18 (m, 3H), 6.97 (t, 1H, J=7.23 Hz), 6.93–6.87 (m, 4H), 6.68 (d, 2H, J=8.60 Hz), 4.11 (t, 2H, J=6.65 Hz), 3.21 (s, 2H), 2.89 (t, 2H, J=6.65 Hz), 2.29 (s, 3H), 2.02–1.89 (m, 2H), 1.33–1.09 (m, 4H), 0.71 (t, 3H, J=7.04 Hz); MS ($ES^+$) calcd for $C_{37}H_{38}NO_5$: Found m/e 576.3 (M+1, 100%).

Example 63

2-(4-{2-[5-Methyl-2-(3-thiophen-2-yl-phenyl)-oxazol-4-yl]-ethoxy}-benzyl)-2-phenoxy-hexanoic acid

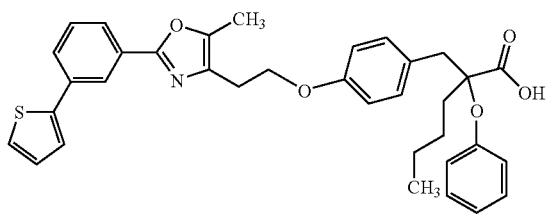

A. 2-(4-{2-[5-Methyl-2-(3-thiophen-2-yl-phenyl)-oxazol-4-yl]-ethoxy}-benzyl)-2-phenoxy-hexanoic acid

A mixture of 2-(4-hydroxybenzyl)-2-phenoxyhexanoic acid ethyl ester (0.030 mmol) (see Ex 61, Part C), toluene-4-sulfonic acid 2-[5-methyl-2-(3-thiophen-2-ylphenyl)oxazol-4-yl]ethyl ester (0.030 mmol) (see Ex. 5, Part B) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 2-(4-{2-[5-methyl-2-(3-thiophen-2-yl-phenyl)-oxazol-4-yl]-ethoxy}-benzyl)-2-phenoxy-hexanoic acid. $^1$H NMR (400 MHz, $CDCl_3$) δ 8.15–8.12 (m, 1H), 7.79 (d, 1H, J=7.43 Hz), 7.57 (d, 1H, J=7.82 Hz), 7.37–7.32 (m, 2H), 7.24–7.18 (m, 3H), 7.01 (dd, 1H, J=5.08 Hz, J=3.52 Hz), 6.99–6.87 (m, 5H), 6.68 (d, 2H, J=8.99 Hz), 4.10 (t, 2H, J=6.65 Hz), 3.21 (s, 2H), 2.91 (t, 2H, J=6.65 Hz), 2.31 (s, 3H), 2.02–1.88 (m, 2H), 1.34–1.08 (m, 4H), 0.71 (t, 3H, J=7.04 Hz); MS (ES$^+$) calcd for $C_{35}H_{36}NO_5S$: Found m/e 582.2 (M+1, 100%).

Example 64

3-{4-[2-(2-Biphenyl-3-yl-5-methyl-oxazol-4-yl)-ethoxy]-phenyl}-2-methyl-2-p-tolyloxy-propionic acid

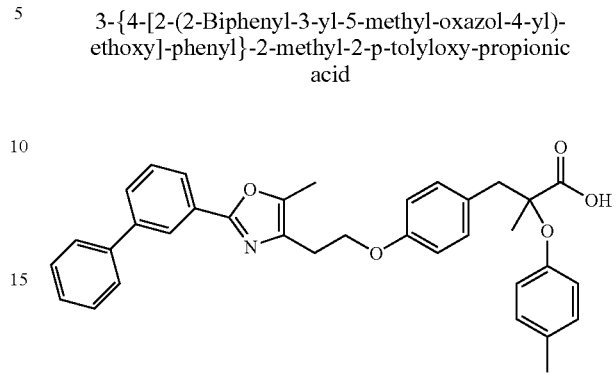

A. 3-{4-[2-(2-Biphenyl-3-yl-5-methyl-oxazol-4-yl)-ethoxy]-phenyl}-2-methyl-2-p-tolyloxy-propionic acid

A mixture 2-(p-tolyloxy)-3-(4-hydroxyphenyl)-2-methyl-propionic acid ethyl ester (0.030 mmol) (see Ex 35, Part D), toluene-4-sulfonic acid 2-(2-biphenyl-3-yl-5-methyloxazol-4-yl)ethyl ester (0.030 mmol) (see Ex. 2, Part F) and 325 mesh $K_2CO_3$ (0.084 g, 0.60 mmol) in ethanol (2 mL) was heated to reflux for 24 h under $N_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and $CH_2Cl_2$ and the organic layer dried by passing it through a Varian Chem Elut 1003 cartridge. The solvent was removed in vacuo to give 3-{4-[2-(2-Biphenyl-3-yl-5-methyl-oxazol-4-yl)-ethoxy]-phenyl}-2-methyl-2-p-tolyloxy-propionic acid.

The compound in Table 1 were made by the methods discribed above:

| EXAMPLE | STRUCTURAL FORMULA |
|---|---|
| 65 | 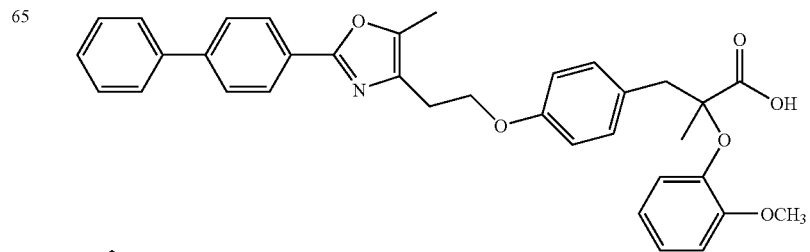 |
| 66 | 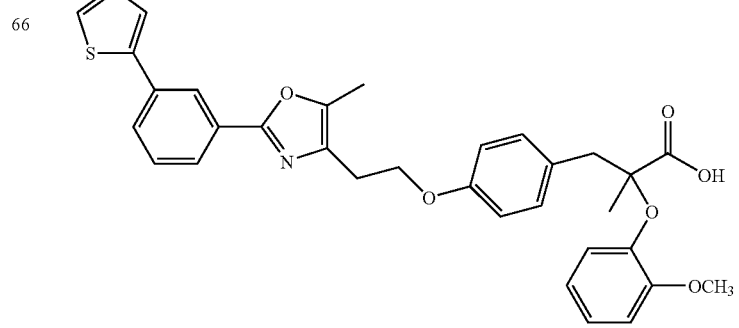 |

| EXAMPLE | STRUCTURAL FORMULA |
|---|---|
| 67 | 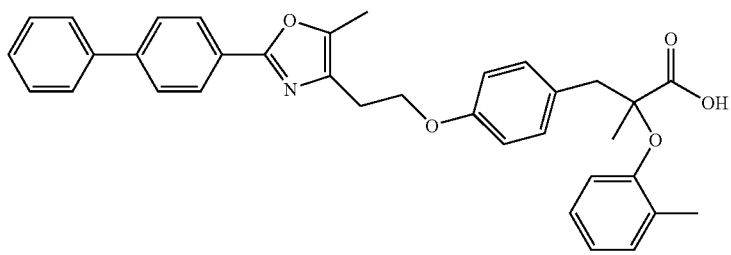 |
| 68 | 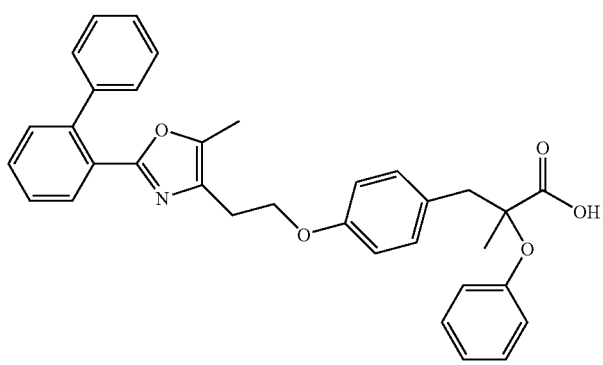 |

Example 71

3-{4-[2-(2-Biphenyl-4-yl-5-methyl-oxazol-4-yl)-ethoxy]-phenyl}-2-(2-methoxy-phenoxy)-2-methyl-propionic acid Step A

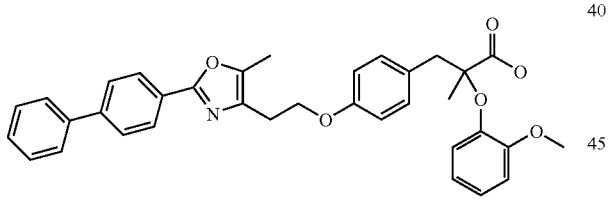

2-(2-Methoxy-phenoxy)-propionic acid ethyl ester: Cesium carbonate (53.86 g, 165.3 mmol) was added to a solution of 2-methoxyphenol (10.26 g, 82.6 mmol) in anhydrous DMF (500 mL) at room temperature under an atmosphere of nitrogen. After five minutes, ethyl 2-bromopropionate (10.7 mL, 82.6 mmol, d=1.394) was added rapidly dropwise and the resultant mixture was allowed to stir at 90° C. for 18 h. The reaction mixture was diluted with diethyl ether, then extracted twice with 1N HCl and twice with water. The organic layer was dried over MgSO$_4$ and concentrated in vacuo. The residue was purified by flash chromatography (25% ether in hexanes) to provide the titled compound (16.97 g, 92%) as a light yellow oil. $^1$H NMR (400 MHz, CDCl$_3$): δ 6.96–6.80 (m, 4H), 4.73 (q, 1H, J=7.04 Hz), 4.23–4.12 (m, 2H), 3.82 (s, 3H), 1.62 (d, 3H, J=6.65 Hz), 1.21(t, 3H, J=7.04 Hz). MS [ES+] m/z exact mass calcd for C$_{12}$H$_{17}$O$_4$ 225.1127, found 225.1110. R$_f$=0.19 in 25% ether in hexanes.

Step B

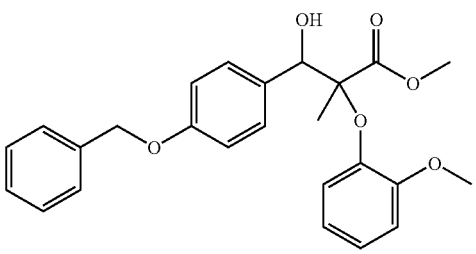

3-(4-Benzyloxy-phenyl)-3-hydroxy-2-(2-methoxy-phenoxy)-2-methyl-propionic acid ethyl ester: A solution of LDA (32.1 mL, 107.1 mmol, 1.5M in cyclohexane) in anhydrous THF (60 mL) was cooled to −78° C. in a dry ice/acetone bath and added to a solution of 2-(2-Methoxy-phenoxy)-propionic acid ethyl ester in anhydrous THF (60 mL) also cooled to −78° C. under an atmosphere of nitrogen. After five minutes, 4-benzyloxybenzaldehyde (5.11 g, 24.1 mmol) was added in one portion. After stirring for one minute, the reaction mixture was quenched with acetic acid (4.6 mL, 80.3 mmol, d=1.049) and a saturated solution of aqueous NH₄Cl (50 mL). The biphasic mixture was allowed to warm to room temperature and diluted with diethyl ether (1 L). The organic layer was washed with water, dried over MgSO₄, and concentrated in vacuo. The residue was purified by flash column chromatography (20% ethyl acetate in hexanes) to provide a mixture of diastereomers of 3-(4-Benzyloxy-phenyl)-3-hydroxy-2-(2-methoxy-phenoxy)-2-methyl-propionic acid ethyl ester (7.62 g, 65%). ¹H NMR (400 MHz, CDCl₃): δ 7.53–7.34 (m, 5H), 7.09–7.00 (m, 2H), 6.91–6.86(m, 2H), 6.78(td, 1H, J=8.0 Hz, 1.6 Hz), 6.65(dd, 1H, J=8.0 Hz, 1.6 Hz), 6.44–6.43 (m, 3H), 5.12–5.08 (m, 2H), 4.39–4.18 (m, 2H), 3.72–3.67 (m, 3H), 1.41 (s, 1H), 1.34–1.26 (m, 6H). $R_f$=0.42 in 25% ethyl acetate in hexanes.

Step C

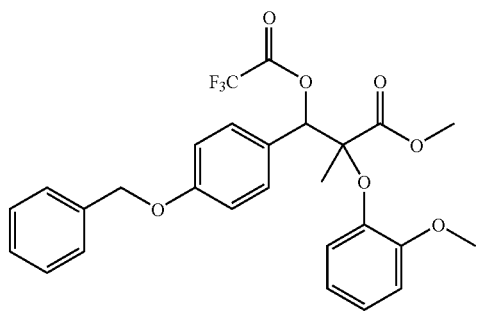

3-(4-Benzyloxy-phenyl)-2-(2-methoxy-phenoxy)-2-methyl-3-(2,2,2-trifluoro-acetoxy)-propionic acid ethyl ester: 3-(4-Benzyloxy-phenyl)-3-hydroxy-2-(2-methoxy-phenoxy)-2-methyl-propionic acid ethyl ester (7.62 g, 17.5 mmol) in anhydrous CH₂Cl₂ (150 mL) was cooled to 0° C. and treated with pyridine (14 mL, 174.6 mmol, d=0.987). Trifluoroacetic anhydride (7.4 mL, 52.4 mmol, d=1.487) was added dropwise and the mixture was stirred for 2 h, gradually warming to ambient temperature, The reaction mixture was diluted with diethyl ether and washed with 1N HCl, then water. The organic layer was dried over Na₂SO₄ and concentrated in vacuo to provide the titled compound (8.77 g, 100%) which was used without purification.

3-(4-Hydroxy-phenyl)-2-(2-methoxy-phenoxy)-2-methyl-propionic acid ethyl ester: 3-(4-Benzyloxy-phenyl)-2-(2-methoxy-phenoxy)-2-methyl-3-(2,2,2-trifluoro-acetoxy)-propionic acid ethyl ester was dissolved in ethyl acetate (350 mL), treated with 5% palladium on carbon (8.77 g), and stirred under an atmosphere of hydrogen for 48 h. The suspension was filtered through celite and concentrated in vacuo. The residue was purified by flash column chromatography (25% ethyl acetate in hexanes) to provide the title compound as a light yellow oil (1.73 g, 25%). ¹H NMR (400 MHz, CDCl₃): δ 7.12 (d, 2H, J=6.65 Hz), 6.98–6.93 (m, 5H), 4.24–4.15 (m, 2H), 3.75 (s, 3H), 3.23 (d; 1H, J=13.69 Hz), 3.13 (d, 1H, J=13.69 Hz), 1.30 (s, 3H), 1.22 (t, 3H, J=7.43 Hz). MS [EI+] 331 (M+H)⁺, [EI−] 329 (M−H)⁺. $R_f$=0.14 in 25% ethyl acetate in hexanes.

Step E

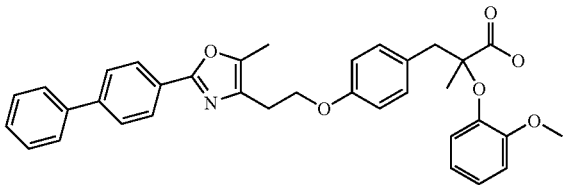

3-{4-[2-(2-Biphenyl-4-yl-5-methyl-oxazol-4-yl)-ethoxy]-phenyl}-2-(2-methoxy-phenoxy)-2-methyl-propionic acid; Potassium carbonate (0.048 g, 0.35 mmol) was added to a solution of 3-(4-Hydroxy-phenyl)-2-(2-methoxy-phenoxy)-2-methyl-propionic acid ethyl ester and toluene-4-sulfonic acid 2-(2-biphenyl-4-yl-5-methyl-oxazol-4-yl)-ethyl ester in 4A sieve-dried ethanol (2 mL). The resultant mixture was stirred at 80° C. under an atmosphere of nitrogen for 18 h, then diluted with ethanol (2 mL). 5N NaOH (0.5 mL) was added, then the reaction mixture was refluxed for 2 h. The reaction mixture was concentrated in vacuo, diluted with 1N HCl, and extracted with CH₂Cl₂. The organic layer was dried through a Varian ChemElut cartridge, concentrated in vacuo, and purified by LCMS. ¹H NMR (400 MHz, CDCl₃): δ 8.05 (d, 2H, J=7.82 Hz), 7.70 (d, 2H, J=8.21 Hz), 7.62 (d, 2H, J=7.82 Hz), 7.45 (t, 2H, J=7.82 Hz), 7.39–7.36 (m, 1H), 7.19 (d, 2H, J=8.21), 6.88 (d, 1H, J=8.21 Hz), 6.84–6.80 (m, 3H), 6.63 (d, 1H, J=7.82 Hz), 4.22 (t, 2H, J=5.87 Hz), 3.82 (s, 3H), 3.30 (d, 1H, J=14.08 Hz), 3.08 (dd, 3H, J=9.78 Hz, 3.52 Hz), 2.43 (s, 3H), 1.30(s, 2H), 1.23 (s, 1H). MS [ES+] m/z exact mass calcd for C35H34NO6 564.2386, found 564.2407.

Example 72

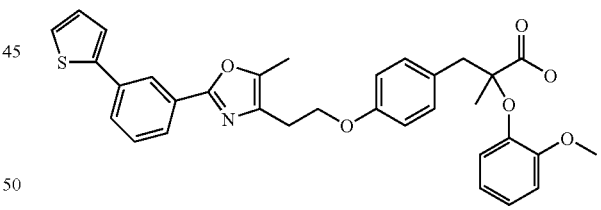

2-(2-Methoxy-phenoxy)-2-methyl-3-(4-{2-[5-methyl-2-(3-thiophen-2-yl-phenyl)-oxazol-4-yl]-ethoxy}-phenyl)-propionic acid;: The title compound was prepared using the representative Standard Procedure (E) from 3-(4-Hydroxy-phenyl)-2-(2-methoxy-phenoxy)-2-methyl-propionic acid ethyl ester and toluene-4-sulfonic acid 2-[5-methyl-2-(3-thiophen-2-yl-phenyl)-oxazol-4-yl]-ethyl ester. ¹H NMR (400 MHz, CDCl₃): δ 8.05 (d, 2H, J=7.82 Hz), 7.86 (d, 2H, J=8.21 Hz), 7.68 (d, 2H, J=7.82 Hz), 7.45 (t, 1H, J=7.65 Hz), 7.41–7.40 (m, 1H), 7.31–7.30 (m, 1H), 7.19(d, 1H, J=8.40 Hz), 7.10–7.04 (m, 2H), 6.88–6.79 (m, 2H), 6.61 (dd, 1H, J=8.40 Hz, 1.65 Hz), 4.22 (t, 2H, J=5.87 Hz), 3.82 (s, 3H), 3.30 (d, 1H, J=14.08 Hz), 3.10–3.03 (m, 3H), 2.43 (s, 3H), 1.30 (s, 3H). MS [ES+] m/z exact mass calcd for C₃₃H₃₂NO₆S 570.1950, found 570.1958.

Example 72

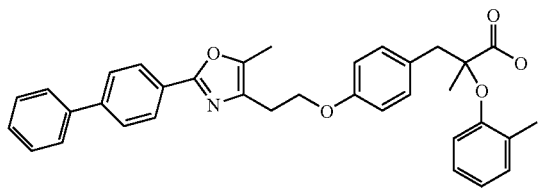

3-{4-[2-(2-Biphenyl-4-yl-5-methyl-oxazol-4-yl)-ethoxy]-phenyl}-2-methyl-2-o-tolyloxy-propionic acid: The title compound was prepared using the representative Standard Procedure (E) from 3-(4-Hydroxy-phenyl)-2-methyl-2-o-tolyloxy-propionic acid ethyl ester and toluene-4-sulfonic acid 2-(2-biphenyl-4-yl-5-methyl-oxazol-4-yl)-ethyl ester. $^1$H NMR (400 MHz, CDCl$_3$): δ 8.02 (d, 2H, J=8.21 Hz), 7.65 (d, 2H, J=8.60 Hz), 7.61 (d, 2H, J=7.04 Hz), 7.44 (t, 2H, J=7.43 Hz), 7.38–7.34 (m, 1H), 7.13 (d, 3H, J=8.60 Hz), 7.09–7.05 (d, 3H), 7.09–7.05 (m, 1H), 6.91(t, 1H, J=7.04 Hz), 6.82–6.79 (m, 3H), 4.19 (t, 2H, J=6.65 Hz), 3.27 (d, 1H, J=14.08 Hz), 3.19 (d, 1H, J=14.08 Hz), 3.01 (t, 2H, J=6.26 Hz), 2.39* (s, 3H), 2.17 (s, 3H), 1.49 (s, 3H). MS [EI+] 548 (M+H)$^+$, [EI−] 546 (M−H)$^+$.

Example 74

Binding and Cotransfection Studies

DNA-dependent binding (ABCD binding) was carried out using SPA technology with PPAR receptors. Tritium-labeled PPARα and PPARγ agonists were used as radioligands for generating displacement curves and IC$_{50}$ values with compounds of the invention. Cotransfection assays were carried out in CV-1 cells. The reporter plasmid contained an acyl-CoA oxidase (AOX) PPRE and TK promoter upstream of the luciferase reporter cDNA. Appropriate PPARs and RXRα were constitutively expressed using plasmids containing the CMV promoter. For PPARα and PPARγ, interference by endogenous PPARγ in CV-1 cells was an issue. In order to eliminate such interference, a GAL4 chimeric system was used in which the DNA binding domain of the transfected PPAR was replaced by that of GAL4, and the GAL4 response element was utilized in place of the AOX PPRE. Cotransfection efficacy was determined relative to PPARα agonist and PPARβ agonist reference molecules. Efficacies were determined by computer fit to a concentration-response curve, or in some cases at a single high concentration of agonist (10 μM). For binding or cotransfection studies with receptors other than PPARs, similar assays were carried out using appropriate ligands, receptors, reporter constructs, etc., for that particular receptor.

These studies were carried out to evaluate the ability of compounds of the invention to bind to and/or activate various nuclear transcription factors, particularly huPPARα ("hu" indicates "human") and huPPARγ. These studies provide in vitro data concerning efficacy and selectivity of compounds of the invention. Furthermore, binding and cotransfection data for compounds of the invention were compared with corresponding data for marketed compounds that act on either huPPARα or huPPARγ.

Binding and cotransfection data for representative compounds of the invention are compared with corresponding data for reference compounds in Table 2.

TABLE 2

Comparison of binding IC$_{50}$ values and cotransfection efficacy data of compounds of the invention to reference compounds.

| | huPPARα | | huPPARγ | |
|---|---|---|---|---|
| Example | IC$_{50}$(nM) | CTF Efficacy (%) | IC$_{50}$(nM) | CTF Efficacy (%) |
| 4 | 147 | 38 | 41 | 93 |
| 7 | 4124 | 60 | 174 | 93 |
| 8 | 605 | 45 | 41 | 91 |
| 15 | 196 | 96 | 107 | 90 |
| 17 | 186 | 116 | 119 | 80 |
| 22 | 260 | 63 | 78 | 100 |
| 26 | 159 | 54 | 55 | 100 |
| 34 | 165 | 61 | 40 | 95 |
| 41 | 402 | 44 | 45 | 108 |
| 42 | 310 | 49 | 56 | 105 |
| 48 | 182 | 45 | 54 | 145 |
| 51 | 203 | 43 | 56 | 160 |
| 56 | 613 | 70 | 99 | 88 |
| 58 | 145 | 48 | 37 | 101 |
| Troglitazone | 94,500 | 0 | 1180 | 80 |
| Fenofibric acid | 68,000 | 16 | 125,000 | 0 |

Example 75

Evaluation of Triglyceride and Cholesterol Levels in Hu apoAI Transgenic Mice Five to six week old male mice, transgenic for human apoAI [C57B1/6-tgn(apoa1) 1rub, Jackson Laboratory, Bar Harbor, Me.] were housed five per cage (10"×20"8" with aspen chip bedding) with food (Purina 5001) and water available at all times. After an acclimation period of 2 weeks, animals were individually identified by ear notches, weighed, and assigned to groups based on body weight. Beginning the following morning, mice were dosed daily by oral gavage for 7 days using a 20 gauge, 1½" curved disposable feeding needle (Popper & Sons). Treatments were test compounds (30 mg/kg), a positive control (fenofibrate, 100 mg/kg) or vehicle [1% carboxymethylcellulose (w/v)/0.25% Tween80 (w/v); 0.2 ml/mouse]. Prior to termination on day 7, mice were weighed and dosed. Three hours after dosing, animals were anesthetized by inhalation of isoflurane (2–4%; Abbott Laboratories, Chicago, Ill.) and blood obtained via cardiac puncture (0.7–1.0 ml). Whole blood was transferred to serum separator tubes (Vacutainer SST), chilled on ice, and permitted to clot. Serum was obtained after centrifugation at 4° C. and frozen until analysis for triglycerides, total cholesterol, compound levels, and serum lipoprotein profile by fast protein liquid chromatography (FPLC) coupled to an inline detection system. After sacrifice by cervical dislocation, the liver, heart and epididymal fat pads were excised and weighed.

The animals dosed with vehicle had average triglycerides values of 60–80 mg/dl, which were reduced by the positive control fenofibrate (33–58 mg/dl with a mean reduction of 37%). The animals dosed with vehicle had average total serum cholesterol values of 140–180 mg/dl, which were increased by fenofibrate (190–280 mg/dl, with a mean elevation of 41%). When subject to EPLC analysis, pooled sera from vehicle-treated hu apoAI transgenic mice had a high density lipoprotein cholesterol (HDLc) peak area which ranged from 47 v-sec to 62 v-sec. Penofibrate increased the amount of HDLc (68–96 v-sec with a mean percent increase of 48%). Test compounds are reported in terms of percent increase in the area under the curve as indicated in Table 3.

TABLE 3

Percent increase of HDLc serum levels in mice receiving a compound of the invention over mice receiving vehicle.

| Example | % HDLc Increase |
|---------|-----------------|
| 4       | 40.4            |
| 5       | 94.5            |
| 19      | 85.3            |

Example 76

Evaluation of Glucose Levels in db/db Mice

Five week old male diabetic (db/db) mice [C57BlKs/j-m +/+ Lepr(db), Jackson Laboratory, Bar Harbor, Me.] or lean littermates (DB/?) were housed 6 per cage (10"20"8" with aspen chip bedding) with food (Purina 5015) and water available at all times. After an acclimation period of 2 weeks, animals were individually identified by ear notches, weighed, and bled via the tail vein for determination of initial glucose levels. Blood was collected (100 µl) from unfasted animals by wrapping each mouse in a towel, cutting the tip of the tail with a scalpel, and milking blood from the tail into a heparinized capillary tube (Fisher) balanced on the edge of the bench. Sample was discharged into a heparinized microtainer with gel separator (VWR) and retained on ice. Plasma was obtained after centrifugation at 4° C. and glucose measured immediately. Remaining plasma was frozen until the completion of the experiment, when glucose and triglycerides were assayed in all samples. Animals were grouped based on initial glucose levels and body weights. Beginning the following morning, mice were dosed daily by oral gavage for 7 days using a 20 gauge, 1½" curved disposable feeding needle. Treatments were test compounds (30 mg/kg), a positive control agent (30 mg/kg) or vehicle [1% carboxymethylcellulose (w/v)/0.25% Tween80 (w/v); 0.3 ml/mouse]. On day 7, mice were weighed and bled (tail vein) 3 hours after dosing. Twenty-four hours after the $7^{th}$ dose (i.e., day 8), animals were bled again (tail vein). Samples obtained from conscious animals on days 0, 7 and 8 were assayed for glucose. After the 24 hour bleed, animals were weighed and dosed for the final time. Three hours after dosing on day 8, animals were anesthetized by inhalation of isoflurane and blood obtained via cardiac puncture (0.5–0.7 ml). Whole blood was transferred to serum separator tubes, chilled on ice and permitted to clot. Serum was obtained after centrifugation at 4° C. and frozen until analysis for compound levels. After sacrifice by cervical dislocation, the liver, heart and epididymal fat pads were excised and weighed.

The animals dosed with vehicle had average triglycerides values of 170–230 mg/dl, which were reduced by the positive PPARα (70–120 mg/dl with a mean reduction of 50%). Male db/db mice were hyperglycemic (average glucose of 680–730 mg/dl on the $7^{th}$ day of treatment), while lean animals had average glucose levels between 190–230 mg/dl. Treatment with the positive control agent reduced glucose significantly (350–550 mg/dl with a mean decrease towards normalization of 56%). Test compounds are reported in Table 4 in terms of glucose normalization (i.e., 100% normalization would be glucose levels in treated db/db mice which did not differ from lean values.

Glucose was measured colorimetrically using commercially purchased reagents (Sigma #315-500). According to the manufacturers, the procedures were modified from published work (McGowan, M. W., Artiss, J. D., Strandbergh, D. R. & Zak, B. *Clin Chem*, 20:470–5 (1974) and Keston, A. Specific colorimetric enzymatic analytical reagents for glucose. *Abstract of papers* 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. *Ann Clin Biochem*, 6:24 (1969)). The absorbance of the dye produced is linearly related to the analyte in the sample. The assays were further modified in our laboratory for use in a 96 well format. Standards (Sigma #339-11, Sigma #16-11, and Sigma #CC0534 for glucose, triglycerides and total cholesterol, respectively), quality control plasma (Sigma # A2034), and samples (2 or 5 µl/well) were measured in duplicate using 200 µl of reagent. An additional aliquot of sample, pipetted to a third well and diluted in 200 µl water, provided a blank for each specimen. Plates were incubated at room temperature (18, 15, and 10 minutes for glucose, triglycerides and total cholesterol, respectively) on a plate shaker (DPC Micormix 5) and absorbance read at 500 nm (glucose and total cholesterol) or 540 nm (triglycerides) on a plate reader (Wallac Victor 1420). Sample absorbances were compared to a standard curve (100–800, 10–500, and 100–400 mg/dl for glucose, triglycerides and total cholesterol, respectively). Values for the quality control sample were always within the expected range and the coefficient of variation for samples was below 10%. All samples from an experiment were assayed at the same time to minimize inter-assay variability.

Serum lipoproteins were separated and cholesterol quantitated with an in-line detection system. Sample was applied to a Superose® 6 HR 10/30 size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min mixed with the column effluent through a T-connection and the mixture passed through a 15 m×0.5 mm id knitted tubing reactor immersed in a 37 C. water bath. The colored product produced in the presence of cholesterol was monitored in the flow stream at 505 nm and the analog voltage from the monitor was converted to a digital signal for collection and analysis. The change in voltage corresponding to change in cholesterol concentration was plotted vs time and the area under the curve corresponding to the elution of VLDL, LDL and HDL was calculated using Perkin Elmer Turbochrome software.

TABLE 4

Percent glucose normalisation values in db/db mice.

| Example | Glucose Normalisation |
|---------|-----------------------|
| 4       | 91                    |
| 5       | 71                    |

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by the following structural formula:

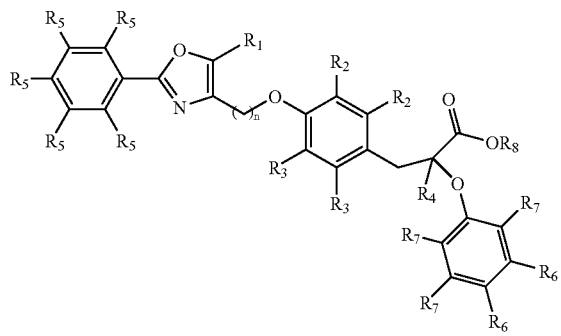

and pharmaceutically acceptable salts thereof, wherein:
n is 2, 3, or 4;
$R_1$ is H, a C1–C4 alkyl, phenyl or C1–C4 haloalkyl;
$R_2$ are each, independently, H, a C1–C6 alkyl, a C1–C4 alkoxy, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl;
$R_3$ are each, independently, H, a C1–C6 alkyl, a C1–C4 alkoxy, an aryl-C1–C6 alkyl, a cycloalkyl-C1–C4 alkyl, an aryl, or a cycloalkyl;
$R_4$ is a C1–C4 alkyl;
$R_5$ are each, independently, H, a substituted or unsubstituted aryl or a substituted or unsubstituted heteroaryl, provided that at least one or $R_5$ is a substituted or unsubstituted aryl or a substituted or unsubstituted heteroaryl;
$R_6$ is H, a C1–C4 alkyl, or an aminoalkyl;
$R_7$ are each, independently, H, a C1–C4 alkyl, a C1–C4 alkoxy, a halo, a C1-C4 haloalkyl, a C1–C4 haloalkoxy, or a cycloalkyl; and
$R_8$ are each, independently, H, a C1–C4 alkyl, a C1–C4 alkoxy, a halo, a C1-C4 haloalkyl, a C1–C4 haloalkoxy, a cycloalkyl, or each $R_8$ taken together with the phenyl to which they are attach is benzodioxolyl.

2. The compound of claim 1, wherein n is 2.

3. The compound of claim 2, wherein the compound is represented by the following structural formula:

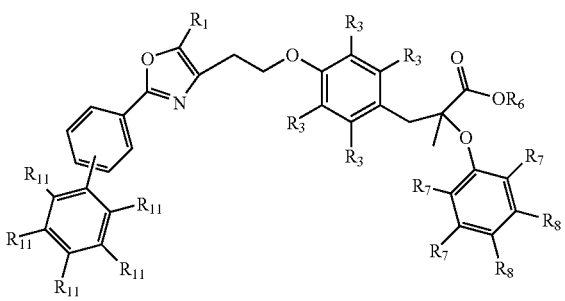

wherein $R_{11}$ are each, independently, H, a halo, a C1–C4 alkyl, or a C1–C4 alkoxy.

4. The compound of claim 3, wherein $R_1$ is methyl.

5. The compound of claim 4, wherein $R_7$ and $R_8$ are each H.

6. The compound of claim 2, wherein the compound is represented by the following structural formula:

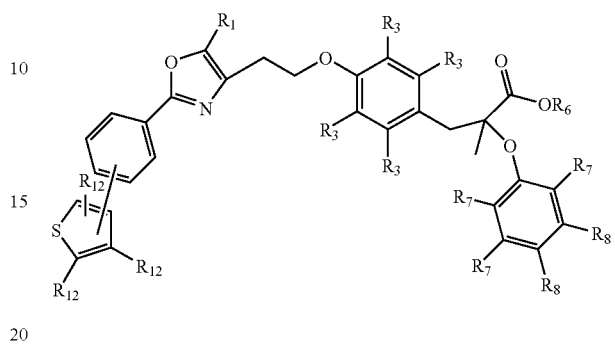

wherein, $R_{12}$ are each, independently, H, a halo, a C1–C4 alkyl, or a C1–C4 alkoxy.

7. The compound of claim 6, wherein $R_1$ is methyl.

8. The compound of claim 7, wherein $R_7$ and $R_8$ are each H.

9. The compound of claim 2, wherein the compound is represented by the following structural formula:

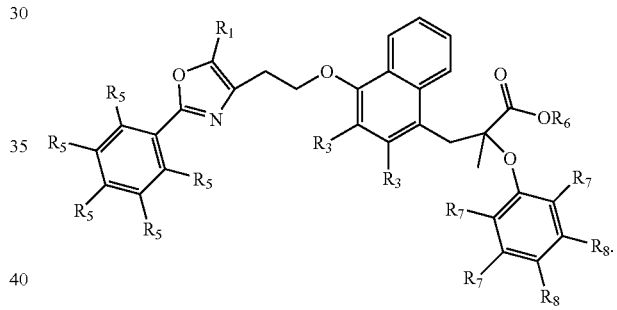

10. A compound selected from the group consisting of:
3-{4-[2-(2-Biphenyl-4-yl-5-methyl-oxazol-4-yl)-ethoxy]-phenyl}-2-methyl-2-phenoxypropionic acid;
3-{4-[2-(2-Biphenyl-3-yl-5-methyl-oxazol-4-yl)-ethoxy]-phenyl}-2-methyl-2-phenoxypropionic acid;
2-Methyl-3-(4-{2-[5-methyl-2-(4-thiophen-2-yl-phenyl)-oxazol-4-yl]-ethoxy}-phenyl)-2-phenoxypropionic acid;
3-(4-{(2-[2-(4'-Fluorobiphenyl-3-yl)-5-methyloxazol-4-yl]-ethoxy}phenyl)-2-methyl-2-phenoxypropionic acid;
2-Methyl-3-(4-{2-[5-methyl-2-(3-thiophen-2-ylphenyl)oxazol-4-yl]-ethoxy}phenyl)-2-phenoxypropionic acid;
2-Methyl-3-(4-{2-[5-methyl-2-(3-thiophen-3-ylphenyl)oxazol-4-yl]-ethoxy}phenyl)-2-phenoxypropionic acid;
3-{4-[2-(2-Biphenyl-4-yl-5-methyloxazol-4-yl)ethoxy]-3-methoxyphenyl}-2-methyl-2-phenoxypropionic acid;
3-{4-[2-(2-Biphenyl-3-yl-5-methyloxazol-4-yl)ethoxy]-3-methoxyphenyl}-2-methyl-2-phenoxypropionic acid;

3-(3-Methoxy-4-{2-[5-methyl-2-(4-thiophen-2-ylphenyl)oxazol-4-yl]-ethoxy}phenyl)-2-methyl-2-phenoxypropionic acid;

3-{4-[2-(2-Biphenyl-3-yl-5-methyl-oxazol-4-yl)ethoxy]-3-propyl-phenyl}-2-methyl-2-phenoxy-propionic acid;

2-Methyl-3-(4-{2-[5-methyl-2-(4-thiophen-2-yl-phenyl)-oxazol-4-yl]-ethoxy}-3-propyl-phenyl)-2-phenoxy-propionic acid;

3-{4-[2-(2-Biphenyl-4-yl-5-methyl-oxazol4-yl)-ethoxy]-naphthalen-1-yl}-2-methyl-2-phenoxypropionic acid;

3-{4-[2-(2-Biphenyl-3-yl-5-methyl-oxazol-4-yl)-ethoxy]-naphthalen-1-yl}-2-methyl-2-phenoxypropionic acid;

2-Methyl-3-(4-{2-[5-methyl-2-(4-thiophen-2-yl-phenyl)-oxazol-4-yl]-ethoxy}-naphthalen-1-yl)-2-phenoxypropionic acid;

3-{4-[2-(2-Biphenyl-4-yl-5-methyl-oxazol-4-yl)-ethoxy]-phenyl}-2-methyl-2-(4-tert-butylphenoxy)-propionic acid;

3-{4-[2-(2-Biphenyl-3-yl-5-methyl-oxazol-4-yl)-ethoxy]-phenyl}-2-methyl-2-(4-tert-butylphenoxy)-propionic acid;

2-Methyl-3-(4-{2-[5-methyl-2-(4-thiophen-2-yl-phenyl)-oxazol-4-yl]-ethoxy}-phenyl)-2-(4-tert-butylphenoxy)-propionic acid;

2-Methyl-3-(4-{2-[5-methyl-2-(3-thiophen-2-yl-phenyl)-oxazol-4-yl]-ethoxy}-phenyl)-2-(4-tert-butylphenoxy)-propionic acid;

2-Methyl-3-(4-{2-[5-methyl-2-(3-thiophen-3-yl-phenyl)-oxazol-4-yl]-ethoxy}-phenyl)-2-(4-tert-butylphenoxy)-propionic acid;

3-{4-[2-(2-Biphenyl-3-yl-5-methyl-oxazol-4-yl)-ethoxy]-phenyl}-2-(3-fluoro-phenoxy)-2-methyl-propionic acid;

3-{4-[2-(2-Biphenyl-4-yl-5-methyl-oxazol-4-yl)-ethoxy]-phenyl}-2-(3-fluoro-phenoxy)-2-methyl-propionic acid;

2-(3-Fluoro-phenoxy)-2-methyl-3-(4-{2-[5-methyl-2-(4-thiophen-2-yl-phenyl)-oxazol-4-yl]-ethoxy}-phenyl)-propionic acid;

3-{4-[2-(2-Biphenyl-4-yl-5-methyl-oxazol-4-yl)-ethoxy]-phenyl}-2-(3-tert-butyl-phenoxy)-2-methyl-propionic acid;

2-(3-tert-Butyl-phenoxy)-2-methyl-3-(4-{2-[5-methyl-2-(4-thiophen-2-yl-phenyl)-oxazol-4-yl]-ethoxy}-phenyl)-propionic acid;

2-(2-Fluoro-phenoxy)-2-methyl-3-(4-{2-[5-methyl-2-(4-thiophen-2-yl-phenyl)-oxazol-4-yl]-ethoxy}-phenyl)-propionic acid;

2-(4-Chlorophenoxy)-2-methyl-3-(4-{2-[5-methyl-2-(3-thiophen-2-yl-phenyl)-oxazol-4-yl]-ethoxy}-phenyl)-propionic acid;

3-{4-[2-(2-Biphenyl-4-yl-5-methyl-oxazol-4-yl)-ethoxy]-phenyl}-2-(4-chloro-phenoxy)-2-methyl-propionic acid;

3-{4-[2-(2-Biphenyl-3-yl-5-methyl-oxazol-4-yl)-ethoxy]-phenyl}-2-(4-chloro-phenoxy)-2-methyl-propionic acid;

2-(4-Cyclohexyl-phenoxy)-2-methyl-3-(4-{2-[5-methyl-2-(3-thiophen-2-yl-phenyl)-oxazol-4-yl]-ethoxy}-phenyl)-propionic acid;

3-{4-[2-(2-Biphenyl-4-yl-5-methyl-oxazol-4-yl)-ethoxy]-phenyl}-2-(4-cyclohexyl-phenoxy)-2-methyl-propionic acid;

3-{4-[2-(2-Biphenyl-3-yl-5-methyl-oxazol-4-yl)-ethoxy]-phenyl}-2-(4-cyclohexyl-phenoxy)-2-methyl-propionic acid;

2-(3,4-Dimethyl-phenoxy)-2-methyl-3-(4-{2-[5-methyl-2-(4-thiophen-2-yl-phenyl)-oxazol-4-yl]-ethoxy}-phenyl)-propionic acid;

3-{4-[2-(2-Biphenyl-4-yl-5-methyl-oxazol-4-yl)-ethoxy]-phenyl}-2-(3,4-dimethyl-phenoxy)-2-methyl-propionic acid;

3-{4-[2-(2-Biphenyl-4-yl-5-methyl-oxazol-4-yl)-ethoxy]-phenyl}-2-(3,4-dimethyl-phenoxy)-2-methyl-propionic acid;

(R)-2-Methyl-3-(4-{2-[5-methyl-2-(4-thiophen-2-yl-phenyl)-oxazol-4-yl]-ethoxy}-phenyl)-2-p-tolyloxy-propionic acid;

(R)-3-{4-[2-(2-Biphenyl-4-yl-5-methyl-oxazol-4-yl)-ethoxy]-phenyl}-2-methyl-2-p-tolyloxy-propionic acid;

3-{4-[2-(2-Biphenyl-4-yl-5-methyl-oxazol-4-yl)-ethoxy]-phenyl}-2-methyl-2-(4-trifluoromethoxy-phenoxy)-propionic acid;

3-{4-[2-(2-Biphenyl-3-yl-5-methyl-oxazol-4-yl)-ethoxy]-phenyl}-2-methyl-2-(4-trifluoromethoxy-phenoxy)-propionic acid;

2-Methyl-3-(4-{2-[5-methyl-2-(4-thiophen-2-yl-phenyl)-oxazol-4-yl]-ethoxy}-phenyl)-2-(4-trifluoromethoxy-phenoxy)-propionic acid;

2-{4-[2-(2-Biphenyl-4-yl-5-methyl-oxazol-4-yl)-ethoxy]-benzyl}-2-phenoxy-butyric acid;

2-{4-[2-(2-Biphenyl-3-yl-5-methyl-oxazol-4-yl)-ethoxy]-benzyl}-2-phenoxy-butyric acid;

2-(4-{2-[5-Methyl-2-(3-thiophen-2-yl-phenyl)-oxazol-4-yl]-ethoxy}-benzyl)-2-phenoxy-butyric acid;

3-{4-[2-(2-Biphenyl-4-yl-5-methyl-oxazol-4-yl)-ethoxy]-phenyl}-2-methyl-2-(4-trifluoromethyl-phenoxy)-propionic acid;

2-Methyl-3-(4-{2-[5-methyl-2-(4-thiophen-2-yl-phenyl)-oxazol-4-yl]-ethoxy}-phenyl)-2-(4-trifluoromethyl-phenoxy)-propionic acid;

3-{4-[2-(2-Biphenyl-4-yl-5-methyl-oxazol-4-yl)-ethoxy]-phenyl}-2-(3,4-difluoro-phenoxy)-2-methyl-propionic acid;

3-{4-[2-(2-Biphenyl-3-yl-5-methyl-oxazol-4-yl)-ethoxy]-phenyl}-2-(3,4-difluoro-phenoxy)-2-methyl-propionic acid;

2-(3,4-Difluoro-phenoxy)-2-methyl-3-(4-{2-[5-methyl-2-(4-thiophen-2-yl-phenyl)-oxazol-4-yl]-ethoxy}-phenyl)-propionic acid;

3-{4-[2-(2-Biphenyl-3-yl-5-methyl-oxazol-4-yl)-ethoxy]-phenyl}-2-methyl-2-m-tolyloxy-propionic acid;

3-{4-[2-(2-Biphenyl-4-yl-5-methyl-oxazol-4-yl)-ethoxy]-phenyl}-2-methyl-2-m-tolyloxy-propionic acid;

2-Methyl-3-(4-{2-[5-methyl-2-(4-thiophen-2-yl-phenyl)-oxazol-4-yl]-ethoxy}-phenyl)-2-m-tolyloxy-propionic acid;

3-{4-[2-(2-Biphenyl-3-yl-5-methyl-oxazol-4-yl)-ethoxy]-phenyl}-2-(4-fluoro-phenoxy)-2-methyl-propionic acid;

3-{4-[2-(2-Biphenyl-4-yl-5-methyl-oxazol-4-yl)-ethoxy]-phenyl}-2-(4-fluoro-phenoxy)-2-methyl-propionic acid;

2-(4-Fluoro-phenoxy)-2-methyl-3-(4-{2-[5-methyl-2-(4-thiophen-2-yl-phenyl)-oxazol-4-yl]-ethoxy}-phenyl)-propionic acid;

2-Methyl-3-(4-{2-[5-methyl-2-(4-thiophen-2-yl-phenyl)-oxazol-4-yl]-ethoxy}-phenyl)-2-(3-trifluoromethyl-phenoxy)-propionic acid;

3-{4-[2-(2-Biphenyl-3-yl-5-methyl-oxazol-4-yl)-ethoxy]-phenyl}-2-(3-methoxy-phenoxy)-2-methyl-propionic acid;

3-{4-[2-(2-Biphenyl-4-yl-5-methyl-oxazol-4-yl)-ethoxy]-phenyl}-2-(3-methoxy-phenoxy)-2-methyl-propionic acid;

2-(3-Methoxy-phenoxy)-2-methyl-3-(4-{2-[5-methyl-2-(4-thiophen-2-yl-phenyl)-oxazol-4-yl]-ethoxy}-phenyl)-propionic acid;

2-(Benzo[1,3]dioxol-5-yloxy)-3-{4-[2-(2-biphenyl-3-yl-5-methyl-oxazol-4-yl)-ethoxy]-phenyl}-2-methyl-propionic acid;

2-(Benzo[1,3]dioxol-5-yloxy)-3-{4-[2-(2-biphenyl-4-yl-5-methyl-oxazol-4-yl)-ethoxy]-phenyl}-2-methyl-propionic acid;

2-(Benzo[1,3]dioxol-5-yloxy)-2-methyl-3-(4-{2-[5-methyl-2-(3-thiophen-2-yl-phenyl)-oxazol-4-yl]-ethoxy}-phenyl)-propionic acid;

2-{4-[2-(2-Biphenyl-4-yl-5-methyl-oxazol-4-yl)-ethoxy]-benzyl}-2-phenoxy-hexanoic acid;

2-(4-{2-[5-Methyl-2-(3-thiophen-2-yl-phenyl)-oxazol-4-yl]-ethoxy}-benzyl)-2-phenoxy-hexanoic acid; and (R)-3-{4-[2-(2-Biphenyl-3-yl-5-methyl-oxazol-4-yl)-ethoxy]-phenyl}-2-methyl-2-p-tolyloxy-propionic acid.

11. A pharmaceutical composition, comprising a pharmaceutically acceptable carrier and at least one compound represented by the following structural formula:

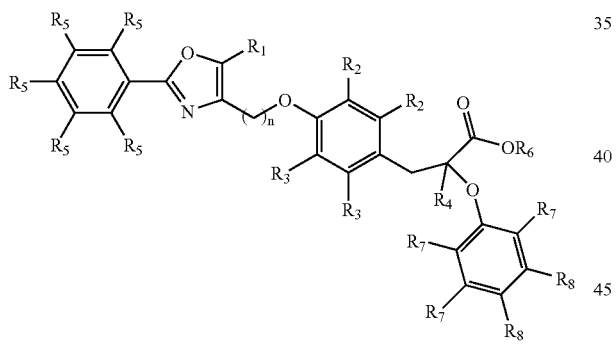

and pharmaceutically acceptable salts thereof, wherein:

n is 2, 3, or 4;

$R_1$ is H, a C1–C4 alkyl, phenyl or C1–C4 haloalkyl;

$R_2$ are each, independently, H, a C1–C6 alkyl, a C1–C4 alkoxy, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl;

$R_3$ are each, independently, H, a C1–C6 alkyl, a C1–C4 alkoxy, an aryl-C1–C6 alkyl, a cycloalkyl-C1–C4 alkyl, an aryl, or a cycloalkyl;

$R_4$ is a C1–C4 alkyl;

$R_5$ are each, independently, H, a substituted or unsubstituted aryl or a substituted or unsubstituted heteroaryl, provided that at least one or $R_5$ is a substituted or unsubstituted aryl or a substituted or unsubstituted heteroaryl;

$R_6$ is H, a C1–C4 alkyl, or an aminoalkyl;

$R_7$ are each, independently, H, a C1–C4 alkyl, a C1–C4 alkoxy, a halo, a C1–C4 haloalkyl, a C1–C4 haloalkoxy, or a cycloalkyl; and $R_8$ are each, independently, H, a C1–C4 alkyl, a C1–C4 alkoxy, a halo, a C1–C4 haloalkyl, a C1–C4 haloalkoxy, a cycloalkyl, or each $R_8$ taken together with the phenyl to which they are attach is benzodioxolyl.

12. The pharmaceutical composition of claim 11, wherein n is 2.

13. The pharmaceutical composition of claim 12, wherein the compound is represented by the following structural formula:

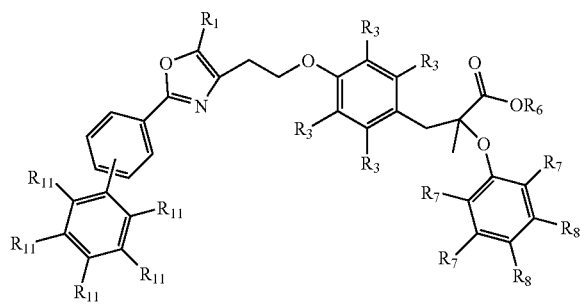

wherein $R_{11}$ are each, independently, H, a halo, a C1–C4 alkyl, or a C1–C4 alkoxy.

14. The pharmaceutical composition of claim 13, wherein $R_1$ is methyl.

15. The pharmaceutical composition of claim 14, wherein $R_7$ and $R_8$ are each H.

16. The pharmaceutical composition of claim 12, wherein the compound is represented by the following structural formula:

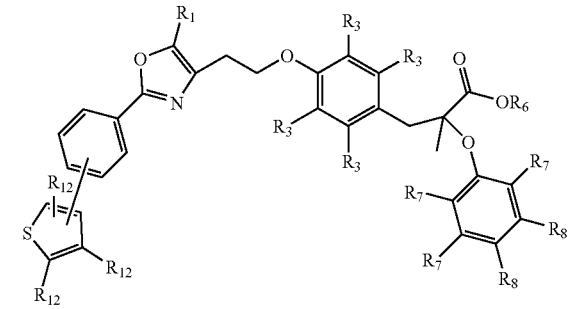

wherein, $R_{12}$ are each, independently, H, a halo, a C1–C4 alkyl, or a C1–C4 alkoxy.

17. The pharmaceutical composition of claim 16, wherein $R_1$ is methyl.

18. The pharmaceutical composition of claim 17, wherein $R_7$ and $R_8$ are each H.

19. The pharmaceutical composition of claim 12, wherein the compound is represented by the following structural formula:

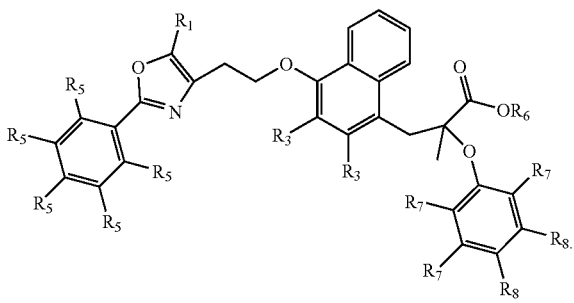

20. A pharmaceutical composition, comprising a pharmaceutically acceptable carrier and at least one compound selected from the group consisting of:

3-{4-[2-(2-Biphenyl-4-yl-5-methyl-oxazol-4-yl)-ethoxy]-phenyl}-2-methyl-2-phenoxypropionic acid;
3-{4-[2-(2-Biphenyl-3-yl-5-methyl-oxazol-4-yl)-ethoxy]-phenyl}-2-methyl-2-phenoxypropionic acid;
2-Methyl-3-(4-{2-[5-methyl-2-(4-thiophen-2-yl-phenyl)-oxazol-4-yl]-ethoxy}-phenyl)-2-phenoxypropionic acid;
3-(4-{2-[2-(4'-Fluorobiphenyl-3-yl)-5-methyloxazol-4-yl]-ethoxy}phenyl)-2-methyl-2-phenoxypropionic acid;
2-Methyl-3-(4-{2-[5-methyl-2-(3-thiophen-2-ylphenyl)oxazol-4-yl]-ethoxy}phenyl)-2-phenoxypropionic acid;
2-Methyl-3-(4-{2-[5-methyl-2-(3-thiophen-3-ylphenyl)oxazol-4-yl]-ethoxy}phenyl)-2-phenoxypropionic acid;
3-{4-[2-(2-Biphenyl-4-yl-5-methyloxazol-4-yl)ethoxy]-3-methoxyphenyl}-2-methyl-2-phenoxypropionic acid;
3-{4-[2-(2-Biphenyl-3-yl-5-methyloxazol-4-yl)ethoxy]-3-methoxyphenyl}-2-methyl-2-phenoxypropionic acid;
3-(3-Methoxy-4-{2-[5-methyl-2-(4-thiophen-2-ylphenyl)oxazol-4-yl]-ethoxy}phenyl)-2-methyl-2-phenoxypropionic acid;
3-{4-[2-(2-Biphenyl-3-yl-5-methyl-oxazol-4-yl)-ethoxy]-3-propyl-phenyl}-2-methyl-2-phenoxy-propionic acid;
2-Methyl-3-(4-{2-[5-methyl-2-(4-thiophen-2-yl-phenyl)-oxazol-4-yl]-ethoxy}-3-propyl-phenyl)-2-phenoxypropionic acid;
3-{4-[2-(2-Biphenyl-4-yl-5-methyl-oxazol-4-yl)-ethoxy]-naphthalen-1-yl}-2-methyl-2-phenoxypropionic acid;
3-{4-[2-(2-Biphenyl-3-yl-5-methyl-oxazol-4-yl)-ethoxy]-naphthalen-1-yl}-2-methyl-2-phenoxypropionic acid;
2-Methyl-3-(4-{2-[5-methyl-2-(4-thiophen-2-yl-phenyl)-oxazol-4-yl]-ethoxy}-naphthalen-1-yl)-2-phenoxypropionic acid;
3-{4-[2-(2-Biphenyl-4-yl-5-methyl-oxazol-4-yl)-ethoxy]-phenyl}-2-methyl-2-(4-tert-butylphenoxy)-propionic acid;
3-{4-[2-(2-Biphenyl-3-yl-5-methyl-oxazol-4-yl)-ethoxy]-phenyl}-2-methyl-2-(4-tert-butylphenoxy)-propionic acid;
2-Methyl-3-(4-{2-[5-methyl-2-(4-thiophen-2-yl-phenyl)-oxazol-4-yl]-ethoxy}-phenyl)-2-(4-tert-butylphenoxy)-propionic acid;
2-Methyl-3-(4-{2-[5-methyl-2-(3-thiophen-2-yl-phenyl)-oxazol-4-yl]-ethoxy}-phenyl)-2-(4-tert-butylphenoxy)-propionic acid;
2-Methyl-3-(4-{2-[5-methyl-2-(3-thiophen-3-yl-phenyl)-oxazol-4-yl]-ethoxy}-phenyl)-2-(4-tert-butylphenoxy)-propionic acid;
3-{4-[2-(2-Biphenyl-3-yl-5-methyl-oxazol-4-yl)-ethoxy]-phenyl}-2-(3-fluoro-phenoxy)-2-methyl-propionic acid;
3-{4-[2-(2-Biphenyl-4-yl-5-methyl-oxazol-4-yl)-ethoxy]-phenyl}-2-(3-fluoro-phenoxy)-2-methyl-propionic acid;
2-(3-Fluoro-phenoxy)-2-methyl-3-(4-{2-[5-methyl-2-(4-thiophen-2-yl-phenyl)-oxazol-4-yl]-ethoxy}-phenyl)-propionic acid;
3-{4-[2-(2-Biphenyl-4-yl-5-methyl-oxazol-4-yl)-ethoxy]-phenyl}-2-(3-tert-butyl-phenoxy)-2-methyl-propionic acid;
2-(3-tert-Butyl-phenoxy)-2-methyl-3-(4-{2-[5-methyl-2-(4-thiophen-2-yl-phenyl)-oxazol-4-yl]-ethoxy}-phenyl)-propionic acid;
2-(2-Fluoro-phenoxy)-2-methyl-3-(4-{2-[5-methyl-2-(4-thiophen-2-yl-phenyl)-oxazol-4-yl]-ethoxy}-phenyl)-propionic acid;
2-(4-Chlorophenoxy)-2-methyl-3-(4-{2-[5-methyl-2-(3-thiophen-2-yl-phenyl)-oxazol-4-yl]-ethoxy}-phenyl)-propionic acid;
3-{4-[2-(2-Biphenyl-4-yl-5-methyl-oxazol-4-yl)-ethoxy]-phenyl}-2-(4-chloro-phenoxy)-2-methyl-propionic acid;
3-{4-[2-(2-Biphenyl-3-yl-5-methyl-oxazol-4-yl)-ethoxy]-phenyl}-2-(4-chloro-phenoxy)-2-methyl-propionic acid;
2-(4-Cyclohexyl-phenoxy)-2-methyl-3-(4-{2-[5-methyl-2-(3-thiophen-2-yl-phenyl)-oxazol-4-yl]-ethoxy}-phenyl)-propionic acid;
3-{4-[2-(2-Biphenyl-4-yl-5-methyl-oxazol-4-yl)-ethoxy]-phenyl}-2-(4-cyclohexyl-phenoxy)-2-methyl-propionic acid;
3-{4-[2-(2-Biphenyl-3-yl-5-methyl-oxazol-4-yl)-ethoxy]-phenyl}-2-(4-cyclohexyl-phenoxy)-2-methyl-propionic acid;
2-(3,4-Dimethyl-phenoxy)-2-methyl-3-(4-{2-[5-methyl-2-(4-thiophen-2-yl-phenyl)-oxazol-4-yl]-ethoxy}-phenyl)-propionic acid;
3-{4-[2-(2-Biphenyl-4-yl-5-methyl-oxazol-4-yl)-ethoxy]-phenyl}-2-(3,4-dimethyl-phenoxy)-2-methyl-propionic acid;
3-{4-[2-(2-Biphenyl-4-yl-5-methyl-oxazol-4-yl)-ethoxy]-phenyl}-2-(3,4-dimethyl-phenoxy)-2-methyl-propionic acid;
(R)-2-Methyl-3-(4-{2-[5-methyl-2-(4-thiophen-2-yl-phenyl)-oxazol-4-yl]-ethoxy}-phenyl)-2-p-tolyloxy-propionic acid;
(R)-3-{4-[2-(2-Biphenyl-4-yl-5-methyl-oxazol-4-yl)-ethoxy]-phenyl}-2-methyl-2-p-tolyloxy-propionic acid;
3-{4-[2-(2-Biphenyl-4-yl-5-methyl-oxazol-4-yl)-ethoxy]-phenyl}-2-methyl-2-(4-trifluoromethoxy-phenoxy)-propionic acid;
3-{4-[2-(2-Biphenyl-3-yl-5-methyl-oxazol-4-yl)-ethoxy]-phenyl}-2-methyl-2-(4-trifluoromethoxy-phenoxy)-propionic acid;
2-Methyl-3-(4-{2-[5-methyl-2-(4-thiophen-2-yl-phenyl)-oxazol-4-yl]-ethoxy}-phenyl)-2-(4-trifluoromethoxy-phenoxy)-propionic acid;

2-{4-[2-(2-Biphenyl-4-yl-5-methyl-oxazol-4-yl)-ethoxy]-benzyl}-2-phenoxy-butyric acid;
2-{4-[2-(2-Biphenyl-3-yl-5-methyl-oxazol-4-yl)-ethoxy]-benzyl}-2-phenoxy-butyric acid;
2-(4-{2-[5-Methyl-2-(3-thiophen-2-yl-phenyl)-oxazol-4-yl]-ethoxy}-benzyl)-2-phenoxy-butyric acid;
3-{4-[2-(2-Biphenyl-4-yl-5-methyl-oxazol-4-yl)-ethoxy]-phenyl}-2-methyl-2-(4-trifluoromethyl-phenoxy)-propionic acid;
2-Methyl-3-(4-{2-[5-methyl-2-(4-thiophen-2-yl-phenyl)-oxazol-4-yl]-ethoxy}-phenyl)-2-(4-trifluoromethyl-phenoxy)-propionic acid;
3-{4-[2-(2-Biphenyl-4-yl-5-methyl-oxazol-4-yl)-ethoxy]-phenyl}-2-(3,4-difluoro-phenoxy)-2-methyl-propionic acid;
3-{4-[2-(2-Biphenyl-3-yl-5-methyl-oxazol-4-yl)-ethoxy]-phenyl}-2-(3,4-difluoro-phenoxy)-2-methyl-propionic acid;
2-(3,4-Difluoro-phenoxy)-2-methyl-3-(4-{2-[5-methyl-2-(4-thiophen-2-yl-phenyl)-oxazol-4-yl]-ethoxy}-phenyl)-propionic acid;
3-{4-[2-(2-Biphenyl-3-yl-5-methyl-oxazol-4-yl)-ethoxy]-phenyl}-2-methyl-2-m-tolyloxy-propionic acid;
3-{4-[2-(2-Biphenyl-4-yl-5-methyl-oxazol-4-yl)-ethoxy]-phenyl}-2-methyl-2-m-tolyloxy-propionic acid;
2-Methyl-3-(4-{2-[5-methyl-2-(4-thiophen-2-yl-phenyl)-oxazol-4-yl]-ethoxy}-phenyl)-2-m-tolyloxy-propionic acid;
3-{4-[2-(2-Biphenyl-3-yl-5-methyl-oxazol-4-yl)-ethoxy]-phenyl}-2-(4-fluoro-phenoxy)-2-methyl-propionic acid;
3-{4-[2-(2-Biphenyl-4-yl-5-methyl-oxazol-4-yl)-ethoxy]-phenyl}-2-(4-fluoro-phenoxy)-2-methyl-propionic acid;
2-(4-Fluoro-phenoxy)-2-methyl-3-(4-{2-[5-methyl-2-(4-thiophen-2-yl-phenyl)-oxazol-4-yl]-ethoxy}-phenyl)-propionic acid;
2-Methyl-3-(4-{2-[5-methyl-2-(4-thiophen-2-yl-phenyl)-oxazol-4-yl]-ethoxy}-phenyl)-2-(3-trifluoromethyl-phenoxy)-propionic acid;
3-{4-[2-(2-Biphenyl-3-yl-5-methyl-oxazol-4-yl)-ethoxy]-phenyl}-2-(3-methoxy-phenoxy)-2-methyl-propionic acid;
3-{4-[2-(2-Biphenyl-4-yl-5-methyl-oxazol-4-yl)-ethoxy]-phenyl}-2-(3-methoxy-phenoxy)-2-methyl-propionic acid;
2-(3-Methoxy-phenoxy)-2-methyl-3-(4-{2-[5-methyl-2-(4-thiophen-2-yl-phenyl)-oxazol-4-yl]-ethoxy}-phenyl)-propionic acid;
2-(Benzo[1,3]dioxol-5-yloxy)-3-{4-[2-(2-biphenyl-4-yl-5-methyl-oxazol-4-yl)-ethoxy]-phenyl}-2-methyl-propionic acid;
2-(Benzo[1,3]dioxol-5-yloxy)-2-methyl-3-(4-{2-[5-methyl-2-(3-thiophen-2-yl-phenyl)-oxazol-4-yl]-ethoxy}-phenyl)-propionic acid;
2-{4-[2-(2-Biphenyl-4-yl-5-methyl-oxazol-4-yl)-ethoxy]-benzyl}-2-phenoxy-hexanoic acid;
2-{4-[2-(2-Biphenyl-3-yl-5-methyl-oxazol-4-yl)-ethoxy]-benzyl}-2-phenoxy-hexanoic acid;
2-(4-{2-[5-Methyl-2-(3-thiophen-2-yl-phenyl)-oxazol-4-yl]-ethoxy}-benzyl)-2-phenoxy-hexanoic acid; and
(R)-3-{4-[2-(2-Biphenyl-3-yl-5-methyl-oxazol-4-yl)-ethoxy]-phenyl}-2-methyl-2-p-tolyloxy-propionic acid.

21. A method of modulating a peroxisome proliferator activated receptor B1, comprising the step of contacting the receptor with at least one compound represented by the following structural formula:

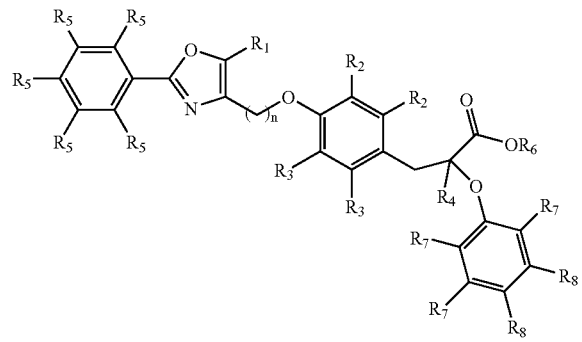

and pharmaceutically acceptable slats, solvates and hydrates thereof, wherein;

n is 2, 3, or 4;

$R_1$ is H, a C1–C4 alkyl, phenyl or C1–C4 haloalkyl;

$R_2$ are each, independently, H, a C1–C6 alkyl, a C1–C4 alkoxy, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl;

$R_3$ are each, independently, H, a C1–C6 alkyl, a C1–C4 alkoxy, an aryl-C1–C6 alkyl, a cycloalkyl-C1–C4 alkyl, an aryl, or a cycloalkyl;

$R_4$ is a C1–C4 alkyl;

$R_5$ are each, independently, H, a substituted or unsubstituted aryl or a substituted or unsubstituted heteroaryl, provided that at least one or $R_5$ is a substituted or unsubstituted aryl or a substituted or unsubstituted heteroaryl;

$R_6$ is H, a C1–C4 alkyl, or an aminoalkyl;

$R_7$ are each, independently, H, a C1–C4 alkyl, a C1–C4 alkoxy, a halo, a C1–C4 haloalkyl, a C1–C4 haloalkoxy, or a cycloalkyl; and $R_8$ are each, independently, H, a C1–C4 alkyl, a C1–C4 alkoxy, a halo, a C1–C4 haloalkyl, a C1–C4 haloalkoxy, a cycloalkyl, or each $R_8$ taken together with the phenyl to which they are attach is benzodioxolyl.

22. A method of treating diabetes mellitus in a mammal, comprising the step of administering to the mammal a therapeutically effective amount of at least one compound represented by the following structural formula:

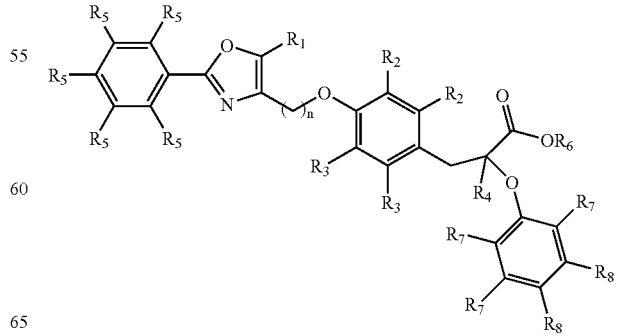

and pharmaceutically acceptable salts, solvates and hydrates thereof, wherein:

n is 2, 3, or 4;

$R_1$ is H, a C1–C4 alkyl, phenyl or C1–C4 haloalkyl;

$R_2$ are each, independently, H, a C1–C6 alkyl, a C1–C4 alkoxy, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl;

$R_3$ are each, independently, H, a C1–C6 alkyl, a C1–C4 alkoxy, an aryl-C1–C6 alkyl, a cycloalkyl-C1–C4 alkyl, an aryl, or a cycloalkyl;

$R_4$ is a C1–C4 alkyl;

$R_5$ are each, independently, H, a substituted or unsubstituted aryl or a substituted or unsubstituted heteroaryl, provided that at least one or $R_5$ is a substituted or unsubstituted aryl or a substituted or unsubstituted heteroaryl;

$R_6$ is H, a C1–C4 alkyl, or an aminoalkyl;

$R_7$ are each, independently, H, a C1–C4 alkyl, a C1–C4 alkoxy, a halo, a C1–C4 haloalkyl, a C1–C4 haloalkoxy, or a cycloalkyl; and $R_8$ are each, independently, H, a C1–C4 alkyl, a C1–C4 alkoxy, a halo, a C1–C4 haloalkyl, a C1–C4 haloalkoxy, a cycloalkyl, or each $R_8$ taken together with the phenyl to which they are attach is benzodioxolyl.

23. The method of claim 22, wherein the mammal is a human.

24. The method of claim 22, wherein the compound potentiates a peroxisome proliferator activated receptor.

25. The method of claim 24, wherein the peroxisome proliferator activated receptor is a γ receptor.

26. The method of claim 24, wherein the compound lowers blood glucose levels.

27. A method of treating cardiovascular disease in a mammal, comprising the step of administering to the mammal a therapeutically effective amount of at least one compound represented by the following structural formula:

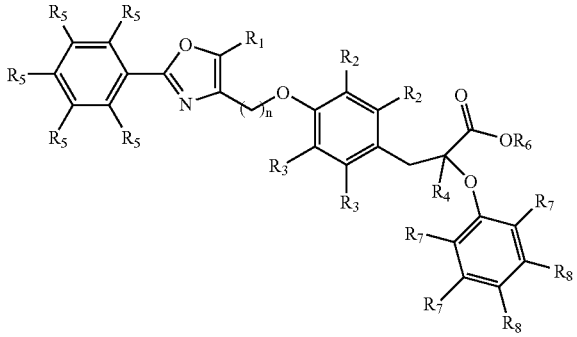

and pharmaceutically acceptable salts, solvates and hydrates thereof, wherein:

n is 2, 3, or 4;

$R_1$ is H, a C1–C4 alkyl, phenyl or C1–C4 haloalkyl;

$R_2$ are each, independently, H, a C1–C6 alkyl, a C1–C4 alkoxy, an aryl-C1–C6 alkyl, a cycloalkyl-C1–C4 alkyl, an aryl, or a cycloalkyl, $R_4$ is a C1–C4 alkyl;

$R_5$ are each, independently, H, a substituted or unsubstituted aryl or a substituted or unsubstituted heteroaryl, provided that at least one or $R_5$ is a substituted or unsubstituted aryl or a substituted or unsubstituted heteroaryl;

$R_6$ is H, a C1–C4 alkyl, or an aminoalkyl;

$R_7$ are each, independently, H, a C1–C4 alkyl, a C1–C4 alkoxy, a halo, a C1–C4 haloalkyl, a C1–C4 haloalkoxy, or a cycloalkyl; and $R_8$ are each, independently, H, a C1–C4 alkyl, a C1–C4 alkoxy, a halo, a C1–C4 haloalkyl, a C1–C4 haloalkoxy, a cycloalkyl, or each $R_8$ taken together with the phenyl to which they are attach is benzodioxolyl.

28. The method of claim 27, wherein the mammal is a human.

29. The method of claim 27, wherein the compound potentiates a peroxisome proliferator activated receptor.

30. The method of claim 29, wherein the peroxisome proliferator activated receptor is an α receptor.

31. The method of claim 29, wherein the compound lowers triglycerides in the mammal.

32. The method of claim 29, wherein the compound lowers low density lipoproteins in the mammal.

33. The method of claim 29, wherein the compound increases high density lipoproteins in a mammal.

34. A method of treating Syndrome X in a mammal, comprising the step of administering to the mammal a therapeutically effective amount of at least one compound represented by the following structural formula:

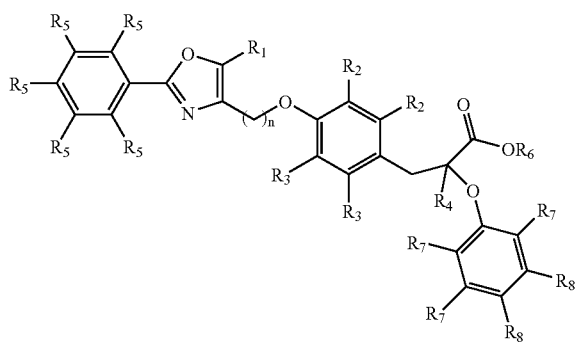

and pharmaceutically acceptable salts, solvates and hydrates thereof, wherein:

n is 2, 3, or 4;

$R_1$ is H, a C1–C4 alkyl, phenyl or C1–C4 haloalkyl;

$R_2$ are each, independently, H, a C1–C6 alkyl, a C1–C4 alkoxy, an aryl-C1–C6 alkyl, a cycloalkyl-C1–C4 alkyl, an aryl, a cycloalkyl, or together with the phenyl to which they are bound form naphthyl or 1,2,3,4-tetrahydronaphthyl;

$R_3$ are each, independently, H, a C1–C6 alkyl, a C1–C4 alkoxy, an aryl-C1–C6 alkyl, a cycloalkyl-C1–C4 alkyl, an aryl, or a cycloalkyl;

$R_4$ is a C1–C4 alkyl;

$R_5$ are each, independently, H, a substituted or unsubstituted aryl or a substituted or unsubstituted heteroaryl, provided that at least one or $R_5$ is a substituted or unsubstituted aryl or a substituted or unsubstituted heteroaryl;

$R_6$ is H, a C1–C4 alkyl, or an aminoalkyl;

$R_7$ are each, independently, H, a C1–C4 alkyl, a C1–C4 alkoxy, a halo, a C1–C4 haloalkyl, a C1–C4 haloalkoxy, or a cycloalkyl; and R$_8$ are each, independently, H, a C1–C4 alkyl, a C1–C4 alkoxy, a halo, a C1–C4 haloalkyl, a C1–C4 haloalkoxy, a cycloalkyl, or each R$_8$ taken together with the phenyl to which they are attach is benzodioxolyl.

35. The method of claim 34, wherein the compound potentiates a peroxisome proliferator activated receptor.

36. The method of claim 35, wherein the compound lowers blood glucose levels.

37. The method of claim 35, wherein the compound lowers serum concentration of triglycerides in the mammal.

38. The method of claim 35, wherein the compound lowers serum concentration of low density lipoproteins in the mammal.

39. The method of claim 35, wherein the compound increases serum concentration of high density lipoproteins in a mammal.

40. A compound as claimed by claim 1 selected from the group consisting of: 3-{4-[2-(2-Biphenyl-4-yl-5-methyl-oxazol-4-yl)-ethoxy]-phenyl}-2-methyl-2-o-tolyloxy-propionic acid, 3-{4-[2-(2-Biphenyl-4-yl-5-methyloxazol-4-yl)-ethoxy]-phenyl}-2-(2-methoxy-phenoxy)-2-methyl-propionic acid, and 2-(2-Methoxy-phenoxy)-2-methyl-3-(4-{2-[5-methyl-2-(3-thiophen-2-yl-phenyl)-oxazol-4-yl]-ethoxy}-phenyl)-propionic acid.

* * * * *